United States Patent
Bardroff et al.

(10) Patent No.: US 8,420,787 B2
(45) Date of Patent: Apr. 16, 2013

(54) ORGANIC COMPOUNDS

(75) Inventors: Michael Bardroff, Lorrach (DE); Matthew Edwards, Horsham (GB); Mehmet Kemal Tur, Aachen (DE); Olaf Ratsch, Gräfelfing (DE)

(73) Assignee: Novartis AG, Basel (CH)

( * ) Notice: Subject to any disclaimer, the term of this patent is extended or adjusted under 35 U.S.C. 154(b) by 628 days.

(21) Appl. No.: 12/280,674

(22) PCT Filed: Feb. 21, 2007

(86) PCT No.: PCT/EP2007/001506
§ 371 (c)(1), (2), (4) Date: Aug. 25, 2008

(87) PCT Pub. No.: WO2007/096149
PCT Pub. Date: Aug. 30, 2007

(65) Prior Publication Data
US 2009/0186022 A1    Jul. 23, 2009

(30) Foreign Application Priority Data
Feb. 23, 2006  (GB) .................................. 0603683.4

(51) Int. Cl.
C12P 21/08 (2006.01)
(52) U.S. Cl.
USPC ................... 530/387.3; 530/350; 530/388.15
(58) Field of Classification Search ................. 530/350, 530/387.3, 388.15
See application file for complete search history.

(56) References Cited

U.S. PATENT DOCUMENTS

| | | |
|---|---|---|
| 6,890,734 B2 | 5/2005 | Reche-Gallardo et al. |
| 7,071,308 B2 | 7/2006 | Reche-Gallardo et al. |
| 7,569,224 B2 | 8/2009 | Reche-Gallardo et al. |
| 2009/0017034 A1 | 1/2009 | Sims et al. |
| 2009/0238823 A1 | 9/2009 | Comeau et al. |

FOREIGN PATENT DOCUMENTS

| | | |
|---|---|---|
| EP | 1129190 A1 | 9/2001 |
| WO | WO 00/17362 A1 | 3/2000 |
| WO | WO 00/29581 A1 | 5/2000 |
| WO | WO03/065985 A2 | 8/2003 |
| WO | WO 2006/083947 A2 | 8/2006 |
| WO | WO 2008/076321 A1 | 6/2008 |
| WO | WO 2009/035577 A1 | 3/2009 |

OTHER PUBLICATIONS

"Anti-human TSLP Antibody AF1398", R&D Systems Inc., http://www.mdsystems.com/pdf/af1398.pdf, Feb. 15, 2006.
Soumelis et al., "Human epithelial cells trigger dendritic cell mediated allergic inflammation by producing TSLP", Nature Immunology, 2002 vol. 3 No. 7 pp. 673-680.
Soumelis et al., "Human thymic stromal lymphopoietin: a novel epithelial cell-derived cytokine and a potential key player in the induction of allergic inflammation", Springer Seminar in Immunopathology, 2004 vol. 25 No. 3-4 pp. 325-333.
Chen et al; "Selection and Analysis of an Optimized Anti-VEGF Antibody: Crystal Structure of an Affinity-matured Fab in Complex with Antigen"; Journal of Molecular Biology 293:865-881 (1999).
Comeau et al; "The influence of TSLP on the allergic response"; Mucosal Immunology 3(2):138-147 (2010).
Schier et al; "Isolation of Picomolar Affinity Anti-c-erbB-2 Single-chain Fv by Molecular Evolution of the Complementarity Determining Regions in the Center of the Antibody Binding Site"; Journal of Molecular Biology 263:551-567 (1996).
Yang et al; "CDR Walking Mutagenesis for the Affinity Maturation of a Potent Human Anti-HIV-1 Antibody into the Picomolar Range"; Journal of Molecular Biology 254:392-403 (1995).
Documents filed in opposition proceedings to EP1129190 Feb. 13, 2008-Sep. 8, 2010.

*Primary Examiner* — Brad Duffy
(74) *Attorney, Agent, or Firm* — Frank Wu

(57) ABSTRACT

The present invention relates to human thymic stromal lymphopoietin (hTSLP) antibodies and especially those which neutralize hTSLP activity. It further relates to methods for using anti-hTSLP antibody molecules in diagnosis or treatment of hTSLP related disorders, such as asthma, atopic dermatitis, allergic rhinitis, fibrosis inflammatory bowel disease, and Hodgkin's lymphoma.

4 Claims, 1 Drawing Sheet

ORGANIC COMPOUNDS

This application is a U.S. National Phase filing of International Application Serial No., PCT/EP2007/001506 filed 21 Feb. 2007, and claims priority to G.B. Application Serial No, 0603683.4 filed 23 Feb. 2006, the contents of which are incorporated herein by reference in their entirety.

FIELD OF USE

The present invention relates to human thymic stromal lymphopoietin (hTSLP) antibodies and especially those which neutralize hTSLP activity. It further relates to methods for using anti-hTSLP antibody molecules in diagnosis or treatment of hTSLP related disorders, such as asthma, atopic dermatitis, allergic rhinitis, fibrosis, inflammatory bowel disease and Hodgkin's lymphoma.

BACKGROUND OF THE INVENTION

Human thymic stromal lymphopoietin (hTSLP) (GenBank accession number: NM_033035), an interleukin-7 (IL-7) like cytokine, which is produced by human epithelial stroma and mast cells, initiates the allergic response by the stimulation of dendritic cells (DC). The deduced 159-amino acid protein is 43% identical to mouse TSLP, contains a 28-residue signal sequence, 6 cysteines, and 2 putative N-glycosylation sites. Native Sodium Dodecyl Sulfate Polyacrylamide Gel Electrophoresis (SDS-PAGE) analysis showed expression of a 23 kilo Dalton (kDa) protein, whereas the calculated molecular mass of the mature protein is 14.9 kDa, suggesting that hTSLP is glycosylated. hTSLP contains 7 basic C-terminal amino acids (aa) N-Lysine-Lysine-Arginine-Arginine-Lysine-Arginine-Lysine-C (KKRRKRK) (SEQ ID NO:115) and 6 cysteines probably involved in disulfide bond formation.

hTSLP is highly expressed by epithelial cells of inflamed tonsils and keratinocytes of atopic dermatitis and its expression is associated with Langerhans cell migration and activation[2].

The TSLP receptor complex is a heterodimer comprised of the TSLP receptor (TSLPR) and IL-7 receptor alpha (IL-7Ra) chain. The receptor is expressed primarily on monocytes and myeloid-derived DC, as well as on B lymphocytes[3].

Allergy is the result of a complex immune cascade leading to the dysregulated production of the Thymus-derived helper cell type 2 (Th2) subset lymphocyte cytokines, the generation of allergen-specific IgE-producing B lymphocytes and the subsequent activation and degranulation of mast cells upon allergen challenge.

DC play an important role in several models of allergy whereby TSLP-activated human DC produce Th2-attracting chemokines but no IL-112, and induce naïve CD4- and CD8-antigen-positive T lymphocyte differentiation into effector cells with a typical pro-allergic phenotype.

Atopic dermatitis (AD) represents a chronic, relapsing inflammatory skin disease with characteristic clinical features[4]. Genetic background, environmental exposures such as food allergens, aeroallergens, microbial antigens, or stress, and distinct immunological predispositions all contribute to the development of periodic, itchy eczematous skin lesions in afflicted patients. Several soluble factors have been shown to be increased in the peripheral blood of patients with AD. These cytokines and chemokines play an important role in regulating DC differentiation, activation and migration and are important in coordinating the trafficking of immune cells. hTSLP, which is produced by human epithelial stroma and mast cells, initiates the allergic response by the stimulation of DC. TSLP activated DC produce the CC chemokines that induce the chemotaxis and polarization of allergen-specific effector lymphocytes[5]. Thus, epithelial- and stromal-cell-derived TSLP might represent one of the factors initiating the allergic responses, and could be a target for a curative therapeutic approach to allergy.

In recent studies, one anti-human TSLP polyclonal antibody was described (R&D Systems, AF1398). This antibody was produced in sheep immunized with purified E. coli-derived recombinant TSLP. Human TSLP specific sheep IgG was purified by hTSLP affinity chromatography. This polyclonal antibody was selected for its ability to neutralize hTSLP bioactivity and showed less than 1% cross-reactivity with recombinant murine TSLP. The Neutralization Dose$_{50}$ (ND$_{50}$) for this antibody was defined as that concentration of antibody required to yield one-half maximal inhibition of the recombinant hTSLP activity on the responsive cell line mouse BaF/3 cells co-transfected with IL-7Ra and hTSLPR chains, as an assay. The ND$_{50}$ was determined to be approximately 0.05-0.25 μg/ml in the presence of 0.5 ng/ml recombinant hTSLP. The disadvantage of polyclonal antibodies is that they are in a limited supply as there is a restricted supply of serum from the same treated animal. In addition, polyclonal antibodies recognize multiple epitopes on the same antigen and may have undesired cross-reactivity. While polyclonal serum contains a mixture of both high and low affinity binders, targeting also a range of epitopes, a monoclonal antibody approach make sure to select the most useful candidate for a therapeutic use.

Animal-derived polyclonal antibodies when injected in humans constitute a foreign protein in a human host, they often elicit an antiglobulin response due to their immunogenicity in human. This antiglobulin response, which is predominantly directed against the constant domains of the animal antibodies, usually precludes treatment after repeated administration.

SUMMARY OF THE INVENTION

An embodiment of the invention herein provides an isolated human or humanized antibody or functional fragment thereof with an antigen-binding region that is specific for target protein hTSLP and the antibody or functional fragment thereof binds to hTSLP. In a related embodiment, the binding to hTSLP is determined at least by cell surface hTSLP receptor binding preventing inflammatory mediator release.

In still another embodiment, the invention provides an isolated antigen-binding region of an antibody or functional fragment thereof. In certain embodiments, the isolated antigen-binding region includes an H-CDR1 region having an amino acid sequence selected from SEQ ID NOs: 1-7, and conservative variants thereof. As described herein, the conservative variants include amino acid residues in any of the amino acid sequences identified. In a related embodiment, the isolated antigen-binding region is an H-CDR2 region having an amino acid sequence selected from SEQ ID NOs: 8-25, and conservative variants thereof. In another related embodiment, the isolated antigen-binding region is an H-CDR3 region having an amino acid sequence selected from SEQ ID NO: 26-31, and conservative variants thereof.

In another embodiment, the isolated antigen-binding region is an L-CDR1 region having an amino acid sequence selected from SEQ ID NOs: 32-40, and conservative variants thereof. In still another related embodiment, the isolated antigen-binding region is an L-CDR2 region having an amino acid sequence selected from SEQ ID NOs: 41-49, and conservative variants thereof. In yet another related embodiment, the isolated antigen-binding region is an L-CDR3 region having an amino acid sequence selected from SEQ ID NOs: 50-66, and conservative variants thereof.

In another embodiment, the isolated antigen-binding region is a heavy chain having an amino acid sequence selected from one to three of SEQ ID 1-31, and a sequence having at least 60, 70, 80, 90 or 95 percent sequence identity in the CDR regions with the CDR regions having SEQ ID NOs: 1-31. In a related embodiment, the isolated antigen-binding region is a light chain having an amino acid sequence selected from one to three of SEQ ID NOs: 32-66, and a sequence having at least 60, 70, 80, 90 or 95 percent sequence identity in the CDR regions with the CDR regions having SEQ ID NOs: 32-66.

In a certain embodiment, the isolated antibody is an IgG. In another embodiment, the isolated antibody is an IgG1, IgG2 or an IgG4.

In yet another embodiment, the invention provides an isolated human or humanized antibody or functional fragment thereof, having an antigen-binding region that is specific for an epitope of hTSLP, and the antibody or functional fragment binds to hTSLP surface receptors on a cell. In a related embodiment, the invention provides an isolated human or humanized antibody or functional fragment thereof, having an antigen-binding region that is specific for an epitope of target hTSLP, and the epitope contains one or more amino acid residues of amino acid residues 1-112 of target hTSLP. In a related embodiment, the epitope is a conformational epitope.

In yet another embodiment, the antibody or functional fragment is a Fab or scFv antibody fragment. In a related embodiment, the isolated antibody is an IgG. In another related embodiment, the isolated antibody is an IgG1, IgG2 or an IgG4.

In another embodiment, the invention provides a pharmaceutical composition having at least one of any of the above antibodies or functional fragments or conservative variants, and a pharmaceutically acceptable carrier or excipient therefor.

In still another embodiment, the invention provides for a transgenic animal carrying a gene encoding any of the above antibodies or functional fragments thereof.

In certain embodiments, the invention provides a method for treating a disorder or condition associated with the presence of a cell having a receptor target hTSLP. The method involves administering to a subject in need thereof an effective amount of any of the above pharmaceutical compositions. In a related embodiment, the disorder or condition to be treated is a respiratory disorder.

In another embodiment, the disorder or condition to be treated is bronchial asthma, which is a common persistent inflammatory disease of the lung characterised by airways hyper-responsiveness (AHR), mucus overproduction, fibrosis and raised serum IgE levels. A significant role for TSLP has been demonstrated in a mouse model in which lung specific expression of TSLP transgene induced allergic inflammation, goblet cell hyperplasia, subepithelial fibrosis and increased IgE levels (Zhou B, et al Nat. Immunol. 6: 1047-1053). Also mice lacking the TSLP-receptor were protected from allergic responses when exposed to aerosolized antigen challenge. In addition a link between TSLP expression levels in lung epithelial cells and asthmatic disease severity has been described in humans (Ying, S. B. et al. J. Immunol. 174: 8183-8190).

In another embodiment, the disorder or condition to be treated is atopic (allergic) dermatitis, which is the most common skin disease in childhood and is characterized by intense pruritus and chronic eczematous plaques. A significant role for TSLP has been demonstrated in a mouse model in which skin specific expression of TSLP transgene induced eczematous skin lesions containing inflammatory cell infiltrates, an increase in circulating Th2 cells and an increase in serum IgE (Yoo, J. et al. J. Exp. Med. 202: 541-549). Also in humans TSLP has been found to be highly expressed in tissue sections of atopic dermatitis lesions which was associated with Langerhans cell migration and activation (Soumelis, V. et al. Nat. Immunol. 3: 673-680).

In another embodiment, the disorder or condition to be treated is selected from other inflammatory or obstructive airways diseases and conditions such as COPD, acute lung injury (ALI), acute/adult respiratory distress syndrome (ARDS), dyspnea, allergic airway inflammation, small airway disease, lung carcinoma, acute chest syndrome in patients with sickle cell disease and pulmonary hypertension, as well as exacerbation of airways hyperreactivity consequent to other drug therapy, in particular other inhaled drug therapy.

In another embodiment, the disorder or condition to be treated is bronchitis of whatever type or genesis including, e.g., acute, arachidic, catarrhal, croupus, chronic or phthinoid bronchitis.

In another embodiment, the disorder or condition to be treated includes pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

In another embodiment, the disorder or condition to be treated is selected from atopic rhinitis (hay fever) and chronic sinusitis.

In another embodiment, the disorder or condition to be treated is selected from other inflammatory conditions of the skin, for example, psoriasis or lupus erythematosus.

In another embodiment, the disorder or condition to be treated is inflammatory bowel disease, such as ulcerative colitis and Crohn's disease.

In another embodiment, the disorder or condition to be treated is selected from other fibrotic conditions, such as systemic sclerosis, liver fibrosis, pulmonary fibrosis, idiopathic pulmonary fibrosis or fibroid lung.

In another embodiment, the disorder or condition to be treated is tumour recurrence or metastasis. Inhibition of Th2 cytokines has been shown to enhance anti-viral vaccines in animal models and may be beneficial in the treatment of HIV and other infectious diseases [Ahlers, J. D., et al. Proc Natl Acad Sci USA, 2002].

In another embodiment, the disorder or condition to be treated is a respiratory viral infection, which exacerbates underlying chronic conditions such as asthma, chronic bronchitis, COPD, otitis media, and sinusitis. The respiratory viral infection treated may be associated with secondary bacterial infection, such as otitis media, sinusitis or pneumonia.

In another embodiment, the disorder or condition to be treated is selected from other diseases or conditions, in particular diseases or conditions having an inflammatory component, for example, diseases of the bone and joints including rheumatoid arthritis, psoriatic arthritis, and other diseases such as atherosclerosis, multiple sclerosis, and acute and chronic allograft rejection, e.g. following transplantation of heart, kidney, liver, lung or bone marrow.

In another embodiment, the disorder or condition to be treated is endotoxic shock, glomerulonephritis, cerebral and cardiac ischemia, Alzheimer's disease, cystic fibrosis, virus infections and the exacerbations associated with them, acquired immune deficiency syndrome (AIDS), multiple sclerosis (MS), *Helicobacter pylori* associated gastritis, and cancers, particularly the growth of ovarian cancer.

In another embodiment, the disorder or condition to be treated is the symptoms caused by viral infection in a human which is caused by the human rhinovirus, other enterovirus, coronavirus, herpes viruses, influenza virus, parainfluenza virus, respiratory syncytial virus or an adenovirus.

Treatment in accordance with the present invention may be symptomatic or prophylactic.

The effectiveness of an agent of the invention in inhibiting inflammatory conditions, for example in inflammatory airways diseases, may be demonstrated in an animal model, e.g. mouse, rat or rabbit model, of airway inflammation or other inflammatory conditions, for example as described by Wada et al, *J. Exp. Med* (1994) 180:1135-40; Sekido et al, *Nature* (1993) 365:654-57; Modelska et al., *Am. J. Respir. Crit. Care. Med.* (1999) 160:1450-56; and Laffon et al (1999) *Am. J. Respir. Crit. Care Med.* 160:1443-49.

In yet another embodiment, the invention provides a method for identifying a cell having a receptor for hTSLP. This method involves contacting the cell with any of the above antibodies or antibody fragments further having a detectable label. The label is radioactive, fluorescent, magnetic, paramagnetic, or chemiluminescent. The method further can involve any of the above imaging or separating the labeled cell.

In another embodiment, any of the above human or humanized antibodies or antibody fragments are synthetic.

In another embodiment, the invention provides a pharmaceutical composition and an additional therapeutic agent.

The additional therapeutic agent can be selected from the group consisting of anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. A therapeutic agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700; LTD4 antagonists such include montelukast, pranlukast, zafirlukast, accolate, SR2640, Wy-48,252, ICI 198615, MK-571, LY-171883, Ro 24-5913 and L-648051; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; $A_{2A}$ agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; and A2B antagonists such as those described in WO 02/42298.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285; and beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 00/75114, which document is incorporated herein by reference, preferably compounds of the Examples thereof, e.g. (5-[(R)-2-(5,6-Diethyl-indan-2-ylamino)-1-hydroxy-ethyl]-8-hydroxy-1H-quinolin-2-one) and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP1460064, WO 04/087142, WO 04/089892, EP 01477167, US 2004/0242622, US 2004/0229904, WO 04/108675, WO 04/108676, WO 05/033121, WO 05/040103 and WO 05/044787.

Suitable dual anti-inflammatory and bronchodilatory drugs include dual beta-2 adrenoceptor agonist/muscarinic antagonists such as those disclosed in US 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841.

Combinations of therapeutic agents of the invention and anticholinergic or antimuscarinic agents, steroids, beta-2 agonists, PDE4 inhibitors, dopamine receptor agonists, LTD4 antagonists or LTB4 antagonists may also be used. Other useful combinations of agents of the invention with anti-inflammatory drugs are those with other antagonists of chemokine receptors, e.g. CCR-1, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]-tetrahydro-N,N-dimethyl-2H-pyran-4-aminium chloride (TAK-770), CCR-5 antagonists described in U.S. Pat. No. 6,166,037 (particularly claims 18 and 19), WO 0066558 (particularly claim 8), WO 0066559 (particularly claim 9), WO 04/018425 and WO 04/026873.

The additional therapeutic agent may also be selected from the group consisting of other cytokine binding molecules, particularly antibodies of other cytokines, in particular a combination with an anti-IL4 antibody, such as described in PCT/EP2005/00836, an anti-IgE antibody, such as Xolair®, an anti-IL31 antibody, an anti-IL31R antibody, an anti-IL13 antibody, such as described in WO05/007699, an anti-endoglin antibody, an anti-IL1b antibody, an anti-TSLPR antibody or another anti-hTSLP antibody.

In a certain embodiment, the invention provides an antibody having a first amino acid sequence which is a heavy chain selected from one to three of SEQ ID NOs: 1-31, and a sequence having at least 60, 70, 80, 90 or 95 percent sequence identity in the CDR regions with the CDR regions having SEQ ID NOs: 1-31; and a second amino acid sequence which is a light chain selected from one to three of SEQ ID NOs: 32-66, and a sequence having at least 60, 70, 80, 90 or 95 percent sequence identity in the CDR regions with the CDR regions shown in SEQ ID NOs: 32-66.

In still another embodiment, the invention provides an immunoconjugate made out of a first component which is an antibody or fragment thereof and a second component having a second amino acid sequence. For example, the immunoconjugate is a cytotoxin, or the immunoconjugate is a binding protein or antibody having a binding specificity for a target that is different from hTSLP.

In certain embodiments, the invention provides for a bispecific antibody.

In another embodiment, the invention provides a kit having an antibody or antibody fragment thereof. In some embodiments, the kit further contains a pharmaceutically acceptable carrier or excipient therefore. In other related embodiments, the antibody in the kit is present in a unit dose. In yet another related embodiment, the kit includes instructions for use in administering to a subject.

DETAILED DESCRIPTION OF THE INVENTION

Figure 1:
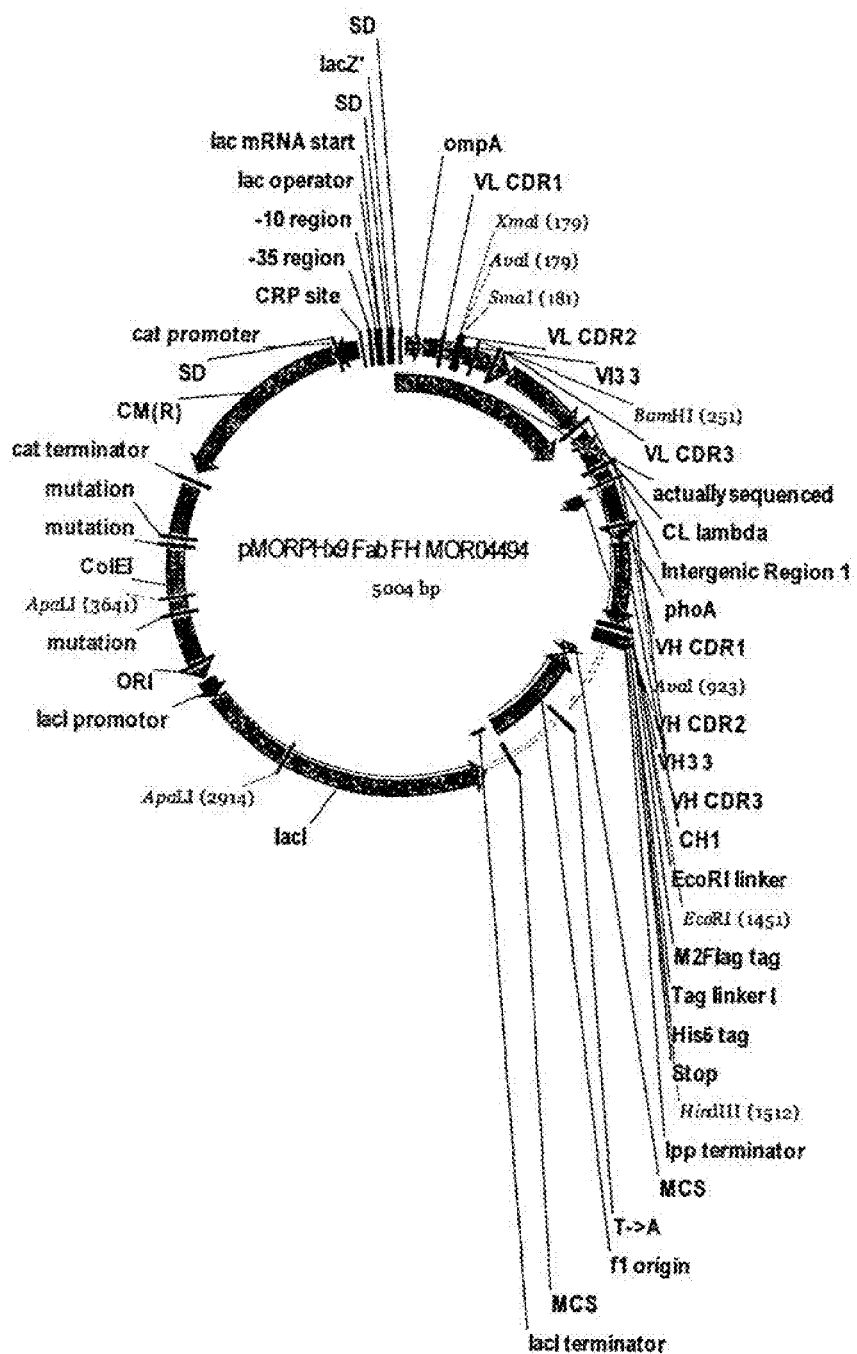
FIG. 1 describes the HuCAL® Fab expression vector pMORPH® X9_Fab_FH (carrying anti-TSLP Fab MOR04494)F

The present invention relates to isolated antibodies, particularly human antibodies, that bind specifically to hTSLP and that inhibit functional properties of hTSLP. In certain embodiments, the antibodies of the invention are derived from particular heavy and light chain sequences and/or comprise particular structural features such as CDR regions comprising particular amino acid sequences. The invention provides isolated antibodies, methods of making such antibodies, immunoconjugates and bispecific molecules comprising such antibodies and pharmaceutical compositions containing the antibodies, immunoconjugates or bispecific molecules of the invention. The invention also relates to methods of using the antibodies to inhibit a disorder or condition associated with the presence of cell receptor target hTSLP, for example, in the treatment of an inflammatory or allergic condition, particularly an inflammatory or obstructive airways disease.

In order that the present invention may be more readily understood, certain terms are first defined. Additional definitions are set forth throughout the detailed description.

The term 'hTSLP' is a reference to human TSLP. The present invention provides antibodies to human TSLP, especially human antibodies, that are cross-reactive with non-human primate TSLP, including cynomolgus and rhesus monkey TSLP. Antibodies in accordance with some embodiments of the present invention may recognise a variant truncated isoform of TSLP in which the protein terminates at the alanine at residue 99 resulting in the last 60 amino acids of the C-terminus being deleted and also an single nucleotide polymorphism (SNP) of TSLP in which the cysteine residue at amino acid position 90 is replaced by tyrosine. The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and capable of the transmission of such a signal across the plasma membrane of a cell. An example of a "cell surface receptor" of the present invention is the hTSLP receptor to which the hTSLP protein molecule binds.

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbrebyted herein as $V_H$) and a heavy chain constant region. The heavy chain constant region is comprised of three domains, CH1, CH2 and CH3. Each light chain is comprised of a light chain variable region (abbrebyted herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is, composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antigen portion"), as used herein, refers to one or more fragments of an antibody that retain the ability to specifically bind to an antigen (e.g., hTSLP). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds hTSLP is substantially free of antibodies that specifically bind antigens other than hTSLP). An isolated antibody that specifically binds hTSLP may, however, have cross-reactivity to other antigens, such as TSLP molecules from other species. Moreover, an isolated antibody may be substantially free of other cellular material and/or chemicals. "Isolated antibody" also refers to an antibody to the target that cross-reacts with known homologs/orthologs, as well as antibodies to the target that do not cross react with known homologs/orthologs.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. CDR grafted antibodies, or alternative technology designed to minimize the Human Anti-murine Antibody response (humaneering technology of Kalobios, or humanization technology of PDL). Xoma also has "human engineering" technology; see e.g., U.S. Pat. No. 5,766,886.

The term "human monoclonal antibody" refers to refers to an antibody obtained from a substantially homogeneous population of antibodies that recognizes and binds to a determinant (or epitope) on the antigen. Monoclonal antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgE, IgG such as IgG1, IgG2 or IgG4) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to hTSLP" is intended to refer to an antibody that binds to human TSLP with a $K_D$ of $1 \times 10^{-9}$ M or less. An antibody that "cross-reacts with an antigen other than hTSLP" is intended to refer to an antibody that binds that antigen with a $1 \times 10^{-9}$ M or less. An antibody that "does not cross-react with a particular antigen" is intended to refer to an antibody that binds to that antigen, with a $K_D$ of $1.5 \times 10^{-8}$ M or greater, or a $K_D$ of $5$-$10 \times 10^{-8}$ M or $1 \times 10^{-7}$ M or greater. In certain embodiments, such antibodies that do not cross-react with the antigen exhibit essentially undetectable binding against these proteins in standard binding assays.

As used herein, an antibody that "inhibits binding of hTSLP to the hTSLP receptor" refers to an antibody that inhibits hTSLP binding to the receptor with a $K_D$ of 5 nM or less.

As used herein, an antibody that "inhibits inflammatory mediator release" is intended to refer to an antibody that inhibits hTSLP induced luciferase expression from a Baf-3 cell line transfected with the TSLP-receptor and a luciferase reporter system and hTSLP induced TARC secretion from human primary monocytes isolated from PBMCs with an $IC_{50}$ less than 1.0 nM.

The term "$K_{assoc}$" or "$K_a$", as used herein, is intended to refer to the association rate of a particular antibody-antigen interaction, whereas the term "$K_{dis}$" or "$K_D$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "high affinity" for an IgG antibody refers to an antibody having a $K_D$ of $10^{-9}$ M or less for a target antigen.

As used herein, the term "subject" includes any human or nonhuman animal.

The term "nonhuman animal" includes all vertebrates, e.g., mammals and non-mammals, such as nonhuman primates, sheep, dogs, cats, horses, cows chickens, amphibians, reptiles, etc.

Various aspects of the invention are described in further detail in the following subsections.

Standard assays to evaluate the binding ability of the antibodies toward hTSLP of various species are known in the art, including for example, ELISAs, western blots and RIAs. Suitable assays are described in detail in the Examples. The binding kinetics (e.g., binding affinity) of the antibodies also can be assessed by standard assays known in the art, such as by Biacore analysis. Assays to evaluate the effects of the antibodies on functional properties of hTSLP are described in further detail in the Examples.

Accordingly, an antibody that "inhibits" one or more of these hTSLP functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). An antibody that inhibits hTSLP activity effects such a statistically significant decrease by at least 10% of the measured parameter, by at least 50%, 80% or 90%, and in certain embodiments an antibody of the invention may inhibit greater than 95%, 98% or 99% of hTSLP functional activity.

Monoclonal Antibodies

Antibodies of the invention are the human monoclonal antibodies, isolated and structurally characterized as described, in Examples 1-5. The $V_H$ amino acid sequences of the antibodies are shown in SEQ ID NOs: 1-31 respectively. The $V_L$ amino acid sequences of the antibodies are shown in SEQ ID NOs: 32-66 respectively. Other antibodies of the invention include amino acids that have been mutated, yet have at least 60, 70, 80, 90 or 95 percent identity in the CDR regions with the CDR regions depicted in the sequences described above.

Since each of these antibodies can bind to hTSLP, the $V_H$ and $V_L$ sequences can be "mixed and matched" to create other anti-hTSLP binding molecules of the invention. hTSLP binding of such "mixed and matched" antibodies can be tested using the binding assays described above and in the Examples (e.g., ELISAs). When $V_H$ and $V_L$ chains are mixed and matched, a $V_H$ sequence from a particular $V_H/V_L$ pairing should be replaced with a structurally similar $V_H$ sequence. Likewise, a $V_L$ sequence from a particular $V_H/V_L$ pairing should be replaced with a structurally similar $V_L$ sequence. The $V_H$ and $V_L$ sequences of the antibodies of the present invention are particularly amenable for mixing and matching, since these antibodies use $V_H$ and $V_L$ sequences derived from the same germline sequences and thus exhibit structural similarity.

In another aspect, the invention provides antibodies that comprise the heavy chain and light chain CDR1s, CDR2s and CDR3s of the antibodies, or combinations thereof. The amino acid sequences of the $V_H$ CDR1s of the antibodies are shown in SEQ ID NOs: 1-7. The amino acid sequences of the $V_H$ CDR2s of the antibodies and are shown in SEQ ID NOs: 8-25. The amino acid sequences of the $V_H$ CDR3s of the antibodies are shown in SEQ ID NOs: 26-31. The amino acid sequences of the $V_L$ CDR1s of the antibodies are shown in SEQ ID NOs: 32-40. The amino acid sequences of the $V_L$ CDR2s of the antibodies are shown in SEQ ID NOs: 41-49. The amino acid sequences of the $V_L$ CDR3s of the antibodies are shown in SEQ ID NOs: 50-66. The CDR regions are delineated using the Kabat system (Kabat, E. A., et al., 1991 Sequences of Proteins of Immunological Interest, Fifth Edition, U.S. Department of Health and Human Services, NIH Publication No. 91-3242).

Given that each of these antibodies can bind to hTSLP and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and match, although each antibody must contain a $V_H$ CDR1, 2 and 3 and a $V_L$ CDR1, 2 and 3) to create other anti-hTSLP binding molecules of the invention. hTSLP binding of such "mixed and matched" antibodies can be tested using the binding assays described above and in the Examples (e.g., ELISAs). When $V_H$ CDR sequences are mixed and matched, the CDR1, CDR2 and/or CDR3 sequence from a particular $V_H$ sequence should be replaced with a structurally similar CDR sequence(s). Likewise, when $V_L$ CDR sequences are mixed and matched, the CDR1, CDR2 and/or CDR3 sequence from a particular $V_L$ sequence should be replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences shown herein for monoclonal antibodies of the present invention.

An isolated monoclonal antibody, or antigen binding portion thereof has: a heavy chain variable region CDR1 comprising an amino acid sequence selected from the group consisting of SEQ ID NOs: 1-7; a heavy chain variable region CDR2 comprising an amino acid sequence selected from the group consisting of SEQ ID NOs: 8-25; a heavy chain variable region CDR3 comprising an amino acid sequence selected from the group consisting of SEQ ID NOs: 26-31; a light chain variable region CDR1 comprising an amino acid sequence selected from the group consisting of SEQ ID NOs: 32-40; a light chain variable region CDR2 comprising an amino acid sequence selected from the group consisting of SEQ ID NOs: 41-49; and a light chain variable region CDR3 comprising an amino acid sequence selected from the group consisting of SEQ ID NOs: 50-66; wherein the antibody specifically binds hTSLP.

In a certain embodiment, the antibody consists of: a heavy chain variable region CDR1 comprising SEQ ID NO: 3; a heavy chain variable region CDR2 comprising SEQ ID NO: 15; a heavy chain variable region CDR3 comprising SEQ ID NO: 28; a light chain variable region CDR1 comprising SEQ ID NO: 38; a light chain variable region CDR2 comprising SEQ ID NO: 47; and a light chain variable region CDR3 comprising SEQ ID NO: 60.

In another embodiment, the antibody consists of: a heavy chain variable region CDR1 comprising SEQ ID NO: 3; a heavy chain variable region CDR2 comprising SEQ ID NO: 17; a heavy chain variable region CDR3 comprising SEQ ID NO: 28; a light chain variable region CDR1 comprising SEQ ID NO: 38; a light chain variable region CDR2 comprising SEQ ID NO: 47; and a light chain variable region CDR3 comprising SEQ ID NO: 60.

In yet another embodiment, the antibody consists of: a heavy chain variable region CDR1 comprising SEQ ID NO: 3; a heavy chain variable region CDR2 comprising SEQ ID NO: 18; a heavy chain variable region CDR3 comprising SEQ ID NO: 28; a light chain variable region CDR1 comprising SEQ ID NO: 38; a light chain variable region CDR2 comprising SEQ ID NO: 47; and a light chain variable region CDR3 comprising SEQ ID NO: 60.

In another embodiment, the antibody consists of: a heavy chain variable region CDR1 comprising SEQ ID NO: 3; a heavy chain variable region CDR2 comprising SEQ ID NO: 19; a heavy chain variable region CDR3 comprising SEQ ID NO: 28; a light chain variable region CDR1 comprising SEQ ID NO: 38; a light chain variable region CDR2 comprising SEQ ID NO: 47; and a light chain variable region CDR3 comprising SEQ ID NO: 60.

In another embodiment, the antibody consists of: a heavy chain variable region CDR1 comprising SEQ ID NO: 3; a heavy chain variable region CDR2 comprising SEQ ID NO: 20; a heavy chain variable region CDR3 comprising SEQ ID NO: 28; a light chain variable region CDR1 comprising SEQ ID NO: 38; a light chain variable region CDR2 comprising SEQ ID NO: 47; and a light chain variable region CDR3 comprising SEQ ID NO: 60.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention has heavy and light chain variable regions having amino acid sequences that are homologous to the amino acid sequences of the antibodies described herein, and wherein the antibodies retain the desired functional properties of the anti-hTSLP antibodies of the Invention.

For example, the invention provides an isolated monoclonal antibody, or antigen binding portion thereof, comprising a heavy chain variable region and a light chain variable region, wherein: the heavy chain variable region comprises an amino acid sequence that is at least 80% homologous to an amino acid sequence selected from the group consisting of SEQ ID NOs: 1-31; the light chain variable region comprises an amino acid sequence that is at least 80% homologous to an amino acid sequence selected from the group consisting of SEQ ID NOs: 32-66; the antibody specifically binds to hTSLP, and the antibody exhibits at least one of the following functional properties: the antibody inhibits binding hTSLP protein to the hTSLP receptor or the antibody inhibits hTSLP receptor binding preventing or ameliorating an inflammatory or allergic condition, particularly an inflammatory or obstructive airways disease, or the antibody inhibits hTSLP receptor binding preventing or ameliorating asthma or the antibody inhibits hTSLP receptor binding preventing or ameliorating COPD.

In various embodiments, the antibody may exhibit one or more, two or more, or three of the functional properties discussed above. The antibody can be, for example, a human antibody, a humanized antibody or a chimeric antibody.

In other embodiments, the $V_H$ and/or $V_L$ amino acid sequences may be 60%, 70%, 80%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of SEQ ID NOs: 1-31 and 32-66 respectively, can be obtained by mutagenesis (e.g., site-directed or PCR-mediated mutagenesis) of nucleic acid molecules encoding SEQ ID NOs: 1-31 and/or 32-66, followed by testing of the encoded altered antibody for retained function (i.e., the functions set forth above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970)

algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al., 1990 J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., 1997 Nucleic Acids Res. 25(17):3389-3402. When utilizing BLAST and Gapped BLAST programs, the default parameters of the respective programs (e.g., XBLAST and NBLAST) can be used.

Antibodies with Conservative Modifications

In certain embodiments, an antibody of the invention has a heavy chain variable region consist of CDR1, CDR2, and CDR3 sequences and a light chain variable region consisting of CDR1, CDR2, and CDR3 sequences, wherein one or more of these CDR sequences have specified amino acid sequences based on the antibodies described herein or conservative modifications thereof, and wherein the antibodies retain the desired functional properties of the anti-hTSLP antibodies of the invention. Accordingly, the invention provides an isolated monoclonal antibody, or antigen binding portion thereof, consisting of a heavy chain variable region consisting of CDR1, CDR2, and CDR3 sequences and a light chain variable region consisting of CDR1, CDR2, and CDR3 sequences, wherein: the heavy chain variable regions of CDR1 is sequences consisting of amino acid sequences selected from the group consisting of amino acid sequences of SEQ ID NOs: 1-7, and conservative modifications thereof; the heavy chain variable region of CDR2 is sequences consisting of amino acid sequences selected from the group consisting of amino acid sequences of SEQ ID NOs: 8-25, and conservative modifications thereof; the heavy chain variable region of CDR3 is sequences consisting of amino acid sequences selected from the group consisting of amino acid sequences of SEQ ID NOs: 26-31, and conservative modifications thereof; the light chain variable regions of CDR1 is sequences consisting of amino acid sequences selected from the group consisting of amino acid sequences of SEQ ID NOs: 32-40, and conservative modifications thereof; the light chain variable regions of CDR2 is sequences consisting of amino acid sequences selected from the group consisting of amino acid sequences of SEQ ID NOs: 41-49, and conservative modifications thereof; the light chain variable regions of CDR3 is sequences consisting of amino acid sequences selected from the group consisting of amino acid sequences of SEQ ID NOs: 50-66, and conservative modifications thereof; the antibody specifically binds to hTSLP; and the antibody inhibits hTSLP receptor binding preventing inflammatory mediator release.

In various embodiments, the antibody may exhibit one or more, two or more, or three or more of the functional properties listed discussed above. Such antibodies can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Antibodies that Bind to the Same Epitope as Anti-HTSLP Antibodies of the Invention In another embodiment, the invention provides antibodies that bind to the same epitope as do the various anti-hTSLP antibodies of the invention provided herein. Such additional antibodies can be identified based on their ability to cross-compete (e.g., to competitively inhibit the binding of, in a statistically significant manner) with other antibodies of the invention in standard hTSLP binding assays. The ability of a test antibody to inhibit the binding of antibodies of the present invention to human hTSLP demonstrates that the test antibody can compete with that antibody for binding to hTSLP; such an antibody may, according to non-limiting theory, bind to the same or a related (e.g., a structurally similar or spatially proximal) epitope on hTSLP as the antibody with which it competes. In a certain embodiment, the antibody that binds to the same epitope on hTSLP as the antibodies of the present invention is a human monoclonal antibody. Such human monoclonal antibodies can be prepared and isolated as described in the Examples.

Engineered and Modified Antibodies

An antibody of the invention further can be prepared using an antibody having one or more of the $V_H$ and/or $V_L$ sequences shown herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad. See. U.S.A. 86:10029-10033; U.S. Pat. No. 5,225,539 to winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1 sequences having an amino acid sequence selected from the group consisting of SEQ ID NOs: 1-7; CDR2 sequences having an amino acid sequence selected from the group consisting of SEQ ID NOs: 8-25; CDR3 sequences having an amino acid sequence selected from the group consisting of SEQ ID NOs: 26-31, respectively; and a light chain variable region having CDR1 sequences having an amino acid sequence selected from the group consisting of SEQ ID NOs: 32-40; CDR2 sequences having an amino acid sequence selected from the group consisting of SEQ ID NOs: 41-49; and CDR3 sequences consisting of an amino acid sequence selected from the group consisting of SEQ ID NOs: 50-66, respectively. Thus, such antibodies contain the $V_H$ and $V_L$ CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database, as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227: 776-798; and Cox, J. P. L. et al., 1994 Eur. J. Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated anti-hTSLP monoclonal antibodies, or antigen binding portions thereof, consisting of a heavy chain variable region having: a $V_H$ CDR1 region consisting of an amino acid sequence selected from the group having SEQ ID NOs: 1-7 or an amino acid sequence having one, two, three, four or five amino acid substitutions, deletions or additions as compared to SEQ ID NOs: 1-7; a $V_H$ CDR2 region having an amino acid sequence selected from the group consisting of SEQ ID NOs: 8-25, or an amino acid sequence having one, two, three, four or five amino acid substitutions, deletions or additions as compared to SEQ ID NOs: 8-25; a $V_H$ CDR3 region having an amino acid sequence selected from the group consisting of SEQ ID NOs: 26-31, or an amino acid sequence having one, two, three, four or five amino acid substitutions, deletions or additions as compared to SEQ ID NOs: 26-31; a $V_L$ CDR1 region having an amino acid sequence selected from the group consisting of SEQ ID NOs: 32-40, or an amino acid sequence having one, two, three, four or five amino acid substitutions, deletions or additions as compared to SEQ ID NOs: 32-40; a $V_L$ CDR2 region having an amino acid sequence selected from the group consisting of SEQ ID NOs: 41-49, or an amino acid sequence having one, two, three, four or five amino acid substitutions, deletions or additions as compared to SEQ ID NOs: 41-49; and a $V_L$ CDR3 region having an amino acid sequence selected from the group consisting of SEQ ID NOs: 50-66, or an amino acid sequence having one, two, three, four or five amino acid substitutions, deletions or additions as compared to SEQ ID NOs: 50-66.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell—epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $CH_2$—CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or $C_L$ region to contain a salvage receptor binding epitope taken from two loops of a CH2 domain of an Fc region of an IgG, as described in U.S. Pat. Nos. 5,869,046 and 6,121,022 by Presta et al. The Fc constant region of an antibody is critical for determining serum half-life and effector functions, i.e., antibody dependent cell cytotoxicity (ADCC) or complement dependent cytotoxicity (CDC) activities. One can engineer specific mutants of the Fc fragment to alter the effector function and/or serum half-life (see Xencor technology for example) (See e.g., WO2004029207).

One method to alter effector function and serum half-life of an antibody is to graft the variable region of an antibody fragment with an Fc fragment having the appropriate effector function. IgG1 or IgG4 isotypes can be selected for cell killing activity, whereas IgG2 isotype can be used for silent antibodies (with no cell killing activity).

Silent antibodies with long serum half-life can be obtained by making chimeric fusion of variable regions of an antibody with a serum protein such as HSA or a protein binding to such serum protein, such HSA-binding protein.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (Gn-TIII)) such that antibodies expressed in the engineered cell lines exhibit increased bisecting GlcNac structures which results in increased ADCC activity of the antibodies (see also Umana et al., 1999 Nat. Biotech. 17:176-180).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivative other proteins, such as mono(C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Effector functions can also be altered by modulating the glycosylation pattern of the antibody. Glycart (e.g., U.S. Pat. No. 6,602,684), Biowa (e.g., U.S. Pat. No. 6,946,292) and Genentech (e.g WO03/035835) have engineered mammalian cell lines to produce antibodies with increased or decreased effector function. Especially, non fucosylated antibodies will have enhanced ADCC activities. Glycofi has also developed yeast cell lines capable of producing specific glycofomms of antibodies. Also Kyowa Hakka/Biowa technology to reduce fucose. See, e.g., WO 03/085102.

A wide variety of antibody/immunoglobulin frameworks or scaffolds can be employed so long as the resulting polypeptide includes one or more binding region which is specific for the hTSLP protein. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

Alternatively, known or future non-immunoglobulin frameworks and scaffolds may be employed, as long as they comprise a binding region specific for the hTSLP protein. Such compounds are known herein as "polypeptides comprising a cMAC-specific binding region". Known non-immunoglobulin frameworks or scaffolds include Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immuno-pharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany).

According to the instant invention, the anti-hTSLP antibody or fragment thereof, or the polypeptide comprising a hTSLP-specific binding region, regardless of the framework or scaffold employed, may be bound, either covalently or non-covalently, to an additional moiety. The additional moiety may be a polypeptide, an inert polymer such as PEG, small molecule, radioisotope, metal, ion, nucleic acid or other type of biologically relevant molecule. Such a construct, which may be known as an immunoconjugate, immunotoxin, or the like, is also included in the meaning of antibody, antibody fragment or polypeptide comprising ahTSLP-specific binding region, as used herein.

Methods of Engineering Antibodies

As discussed above, the anti-hTSLP antibodies having $V_H$ and $V_L$ sequences shown herein can be used to create new anti-hTSLP antibodies by modifying the $V_H$ and/or $V_L$ sequences, or the constant region(s) attached thereto. Thus, in another aspect of the invention, the structural features of an anti-hTSLP antibody of the invention are used to create structurally related anti-hTSLP antibodies that retain at least one functional property of the antibodies of the invention, such as binding to hTSLP and also inhibiting one or more functional properties of hTSLP (e.g., receptor binding, inhibition of mediator release).

For example, one or more CDR regions of the antibodies of the present invention, or mutations thereof, can be combined recombinantly with known framework regions and/or other CDRs to create additional, recombinantly-engineered, anti-hTSLP antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-hTSLP antibody consisting of: a heavy chain variable region antibody sequence having a CDR1 sequence selected from the group consisting of SEQ ID NOs: 1-7, a CDR2 sequence selected from the group consisting of SEQ ID NOs: 8-25 and/or a CDR3 sequence selected from the group consisting of SEQ ID NOs: 26-31 and a light chain variable region antibody sequence having a CDR1 sequence selected from the group consisting of SEQ ID NOs: 32-40, a CDR2 sequence selected from the group consisting of SEQ ID NOs: 41-49 and/or a CDR3 sequence selected from the group consisting of SEQ ID NOs: 50-66; altering at least one amino acid residue within the heavy chain variable region antibody sequence and/or the light chain variable region antibody sequence to create at least one altered antibody sequence; and expressing the altered antibody sequence as a protein.

Standard molecular biology techniques can be used to prepare and express the altered antibody sequence. The antibody encoded by the altered antibody sequence(s) is one that retains one, some or all of the functional properties of the anti-hTSLP antibodies described herein, which functional properties include, but are not limited to, specifically binding to hTSLP; and the antibody exhibits at least one of the following functional properties: the antibody inhibits binding of hTSLP protein to the hTSLP receptor, or the antibody inhibits hTSLP receptor binding preventing or ameliorating an inflammatory, fibrotic or allergic condition, particularly an inflammatory or obstructive airways disease, or the antibody inhibits hTSLP receptor binding thereby preventing or ameliorating asthma.

The altered antibody may exhibit one or more, two or more, or three or more of the functional properties discussed above.

The functional properties of the altered antibodies can be assessed using standard assays available in the art and/or described herein, such as those set forth in the Examples (e.g., ELISAs).

In certain embodiments of the methods of engineering antibodies of the invention, mutations can be introduced randomly or selectively along all or part of an anti-hTSLP antibody coding sequence and the resulting modified anti-hTSLP antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et al., 1988 Proc. Natl. Acad. Sci. USA 85:5879-5883; McCafferty et al., 1990 Nature 348:552-554).

Production of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known. Monoclonal antibodies can also be produced using a specific hybridoma, which has been deposited in a strain collection.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to.Queen.et al.

In a certain embodiment, the antibodies of the invention are human monoclonal antibodies. Such human monoclonal antibodies directed against hTSLP can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-hTSLP antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-hTSLP antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-hTSLP antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Antibodies obtained from screening of antibody human libraries, (e.g. phage display with Morphosys), from libraries such as HuCal library from Morphosys, affinity maturation technology and further codon optimization sequence technologies can also be used. Affinity maturation can also be used on antibodies made in other ways (e.g., hybridomas).

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13).

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in R. J. Kaufman and P. A. Sharp, 1982 Mol. Biol. 159:601-621, NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Sequences encoding partial or full-length light and heavy chains are expressed by transfecting the expression vector(s) carrying such sequences into a host cell by standard transfection techniques. Typically, eukaryotic host cells are used for expressing antibodies, as antibodies are generally glycoproteins and prokaryotic cells are therefore not appropriate. Mammalian host cells which can be used for expressing the recombinant antibodies include Chinese Hamster Ovary (CHO cells) (including dhfr-CHO cells), NSO myeloma cells, COS cells and SP2 cells. Alternatively, one can use a host cell engineered to produce glycoproteins with mammalian-like glycosylation patterns, including yeast, fungi or plant cell lines. The antibodies can be produced for example in glycoengineered yeast cell lines, including *Pichia, Saccharomyces* or *Kluyveromyces* species, and preferably, *Pichia pastoris* or *Saccharomyces cerevisae* or *Kluyveromyces lactis*, see for example EP1297172B1 (Glycofi). The antibodies can also be produced in glycoengineered plant cell lines, and preferably bryophyte cell lines as described in WO2004057002 (Greenovation). Antibodies are produced by culturing the host cells for a period of time sufficient to allow for expression of the antibody in the host cells or secretion of the antibody into the culture medium. Antibodies are recovered from the culture medium using standard protein purification methods.

Immunoconjugates

In another aspect, the present invention features an anti-hTSLP antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al., 2003 Adv. Drug Deliv. Rev. 55:199-215; Trail, P. A. et al., 2003 Cancer Immunol. Immunother. 52:328-337; Payne, G., 2003 Cancer Cell 3:207-212; Allen, T. M., 2002 Nat. Rev. Cancer 2:750-763; Pastan, I. and Kreitman, R. J., 2002 Curr. Opin. Investig. Drugs 3:1089-1091; Senter, P. D. and Springer, C. J., 2001 Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-hTSLP antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for hTSLP and a second binding specificity for a second target epitope. For example, the second target epitope is an Fc receptor, e.g., human FcγRI (CD64) or a human Fcα receptor (CD89). Therefore, the invention includes bispecific molecules capable of binding both to FcγR, FcαR or FcεR expressing effector cells (e.g., monocytes, macrophages or polymorphonuclear cells (PMNs), and to target cells expressing hTSLP. These bispecific molecules target hTSLP expressing cells to effector cell and trigger Fc receptor-mediated effector cell activities, such as phagocytosis of an hTSLP expressing cells, antibody dependent cell-mediated cytotoxicity (ADCC), cytokine release, or generation of superoxide anion.

Additionally, for the invention in which the bispecific molecule is multi-specific, the molecule can further include a third binding specificity, in addition to an anti-Fc binding specificity and an anti-hTSLP binding specificity. For example, the third binding specificity could be an anti-enhancement factor (EF) portion, e.g., a molecule which binds to a surface protein involved in cytotoxic activity and thereby increases the immune response against the target cell. The "anti-enhancement factor portion" could be an antibody, functional antibody fragment or a ligand that binds to a given molecule, e.g., an antigen or a receptor, and thereby results in an enhancement of the effect of the binding determinants for the Fc receptor or target cell antigen.

The "anti-enhancement factor portion" can bind an Fc receptor or a target cell antigen. Alternatively, the anti-enhancement factor portion could bind to an entity that is different from the entity to which the first and second binding specificities bind. For example, the anti-enhancement factor portion can bind a cytotoxic T-cell (e.g. by CD2, CD3, CD8, CD28, CD4, CD44, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fγ receptor classes: FcγRI (CD64), FcγRII (CD32), and FcγRIII (CD 16). In another embodiment, the Fcγ receptor is a human high affinity FcγRI. The human FcγRI is a 72 kDa molecule, which shows high affinity for monomeric IgG ($10^8$-$10^9$ M$^{-1}$).

The production and characterization of certain anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al., 1995 J. Immunol. 155 (10): 4996-5002 and PCT Publication WO 94/10332. The 1122 antibody producing cell line was deposited at the American Type Culture Collection under the designation HA022CL1 and has the accession no. CRL 11177.

In still other embodiments, the binding specificity for an Fc receptor is provided by an antibody that binds to a human IgA receptor, e.g., an Fc-alpha receptor (FcαRI (CD89), the binding of which does not have to be blocked by human immunoglobulin A (IgA). The term "IgA receptor" is intended to include the gene product of one a gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($5 \times 10^7$ $M^{-1}$) for both IgA1 and IgA2, which is increased upon exposure to cytokines such as G-CSF or GM-CSF (Morton, H. C. et al., 1996 Critical Reviews in Immunology 116:423-440). Four FcαRI-specific monoclonal antibodies, identified as A3, A59, A62 and A77, which bind FcαRI outside the IgA ligand binding domain, have been described (Monteiro, R. C. et al., 1992 J. Immunol. 148: 1764).

FcαRI and FcγRI are trigger receptors for use in the bispecific molecules of the invention because they are expressed primarily on immune effector cells, e.g., monocytes, PMNs, macrophages and dendritic cells; expressed at high levels (e.g., 5,000-100,000 per cell); mediators of cytotoxic activities (e.g., ADCC, phagocytosis); mediate enhanced antigen presentation of antigens, including self-antigens, targeted to them.

Other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-hTSLP binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively 4 labeled and used in a radioimmunoassay (RIA) (see, for example, Weintraub; B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Non-Immunoglobulin Scaffolds

A wide variety of antibody/immunoglobulin frameworks or scaffolds can be employed so long as the resulting polypeptide includes at least one binding region which is specific for the target protein. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target protein. Such compounds are known herein as "polypeptides comprising a target-specific binding region". Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immuno-pharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany).

(i) Adnectins—Compound Therapeutics

The adnectin scaffolds are based on fibronectin type III domain (e.g., the tenth module of the fibronectin type III (10 Fn3 domain). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands. (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

(ii) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, 20040175756; 20050053973; 20050048512; and 20060008844.

(vi) Protein A-Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies, they have a molecular weight of 6 kDa, compared to the molecular weight of antibodies, which is 150 kDa. In spite of its small size, the binding site of Affibody® molecules is similar to that of an antibody.

(v) Anticalins—Pieris

Anticalins® are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of Pieris Brassicae has been used to develop anticalins by mutagenizing the set of four loops. One example of a patent application describing "anticalins" is PCT WO 199916873.

(vi) Affilin-Scil Proteins

Affilin™ molecules are small non-immunoglobulin proteins which are designed for specific affinities towards proteins and small molecules. New Affilin™ molecules can be very quickly selected from two libraries, each of which is based on a different human derived scaffold protein.

Affilin™ molecules do not show any structural homology to immunoglobulin proteins. Scil Proteins employs two Affilin™ scaffolds, one of which is gamma crystalline, a human structural eye lens protein and the other is "ubiquitin" super-family proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-hTSLP antibody of the present invention combined with at least one other anti-inflammatory agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Dosage regimens for an anti-hTSLP antibody of the invention include 1 mg/kg body weight or 3 mg/kg body weight by intravenous administration, with the antibody being given using one of the following dosing schedules: every four weeks for six dosages, then every three months; every three weeks; 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-hTSLP antibody of the invention can results in a decrease in severity of disease symptoms, an increase in frequency and duration of disease symptom-free periods, or a prevention of impairment or disability due to the disease affliction.

A composition of the present invention can be administered by one or more routes of administration using one or more of a variety of methods known in the art. As will be appreciated by the skilled artisan, the route and/or mode of administration will vary depending upon the desired results. Routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the invention can be administered with a needleless hypodermic injection device, such as the devices shown in U.S. Pat. No. 5,399,163; 5,383,851; 5,312,335; 5,064,413; 4,941,880; 4,790,824 or 4,596,556. Examples of well known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989 J. Cline Pharmacol. 29:685). Exemplary targeting moieties include folate or biotin (see, e.g., U.S. Pat. No. 5,416,016 to Low et al.); mannosides (Umezawa et al., 1988 Biochem. Biophys. Res. Commun. 153:1038); antibodies (P. G. Bloeman et al., 1995 FEBS Lett. 357:140; M. Owais et al., 1995 Antimicrob. Agents Chemother. 39:180); surfactant protein A receptor (Briscoe et al., 1995 Am. J. Physiol. 1233:134); p 120 (Schreier et al., 1994 J. Biol. Chem. 269:9090); see also K. Keinanen; M. L. Laukkanen, 1994 FEBS Lett. 346:123; J. J. Killion; I. J. Fidler, 1994 Immunomethods 4:273.

Uses and Methods of the Invention

The antibodies (and immunoconjugates and bispecific molecules) of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders. The term "subject" as used herein in intended to include human and non-human animals. Non-human animals includes all vertebrates, e.g., mammals and non-mammals, such as non-human primates, sheep, dogs, cats, cows, horses, chickens, amphibians, and reptiles. The methods are particularly suitable for treating human patients having a disorder associated with aberrant hTSLP expression. When antibodies to hTSLP are administered together with another agent, the two can be administered in either order or simultaneously.

In one embodiment, the antibodies (and immunoconjugates and bispecific molecules) of the invention can be used to detect levels of hTSLP, or levels of cells that contain hTSLP. This can be achieved, for example, by contacting a sample (such as an in vitro sample) and a control sample with the anti-hTSLP antibody under conditions that allow for the formation of a complex between the antibody and hTSLP. Any complexes formed between the antibody and hTSLP are detected and compared in the sample and the control. For example, standard detection methods, well known in the art, such as ELISA and flow cytometic assays, can be performed using the compositions of the invention.

Accordingly, in one aspect, the invention further provides methods for detecting the presence of hTSLP (e.g., hTSLP antigen) in a sample, or measuring the amount of hTSLP, comprising contacting the sample, and a control sample, with an antibody of the invention, or an antigen binding portion thereof, which specifically binds to hTSLP, under conditions that allow for formation of a complex between the antibody or portion thereof and hTSLP. The formation of a complex is then detected, wherein a difference in complex formation between the sample compared to the control sample is indicative of the presence of hTSLP in the sample.

Also within the scope of the invention are kits consisting of the compositions (e.g., antibodies, human antibodies, immunoconjugates and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

The invention having been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications, cited throughout this application are hereby incorporated by reference.

The following examples describe monoclonal, in particular human monoclonal, anti-human TSLP antibody that specifically binds to human TSLP and neutralized its biological activity in different cell based assays, including primary human cell assays. The developed antibodies showed extremely high affinity in the low pM range.

EXAMPLES

For the generation of therapeutic antibodies against human TSLP protein, selections with the MorphoSys HuCAL GOLD® phage display library were carried out. HuCAL GOLD® is a Fab library based on the HuCAL® concept[6-8 9], in which all six CDRs are diversified, and which employs the CysDisplay™ technology for linking Fab fragments to the phage surface[10].

Example 1

Generation of Human TSLP-Specific Antibodies from the HuCAL GOLD® Library

Phagemid Rescue, Phage Amplification, and Purification

The HuCAL GOLD® library was amplified in 2×YT medium containing 34 µg/ml chloramphenicol and 1% glucose (2×YT-CG). After infection with VCSM13 helper phages at an $OD_{600nm}$ of 0.5 (30 min at 37° C. without shaking; 30 min at 37° C. shaking at 250 rpm), cells were spun down (4120 g; 5 min; 4° C.), resuspended in 2×YT/34 µg/ml chloramphenicol/50 µg/ml kanamycin/0.25 mM IPTG and grown overnight at 22° C. Phages were PEG-precipitated twice from the supernatant, resuspended in PBS/20% glycerol and stored at −80° C.

Phage amplification between two panning rounds was conducted as follows: mid-log phase E. coli TG1 cells were infected with eluted phages and plated onto LB-agar supplemented with 1% of glucose and 34 µg/ml of chloramphenicol (LB-CG plates). After overnight incubation at 30° C., the TG1 colonies were scraped off the agar plates and used to inoculate 2×YT-CG until an $OD_{600}$ nm of 0.5 was reached and VCSM13 helper phages added for infection as described above.

Pannings with HuCAL GOLD®

For the selection of antibodies recognizing human TSLP two different panning strategies were applied. In summary, HuCAL GOLD® phage-antibodies were divided into four pools comprising different combinations of $V_H$ master genes (pool 1: VH1/5λκ, pool 2: VH3λκ, pool 3: VH2/4/6λκ, pool 4: VH1-6λκ). These pools were individually subjected to three rounds of solid phase panning on human TSLP directly coated to Maxisorp plates and in addition three of solution pannings on biotinylated TSLP.

The first panning variant was solid phase panning against human TSLP:

2 wells on a Maxisorp plate (F96 Nunc-Immunoplate) were coated with 300 µl of 5 µg/ml TSLP- each o/n at 4° C. The coated wells were washed 2× with 350 µl PBS and blocked with 350 µl 5% MPBS for 2 h at RT on a microtiter plate shaker. For each panning about $10^{13}$ HuCAL GOLD® phage-antibodies were blocked with equal volume of PBST/5% MP for 2 h at room temperature. The coated wells were washed 2× with 350111 PBS after the blocking. 300 µl of pre-blocked HuCAL GOLD® phage-antibodies were added to each coated well and incubated for 2 h at RT on a shaker. Washing was performed by adding five times 350 µl PBS/0.05% Tween, followed by washing another four times with PBS. Elution of phage from the plate was performed with 300 µl 20 mM DTT in 10 mM Tris/HCl pH8 per well for 10 min. The DTT phage eluate was added to 14 ml of E. coli TG1, which were grown to an $OD_{600}$ of 0.6-0.8 at 37° C. in 2YT medium and incubated in 50 ml plastic tubes for 45 min at 37° C. without shaking for phage infection. After centrifugation for 10 min at 5000 rpm, the bacterial pellets were each resuspended in 500 µl 2×YT medium, plated on 2×YT-CG agar plates and incubated overnight at 30° C. Colonies were then scraped from the plates and phages were rescued and amplified as described above. The second and third rounds of the solid phase panning on directly coated TSLP was performed according to the protocol of the first round except for increasing the stringency of the washing procedure.

The second panning variant was solution panning against biotinylated human TSLP:

For the solution panning, using biotinylated TSLP coupled to Dynabeads M-280 (Dynal), the following protocol was applied: 1.5 ml Eppendorf tubes were blocked with 1.5 ml 2× Chemiblocker diluted 1:1 with PBS over night at 4° C. 200 µl streptavidin coated magnetic Dynabeads M-280 (Dynal) were washed 1× with 200 µl PBS and resuspended in 200 µl 1× Chemiblocker (diluted in 1×PBS). Blocking of beads was performed in pre-blocked tubes over night at 4° C. Phages diluted in 500111 PBS for each panning condition were mixed with 500 µl 12× Chemiblocker/0.1% Tween 1 h at RT (rotator). Pre-adsorption of phages was performed twice: 50 µl of blocked Streptavidin magnetic beads were added to the blocked phages and incubated for 30 min at RT on a rotator. After separation of beads via a magnetic device (Dynal MPC-E) the phage supernatant (~1 ml) was transferred to a new blocked tube and pre-adsorption was repeated on 50 µl blocked beads for 30 min. Then, 200 nM biotinylated hTSLP was added to blocked phages in a new blocked 1.5 ml tube and incubated for 1 h at RT on a rotator. 100 µl of blocked streptavidin magnetic beads were added to each panning phage pool and incubated 10 min at RT on a rotator. Phages bound to biotinylated TSLP were immobilized to the magnetic beads and collected with a magnetic particle separator (Dynal MPC-E). Beads were then washed 7× in PBS/0.05% Tween using a rotator, followed by washing another three times with PBS. Elution of phage from the Dynabeads was performed adding 300 µl 20 mM DTT in 10 mM Tris/HCl pH 8 to each tube for 10 min. Dynabeads were removed by the magnetic particle separator and the supernatant was added to 14 ml of an E. coli TG-1 culture grown to $OD_{600nm}$ of 0.6-0.8. Beads were then washed once with 200 µl PBS and together with additionally removed phages the PBS was added to the 14 ml E. coli TG-1 culture. For phage infection, the culture was incubated in 50 ml plastic tubes for 45 min at 37° C. without shaking. After centrifugation for 10 min at 5000 rpm, the bacterial pellets were each resuspended in 500 µl 2×YT medium, plated on 2×YT-CG agar plates and incubated overnight at 30° C. Colonies were then scraped from the plates and phages were rescued and amplified as described above.

The second and third rounds of the solution panning on biotinylated TSLP was performed according to the protocol of the first round except for increasing the stringency of the washing procedure.

Subcloning and Expression of Soluble Fab Fragments

The Fab-encoding inserts of the selected HuCAL GOLD® phagemids were sub-cloned into the expression vector pMORPH® X9_Fab_FH (FIG. 1) in order to facilitate rapid and efficient expression of soluble Fabs. For this purpose, the plasmid DNA of the selected clones was digested with XbaI and EcoRI, thereby excising the Fab-encoding insert (ompA-VLCL and phoA-Fd), and cloned into the XbaI/EcoRI-digested expression vector pMORPH® X9_Fab_FH. Fabs expressed from this vector carry two C-terminal tags (FLAG™ and 6×His, respectively) for both, detection and purification.

Microexpression of HuCAL GOLD® Fab Antibodies in E. coli

Chloramphenicol-resistant single colonies obtained after subcloning of the selected Fabs into the pMORPH® X9_Fab_FH expression vector were used to inoculate the wells of a sterile 96-well microtiter plate containing 100 µl 2×YT-CG medium per well and grown overnight at 37° C. 5 µl of each E. coli TG-1 culture was transferred to a fresh, sterile 96-well microtiter plate pre-filled with 100 µl 2×YT medium supplemented with 34 µg/ml chloramphenicol and 0.1% glucose per well. The microtiter plates were incubated at 30° C. shaking at 400 rpm on a microplate shaker until the cultures were slightly turbid (~24 hrs) with an $OD_{600}$ nm of 0.5.

To these expression plates, 20 µl 2×YT medium supplemented with 34 µg/ml chloramphenicol and 3 mM IPTG (isopropyl-β-D-thiogalactopyranoside) was added per well (end concentration 0.5 mM IPTG), the microtiter plates sealed with a gas-permeable tape, and incubated overnight at 30° C. shaking at 400 rpm.

Generation of whole cell lysates (BEL extracts): To each well of the expression plates, 40 µl BEL buffer (2×BBS/EDTA: 24.7 g/l boric acid, 18.7 g NaCl/l, 1.49 g EDTA/l, pH 8.0) was added containing 2.5 mg/ml lysozyme and incubated for 1 h at 22° C. on a microtiter plate shaker (400 rpm). The BEL extracts were used for binding analysis by ELISA or a BioVeris M-Series® 384 analyzer (see Example 2).

Enzyme Linked Immunosorbent Assay (ELISA) Techniques

5 µg/ml of human recombinant TSLP (R&D Systems) in PBS was coated onto 384 well Maxisorp plates (Nunc-Immunoplate) o/n at 4° C. After coating the wells were washed once with PBS/0.05% Tween (PBS-T) and 2× with PBS. Then the wells were blocked with PBS-T with 2% BSA for 2 h at RT. In parallel 15 µl BEL extract and 15 µl PBS-T with 2% BSA were incubated for 2 h at RT. The blocked Maxisorp plated were washed 3× with PBS-T before 10 µl of the blocked BEL extracts were added to the wells and incubated for 1 h at RT. For detection of the primary Fab antibodies, the following secondary antibodies were applied: alkaline phospatase (AP)-conjugated AffiniPure F(ab')$_2$ fragment, goat anti-human, -anti-mouse or -anti-sheep IgG (Jackson Immuno Research). For the detection of AP-conjugates fluorogenic substrates like AttoPhos (Roche) were used according to the instructions by the manufacturer. Between all incubation steps, the wells of the microtiter plate were washed with PBS-T three times and three times after the final incubation with secondary antibody. Fluorescence was measured in a TECAN Spectrafluor plate reader.

Expression of HuCAL GOLD® Fab Antibodies in E. coli and Purification

Expression of Fab fragments encoded by pMORPH® X9_Fab_FH in TG-1 cells was carried out in shaker flask cultures using 750 ml of 2×YT medium supplemented with 34 µg/ml chloramphenicol. Cultures were shaken at 30° C. until the $OD_{600nm}$ reached 0.5. Expression was induced by addition of 0.75 mM IPTG for 20 h at 30° C. Cells were disrupted using lysozyme and Fab fragments isolated by Ni-NTA chromatography (Qiagen, Hilden, Germany). Protein concentrations were determined by UV-spectrophotometry[11].

Example 2

Identification of Neutralizing Anti-Human TSLP Fab Candidates that Inhibit TSLP Induced Signaling of the TSLP Receptor 22 different human TSLP specific antibodies, which were selected from the HuCAL GOLD® library, were tested for the potency to neutralize human TSLP.

A. Blocking of TSLP Binding to the TSLP Receptor by Anti-Human TSLP Fabs in FACS Assay Binding inhibition of biotinylated TSLP to Ba/F3 cells, expressing hTSLPR, hIL7Rα was analyzed by FACS. The Fab antibodies were diluted in FACS buffer (cellwash (B&D)/3% FCS). 50 µl biotinylated TSLP at 100 ng/ml was incubated with 50 µl of 100 µg/ml Fab for 1 h at RT. To avoid internalization of the TSLP receptor all further steps with cells were carried out at 4° C. or on ice. 100 µl Ba/F3 cells at 2×10$^6$ cells/ml were transferred to each well of a 96 well plate (NUNC) and centrifuged at 2000 rpm; 4° C. Cells were washed 2× with 150 µl cold FACS buffer, resuspended with the Fab/biotinylated TSLP mix and incubated for 1 h at 4° C. on a shaker. Streptavidin PE 1:400 in FACS-buffer was added for detection. After 30 min incubation, cells were centrifuged as mentioned above and washed 2× with 150 µl cold FACS buffer. 5000 cells were analyzed in FACS. MOR04494, MOR04496, MOR04497 and MOR04609 showed inhibition of cell binding.

Inhibition of TSLP Dependent STAT5 Activation

Ba/F3 cells, expressing hTSLPR, hIL7Ra and a Stat5-Luc reporter gene, were grown in the presence of 5 ng/ml TSLP. 10 µl of 1×10$^6$ cells/ml in assay buffer (RPMI-1640 w/o phenol red, 10% FCS, penicillin 10 Uml$^{-1}$/streptomycin 10 µgml$^{-1}$, 1% puromycin) were added to Costar 96-well white plate (Corning). 70 µl of assay buffer and 10 µl of anti-TSLP antibody (10×) in assay buffer was added and incubated for 20 min at 37° C. 10 µl of 5 ng/ml TSLP (R&D Systems; 0.5 ng/ml final concentration) in assay buffer was added to give a final assay volume of 100 µl. The plate was covered and left for 5-6 h at 37° C. in a humidified incubator. To the wells 100 µl (1:1 with assay volume) of Bright-Glo™ luciferase (Promega) were added and incubated for 5 min at RT. The plate was sealed with TopSeal™ before recording luminescence. MOR04493, MOR04494, MOR04496, MOR04497 and MOR04609 neutralized TSLP in this assay.

Determination of Neutralizing Activity in Primary Monocyte

Isolation of human blood monocytes—150 mL of blood was collected from healthy adult volunteers on the NHRC donor panel. Blood was collected with tubes containing 1 mL of anti-coagulant (20 mg/mL EDTA in PBS) per 10 mL blood and then diluted with 12.5 mL PBS per 20 mL blood. Red blood cells were then sedimented by mixing the diluted blood with 12.5 mL 4% Dextran (in PBS) per tube and incubating for 40 minutes on ice. PBMCs were isolated by density centrifugation using Ficoll and the 'buffy coat' containing PBMCs was recovered using a plastic pastete. The cells were washed once (300×g for 7 minutes) in PBS and counted. MACS isolation of cells was carried out according to the manufacturers instructions using the Monocyte Isolation kit II (Miltenyi Biotec). All buffer additions and washes were with MACS buffer at 4° C. (PBS, 0.5% BSA, 2 mM EDTA, pH 7.2) unless otherwise stated. Briefly, to $10^7$ cells, 30 µL of buffer and 10 µL each of FcR Blocking Reagent and Biotin-Antibody Cocktail were added, mixed well and incubated for 10 minutes. A further 30 µL of buffer and 20 µL of Anti-Biotin Microbeads were then added to the cells and incubated for 15 minutes. Cells were washed (300×g for 10 minutes), resuspended at $10^8$ cells per 500 µL buffer and applied to the 'primed' LS column. The 'untouched' monocyte fraction was collected by retaining all other cell types on the column. During the isolation procedure samples were collected for later analysis by flow cytometry.

TARC production by monocytes treated with TSLP and blocking the response with anti-TSLP antibodies-Freshly isolated monocytes were resuspended at $1\times10^6$ cells per mL of assay buffer (RPMI 1640, 10% FCS, penicillin 10 U/mL/ streptomycin 10 µg/mL). 100 µL of cells were added to each well of a 96-well flat-bottomed plate to give a concentration of 100,000 cells per well. 80 µL of assay buffer was added to wells that were used for the TSLP dose response curve and 60 µL was added to wells in which anti-TSLP antibodies were to be tested. For the anti-TSLP antibody testing, 20 µL of a 10× stock solution of each anti-TSLP antibody was added to the cells and incubated at 37° C., 5% $CO_2$ for 20 minutes. rhTSLP was then added at 0.5 ng/mL to each well (20 µL of 10× stock solution per well) containing anti-TSLP antibody. A TSLP dose response curve was included on each plate. Plates were incubated for 24 hours at 37° C., 5% $CO_2$ after which supernatants were harvested and stored at −20° C. for future analysis.

ELISA of monocyte supernatants to measure TARC—Measurements of TARC production in culture supernatants was carried out using a human TARC duoset ELISA kit (R+D Systems) according to manufacturer's instructions. Briefly monocyte supernatants were diluted 1:2 in assay buffer (RPMI 1640, 10% FCS, penicillin 10 U/mL/streptomycin 10 µg/mL) and added in triplicate to 96-well half-area plates previously coated with TARC capture antibody. Plates were incubated for 2 hours at RT then washed again. 50 µL of biotinylated detection mAb was then added to each well and incubated for a further 2 hours at RT. Plates were washed and horseradish peroxidase was added at 50 µL per well and incubated for 20 minutes at RT in the dark. A final wash was carried out and 100 µL of TMB substrate was added per well and plates were incubated at RT in the dark. Colour development was stopped after 20 minutes incubation by addition of 50 µL 1M sodium hydroxide. Plates were read immediately on a Spectramax microplate reader set at 450 nm (Molecular Devices). Data was analysed using SoftmaxPro software and percentage inhibition of maximal absorbance response by anti-TSLP antibodies was calculated using an Excel spreadsheet.

Neutralization of Natural Human TSLP in Receptor Gene Assay

Human natural TSLP was generated by treating primary human fibroblast cells (Clonetics), with a cytokine cocktail containing IL-1β (1 ng/ml), TNF-α (1 ng/ml) and IL-13 (10 ng/ml) for 24 hours at 37° C. in phenol-red free RPMI containing 10% FBS. The cell culture supernatant containing induced natural TSLP was shown to be active in the RGA described above.

A 1 in 10 dilution of the natural TSLP containing TSLP corresponded to approximately the same level of activity in the RGA as 0.5 ng/ml of rhTSLP and hence was used as the final dilution when testing the activity of candidate antibodies.

TSLP/TSLP Receptor Binding Inhibition BioVeris Assay

For the TSLP binding inhibition assay, recombinant human TSLP (R&D Systems) was directly coupled (NHS/EDC coupling) to carboxylic acid M-270 Dynal magnetic beads. 50 µl Fab antibodies per well (10 µM stock, 1:5 dilution steps) were incubated for 2 h with 25 µl TSLP coated beads in 96 well plates (Nunc). 50 µl of 100 µM TSLP-receptor/Fc fusion and 1:1000 diluted anti-human Fc detection antibody labeled with BV-tag™ according to instructions of supplier (BioVeris, Europe, Witney, Oxforfshire, UK) were added to each well and incubated for 1 h. (Final Fab concentration: 32 nM-4 µM, final TSLP conc: 40 µM). Detection was performed by BioVeris M-384 SERIES® Workstation (BioVeris Europe, Witney, Oxforfshire, UK). MOR04493, MOR04494, MOR04496, MOR04497, MOR04609, and MOR04832 showed inhibition of TSLP receptor binding in this assay.

Determination of Nanomolar Affinities Using Surface Plasmon Resonance (Biacore)

Kinetic SPR analysis was performed on a SA-chip (Biacore, Sweden) which had been coated with a density of ~400 RU biotinylated recombinant human TSLP i. A respective amount of biotinylated human serum albumin (HSA) was immobilized on the reference flow cell. PBS (136 mM NaCl, 2.7 mM KCl, 10 mM Na2HPO4, 1.76 mM KH2PO4 pH 7.4) was used as the running buffer. The Fabs were applied in concentration series of 16-500 nM at a flow rate of 20 µl/min. Association phase was set to 60 s and dissociation phase to 120 s. The summarized affinities of the parental Fab antibodies 4493, 4494, 4496, 4497, 4832 and 4609 to human TSLP determined by that method are in the range of 8-1400 nM.

Example 3

Affinity Maturation of Selected Anti-TSLP Fabs by Parallel Exchange of LCDR3 and HCDR2 Cassettes B. Generation of Fab Libraries for Affinity Maturation In order to increase the affinity and inhibitory activity of the identified anti-TSLP antibodies, 6 Fab clones MOR04493, MOR04494, MOR04496, MOR04497, MOR04609, and MOR04832 were subjected to affinity maturation. For this purpose, CDR regions were optimized by cassette mutagenesis using trinucleotide directed mutagenesis[12,13].

The following paragraph briefly describes the protocol used for cloning of the maturation libraries and Fab optimization. Fab fragments from expression vector pMORPH® X9—Fab_FH were cloned into the phagemid vector pMORPH®25 (U.S. Pat. No. 6,753,136). Two different strategies were applied in parallel to optimize both, the affinity and the efficacy of the parental Fabs.

Six phage antibody Fab libraries were generated where the LCDR3 of six parental clones was replaced by a repertoire of individual light chain CDR3 sequences. In parallel, the HCDR2 region of each parental clone was replaced by a repertoire of individual heavy chain CDR2 sequences. Affinity maturation libraries were generated by standard cloning procedures and transformation of the diversified clones into electro-competent *E. coli* TOP10F' cells (Invitrogen). Fab-presenting phages were prepared as described in Example 1A. Four maturation pools were built and kept separate during the subsequent selection process:

- pool 1: LCDR3 libraries of MOR04493 and MOR04832
- pool 2: HCDR2 libraries of MOR04493 and MOR04832
- pool 3: LCDR3 libraries of MOR04494; MOR04496; MOR04497; MOR04609
- pool 4: HCDR2 libraries of MOR04494; MOR04496; MOR04497; MOR04609

Maturation Panning Strategies

Pannings using the four antibody pools were performed on biotinylated recombinant human TSLP (R&D Systems) in solution for three rounds, respectively as described in Example 1B, solution panning against biotinylated human TSLP. The selection stringency was increased by reduction of biotinylated antigen from panning round to panning round, by prolonged washing steps and by addition of non-biotinylated antigen for off-rate selection.

Electrochemiluminescene (BioVeris) Based Binding Analysis for Detection of TSLP Binding Fab in Bacterial Lysates Binding of optimized Fab antibodies in *E. coli* lysates (BEL extracts) to TSLP was analyzed in BioVeris M-SERIES® 384 AnalyzerBioVeris, Europe, Witney, Oxforfshire, UK). BEL extracts were diluted in assay buffer (PBS/0.05% Tween20/0.5% BSA) for use in BioVeris screening. Biotinylated TSLP (R&D Systems) was coupled to streptavidin coated paramagnetic beads, Anti-human (Fab)'$_2$ (Dianova) was ruthenium labeled using the BV-tag™ (BioVeris Europe, Witney, Oxfordshire, UK). This secondary antibody was added to the TSLP coupled beads before measuring in the BioVeris M-SERIES® 384 Analyzer. After sequence analysis of hits from the BioVeris screening, 20 unique Fab clones were identified: MOR05008; MOR05009; MOR05010; MOR05011; MOR05012; MOR05013; MOR05014; MOR05015; MOR05016; MOR05017; MOR05018; MOR05019; MOR05020; MOR05021; MOR05022; MOR05023; MOR05024; MOR05025; MOR05026; MOR05027.

IgG Conversion and Cross-Transfection of Two Independently Optimized Variable Chains in Order to Further Improve the Affinities of the Antibodies All 20 optimized Fab antibodies were sub-cloned into IgG1 format. Affinity of all 20 IgG1 of MOR05008; MOR05009; MOR05010; MOR05011; MOR05012; MOR05013; MOR05014; MOR05015; MOR05016; MOR05017; MOR05018; MOR05019; MOR05020; MOR05021; MOR05022; MOR05023; MOR05024; MOR05025; MOR05026; MOR05027 was measured in solution equilibrium titration from tissue culture supernatant.

For a further improvement of affinity the independently optimized H-CDR2 and L-CDR3 from matured IgG1s, which were derived from the same parental clone, were combined, because there was a high probability that this combination would lead to a further gain of affinity[14-16]. The heavy and the light chain of the IgG1 were on separate vectors and therefore by cross-transfection it was possible to combine the two different optimized chains which were then co-expressed in one cell and assemble to IgG antibodies. This method was applied for binders that were derived from the parental clone MOR04494 and MOR04497, where from both the H-CDR2 and the L-CDR3 library optimized chains were identified in parallel. For MOR04494 all six optimized heavy chains from MOR05010-MOR05015 were combined one by one with the three optimized light chains of MOR05016-MOR05018 resulting in 18 new antibodies. For MOR04497 the one optimized H-CDR2 of MOR5019 was combined with the three optimized light chains of MOR05020-MOR05022 resulting in 3 new antibodies.

Determination of Picomolar Affinities Using Solution Equilibrium Titration (SET)

For $K_D$ determination, monomer fractions (at least 90% monomer content, analyzed by analytical SEC; Superdex75, Amersham Pharmacia) of Fab were used. In addition it was possible to determine the affinities of IgG1, as the antigen TSLP is supposed to be a monomer in solution. Electrochemiluminescence (ECL) based affinity determination in solution and data evaluation were basically performed as described by Haenel et al., 2005. A constant amount of Fab or IgG1 was equilibrated with different concentrations (serial 3″ dilutions) of recombinant human TSLP (R&D Systems) in solution. Biotinylated human TSLP coupled to paramagnetic beads (M-280 Streptavidin, Dynal), and BV-tag™ (BioVeris Europe, Witney, Oxfordshire, UK) labeled anti-human (Fab)'$_2$ (Dianova) was added and the mixture incubated for 30 min. Subsequently, the concentration of unbound Fab was quantified via ECL detection using the M-SERIES® 384 analyzer (BioVeris Europe).

Affinity determination to cynomolgus TSLP (mammalian expression and purification at NVS) in solution was done essentially as described above replacing the human TSLP by the cynomolgus TSLP. For detection of free Fab, biotinylated human TSLP coupled to paramagnetic beads was used. Affinities were calculated according to Haenel et al. (2005)[17]. Using the assay conditions described above (monomeric) affinities for the affinity-optimized anti-TSLP IgGs were determined in solution. The affinities to human and cynomolgus TSLP are summarized in Table 5.

TABLE 5

Affinities of optimized IgG1.

| VH-/VL pairs for IgG | | IgG MOR0# | rh TSLP KD [pM] | cyno TSLP-APP KD [pM] | Parental binder |
|---|---|---|---|---|---|
| VH | VL | | | | |
| 1 | | 5008 | 10 | 1438 | MOR04493 |
| 2 | | 5009 | 5 | 10861 | |
| 3 | | 4494 | >200 | 20857 | MOR04494 |
| 4 | | 5010 | 2 | 1099 | |
| 5 | | 5011 | 31 | 4951 | |
| 6 | | 5012 | 25 | 1535 | |
| 7 | | 5013 | 34 | 1367 | |
| 8 | | 5014 | 8 | 3711 | |
| 9 | | 5015 | 26 | 2959 | |
| 10 | | 5016 | 7 | 98 | |
| 11 | | 5017 | 4 | 111 | |
| 12 | | 5018 | 14 | 358 | |

TABLE 5-continued

| | | | | | |
|---|---|---|---|---|---|
| 13 | 5010 | 5016 | 5154 | 13 | 18 |
| 14 | 5010 | 5017 | 5155 | 1 | 9 |
| 15 | 5010 | 5018 | 5156 | 16 | 58 |
| 16 | 5011 | 5016 | 5157 | 1 | 34 |
| 17 | 5011 | 5017 | 5158 | 9 | 21 |
| 18 | 5011 | 5018 | 5159 | 12 | 87 |
| 19 | 5012 | 5016 | 5160 | 27 | 28 |
| 20 | 5012 | 5017 | 5161 | 11 | 11 |
| 21 | 5012 | 5018 | 5162 | 21 | 81 |
| 22 | 5013 | 5016 | 5163 | 22 | 17 |
| 23 | 5013 | 5017 | 5164 | 14 | 8 |
| 24 | 5013 | 5018 | 5165 | 19 | 45 |
| 25 | 5014 | 5016 | 5166 | 22 | 27 |
| 26 | 5014 | 5017 | 5167 | 14 | 16 |
| 27 | 5014 | 5018 | 5168 | <1 | 108 |
| 28 | 5015 | 5016 | 5169 | 1 | 53 |
| 29 | 5015 | 5017 | 5170 | 11 | 25 |
| 30 | 5015 | 5018 | 5171 | 29 | 71 |
| 31 | | | 4497 | >200 | >20 nM | MOR04497 |
| 32 | | | 5019 | 36 | 3825 |
| 33 | | | 5020 | 13 | 103 |
| 34 | | | 5021 | 14 | 79 |
| 35 | | | 5022 | 7 | 79 |
| 36 | 5019 | 5020 | 5172 | 122 | 7540 |
| 37 | 5019 | 5021 | 5173 | 39 | 3377 |
| 38 | 5019 | 5022 | 5174 | 117 | 4763 |
| 39 | | | 5023 | 5 | >20 nM | MOR04832 |
| 40 | | | 5024 | 4 | >20 nM |
| 41 | | | 5025 | 7 | >20 nM |
| 42 | | | 5026 | 12 | >20 nM |
| 43 | | | 5027 | 7 | >20 nM |

▨ parental
▨ x-clones

Thus, as a further aspect of the present invention, there is presented the use of an isolated hTSLP-binding region of an antibody or functional fragment thereof having an $K_D$ of less than 100 pM, suitably less than 50 pM, preferably less than 30 pM, in the treatment of a disease associated with the presence of cell receptor target hTSLP, such as asthma or atopic dermatitis.

REFERENCE LIST

1. Reche, P. A. et al. Human thymic stromal lymphopoietin preferentially stimulates myeloid cells. *J Immunol* 167, 336-343 (2001).
2. Soumelis, V. et al. Human epithelial cells trigger dendritic cell mediated allergic inflammation by producing TSLP. *Nat Immunol* 3, 673-680 (2002).
3. Levin, S. D. et al. Thymic stromal lymphopoietin: a cytokine that promotes the development of IgM+ B cells in vitro and signals via a novel mechanism. *J Immunol* 162, 677-683 (1999).
4. Novak, N. & Bieber, T. The role of dendritic cell subtypes in the pathophysiology of atopic dermatitis. *J Am Acad. Dermatol.* 53, S171-S176 (2005).
5. Quentmeier, H. et al. Cloning of human thymic stromal lymphopoietin (TSLP) and signaling mechanisms leading to proliferation. *Leukemia* 15, 1286-1292 (2001).
6. Knappik, A. et al. Fully synthetic human combinatorial antibody libraries (HuCAL) based on modular consensus frameworks and CDRs randomized with trinucleotides. *J Mol Biol* 296, 57-86 (2000).
7. Krebs, B. et al. High-throughput generation and engineering of recombinant human antibodies. *J Immunol Methods* 254, 67-84 (2001).
8. Rauchenberger, R. et al. Human combinatorial Fab library yielding specific and functional antibodies against the human fibroblast growth factor receptor 3. *J Biol Chem* 278, 38194-38205 (2003).
9. Knappik, A. et al. Fully synthetic human combinatorial antibody libraries (HuCAL) based on modular consensus frameworks and CDRs randomized with trinucleotides. *J Mol Biol* 296, 57-86 (2000).
10. Löhning, C. Novel methods for displaying (poly)peptides/proteins on bacteriophage particles via disulfide bonds. (WO 01/05950). 2001.
    Ref Type: Patent
11. Krebs, B. et al. High-throughput generation and engineering of recombinant human antibodies. *J Immunol Methods* 254, 67-84 (2001).
12. Nagy, Z. A. et al. Fully human, HLA-DR-specific monoclonal antibodies efficiently induce programmed death of malignant lymphoid cells. *Nat Med* 8, 801-807 (2002).
13. Virnekas, B. et al. Trinucleotide phosphoramidites: ideal reagents for the synthesis of mixed oligonucleotides for random mutagenesis. *Nucleic Acids Res* 22, 5600-5607 (1994).
14. Chen, Y. et al. Selection and analysis of an optimized anti-VEGF antibody: crystal structure of an affinity-matured Fab in complex with antigen. *J Mol Biol* 293, 865-881 (1999).
15. Schier, R. et al. Isolation of picomolar affinity anti-c-erbB-2 single-chain Fv by molecular evolution of the complementarity determining regions in the center of the antibody binding site. *J Mol Biol* 263, 551-567 (1996).
16. Yang, W. P. et al. CDR walking mutagenesis for the affinity maturation of a potent human anti-HIV-1 antibody into the picomolar range. *J Mol Biol* 254, 392-403 (1995).
17. Haenel, C., Satzger, M., Ducata, D. D., Ostendorp, R. & Brocks, B. Characterization of high-affinity antibodies by electrochemiluminescence-based equilibrium titration. *Anal Biochem* 339, 182-184 (2005).

Annex 1 CDR Sequences Of Antibodies Of The Invention

| Id no. | HCDR 1 | SEQ ID # | HCDR 2 | SEQ ID # | HCDR 3 | SEQ ID # |
|---|---|---|---|---|---|---|
| VH CDR (H-CDR) Sequences | | | | | | |
| VH1A | GGTFSS--YAIS | 1 | GIIP--IFGTANYAQKFQG | 8 | | |
| MOR04493 | GGTFSS--YAIS | 1 | GIIP--DFGWANYAQKFQG | 9 | SGMFYSILFDY---- | 26 |
| MOR05008 | GGTFSS--YAIS | 1 | GIIP--EFGFTNYAQKFQG | 10 | SGMFYSILFDY---- | 26 |
| MOR05009 | GGTFSS--YAIS | 1 | HISP--EFGFTNYAQKFQG | 11 | SGMFYSILFDY---- | 26 |
| MOR04832 | GGTFSS--YAIS | 1 | NIYP--IFGYANYAQKFQG | 12 | YGQYGQHFSHGGMDV | 27 |
| MOR05023 | GGTFSS--YAIS | 1 | NIYP--IFGYANYAQKFQG | 12 | YGQYGQHFSHGGMDV | 27 |
| MOR05024 | GGTFSS--YAIS | 1 | NIYP--IFGYANYAQKFQG | 12 | YGQYGQHFSHGGMDV | 27 |
| MOR05025 | GGTFSS--YAIS | 1 | NIYP--IFGYANYAQKFQG | 12 | YGQYGQHFSHGGMDV | 27 |
| MOR05026 | GGTFSS--YAIS | 1 | NIYP--IFGYANYAQKFQG | 12 | YGQYGQHFSHGGMDV | 27 |
| MOR05027 | GGTFSS--YAIS | 1 | NIYP--IFGYANYAQKFQG | 12 | YGQYGQHFSHGGMDV | 27 |

-continued

Annex 1 CDR Sequences Of Antibodies Of The Invention

| Id | | HCDR 1 | SEQ ID # | HCDR 2 | SEQ ID # | HCDR 3 | SEQ ID # |
|---|---|---|---|---|---|---|---|
| SEQ ID NO | VH3 | GFTFSS--YAMS | 2 | AISG--SGGSTYYADSVKG | 13 | | |
| MOR04494 | | GFTFSS--YYMS | 3 | NISY--DSSDTYYADSVKG | 14 | QQYFDHIDI------ | 28 |
| MOR05010 | | GFTFSS--YYMS | 3 | GIFF---DGETYYAGSVKG | 15 | QQYFDHLDI------ | 28 |
| MOR05011 | | GFTFSS--YYMS | 3 | GIFY---DGSTYYPDSVKG | 16 | QQYFDHIDI------ | 28 |
| MOR05012 | | GFTFSS--YYMS | 3 | GIFF---TGETYYPDSVKG | 17 | QQYFDHIDI------ | 28 |
| MOR05013 | | GFTFSS--YYMS | 3 | GIFF---DGETYYADSVKG | 18 | QQYFDHIDI------ | 28 |
| MOR05014 | | GFTFSS--YYMS | 3 | GIFF---DGTTYYADSVKG | 19 | QQYFDHIDI------ | 28 |
| MOR05015 | | GFTFSS--YYMS | 3 | GTFF---DGSTYVADSVKG | 20 | QQYFDHIDI------ | 28 |
| MOR05016 | | GFTFSS--YYMS | 3 | NISY--DSSDTYYADSVKG | 14 | QQYFDHIDI------ | 28 |
| MOR05017 | | GFTFSS--YYMS | 3 | NISY--DSSDTYYADSVKG | 14 | QQYFDHIDI------ | 28 |
| MOR05018 | | GFTFSS--YYMS | 3 | NISY--DSSDTYYADSVKG | 14 | QQYFDHIDI------ | 28 |
| MOR05154 | | GFTFSS--YYMS | 3 | GIFF---DGETYYAGSVKG | 15 | QQYFDHIDI------ | 28 |
| MOR05155 | | GFTFSS--YYMS | 3 | GIFF---DGETYYAGSVKG | 15 | QQYFDHIDI------ | 28 |
| MOR05156 | | GFTFSS--YYMS | 3 | GIFF---DGETYYAGSVKG | 15 | QQYFDHIDI------ | 28 |
| MOR05157 | | GFTFSS--YYMS | 3 | GIFY---DGSTYYPDSVKG | 16 | QQYFDHIDI------ | 28 |
| MOR05158 | | GFTFSS--YYMS | 3 | GIFY---DGSTYYPDSVKG | 16 | QQYFDHIDI------ | 28 |
| MOR05159 | | GFTFSS--YYMS | 3 | GIFY---DGSTYYPDSVKG | 16 | QQYFDHIDI------ | 28 |
| MOR05160 | | GFTFSS--YYMS | 3 | GIFF---TGETYYPDSVKG | 17 | QQYFDHIDI------ | 28 |
| MOR05161 | | GFTFSS--YYMS | 3 | GIFF---TGETYYPDSVKG | 17 | QQYFDHIDI------ | 28 |
| MOR05162 | | GFTFSS--YYMS | 3 | GIFF---TGETYYPDSVKG | 17 | QQYFDHIDI------ | 28 |
| MOR05163 | | GFTFSS--YYMS | 3 | GIFF---DGETYYADSVKG | 18 | QQYFDHIDI------ | 28 |
| MOR05164 | | GFTFSS--YYMS | 3 | GIFF---DGETYYADSVKG | 18 | QQYFDHIDI------ | 28 |
| MOR05165 | | GFTFSS--YYMS | 3 | GIFF---DGETYVADSVKG | 18 | QQYFDHIDI------ | 28 |
| MOR05166 | | GFTFSS--YYMS | 3 | GIFF---DGTTYYADSVKG | 19 | QQYFDHIDI------ | 28 |
| MOR05167 | | GFTFSS--YYMS | 3 | GIFF---DGTTYYADSVKG | 19 | QQYFDHIDI------ | 28 |
| MOR05168 | | GFTFSS--YYMS | 3 | GIFF---DGTTYYADSVKG | 19 | QQYFDHIDI------ | 28 |
| MOR05169 | | GFTFSS--YYMS | 3 | GTFF---DGSTYVADSVKG | 20 | QQYFDHIDI------ | 28 |
| MOR05170 | | GFTFSS--YYMS | 3 | GTFF---DGSTYVADSVKG | 20 | QQYFDHIDI------ | 28 |
| MOR05171 | | GFTFSS--YYMS | 3 | GTFF---DGSTYVADSVKG | 20 | QQYFDHIDI------ | 28 |
| MOR04496 | | GFTFSS--YAIS | 4 | SISY--SGGSTYYADSVKG | 21 | MEYWYHLLYMDY--- | 29 |
| MOR04497 | | GFTFSN--HALS | 5 | GIQY--DGSNTGYADSVKG | 22 | YYGYSYMDY------- | 30 |
| MOR05019 | | GFTFSN--HALS | 5 | VISF---DGVKFYADSVKG | 23 | YYGYSYMDY------- | 30 |
| MOR05020 | | GFTFSN--HALS | 5 | GIQY--DGSNTGYADSVKG | 22 | YYGYSYMDY------- | 30 |
| MOR05021 | | GFTFSN--HALS | 5 | GIQY--DGSNTGYADSVKG | 22 | YYGYSYMDY------- | 30 |
| MOR05022 | | GFTFSN--HALS | 5 | GIQY--DGSNTGYADSVKG | 22 | YYGYSYMDY------- | 30 |
| MOR05172 | | GFTFSN--HALS | 5 | VISF---DGVKFYADSVKG | 23 | YYGYSYMDY------- | 30 |
| MOR05173 | | GFTFSN--HALS | 5 | VISF---DGVKFYADSVKG | 23 | YYGYSYMDY------- | 30 |
| MOR05174 | | GFTFSN--HALS | 5 | VISF---DGVKFYADSVKG | 23 | YYGYSYMDY------- | 30 |
| SEQ ID NO | VH6 | GDSVSSNSAAWN | 6 | RTYYR-SKWYNDYAVSVKS | 24 | | |
| MOR04609 | | GDSVSSNSAAWG | 7 | RIYYR-SKWLNDYAVSVKS | 25 | DGGWYID------- | 31 |

| Id no. | | LCDR 1 | SEQ ID # | LCDR 2 | SEQ ID # | CDR 3 | SEQ ID # |
|---|---|---|---|---|---|---|---|

VL Kappa CDR (L-CDR) Sequences

SanDI

| SEQ ID NO | Vκ1 | RASQGIS------SYLA | 32 | AASSLQS | 41 | | |
|---|---|---|---|---|---|---|---|
| MOR04493 | | RASQDIY------NYLN | 33 | GASSLQS | 42 | QQQNDYP--L | 50 |
| MOR05008 | | RASQDIY------NYLN | 33 | GASSLQS | 42 | QQQNDYP--L | 50 |
| MOR05009 | | RASQDIY------NYLN | 33 | GASSLQS | 42 | QQQNDYP--L | 50 |
| MOR04832 | | RASQDIS------ISLT | 34 | GAFSLQS | 43 | QQYYGTS--A | 51 |
| MOR05023 | | RASQDIS------ISLT | 34 | GAFSLQS | 43 | QQFYFHS--P | 52 |
| MOR05024 | | RASQDIS------ISLT | 34 | GAFSLQS | 43 | QQFWFEP--V | 53 |
| MOR05025 | | RASQDIS------ISLT | 34 | GAFSLQS | 43 | QQFWFHP--V | 54 |
| MOR05026 | | RASQDIS------ISLT | 34 | GAFSLQS | 43 | QQFWSEP--V | 55 |
| MOR05027 | | RASQDIS------ISLT | 34 | GAFSLQS | 43 | QQFWTEP--V | 56 |
| SEQ ID NO | Vκ3 | RASQSVSS-----SYLA | 35 | GASSRAT | 44 | | |
| MOR04496 | | RASQSIGD-----NYLA | 36 | DANNRAT | 45 | QQYDDHP--L | 57 |

| Id no. | | CDR 1 | SEQ ID # | CDR 2 | SEQ ID # | CDR 3 | SEQ ID # |
|---|---|---|---|---|---|---|---|

VL Lamda CDR (L-CDR) Sequences

| SEQ ID NO 40 | Vλ3 | SGDALGD------KYAS | 37 | DDSDRPS | 46 | | |
|---|---|---|---|---|---|---|---|
| MOR04494 | | GGDSLGG------KYVY | 38 | GDSKRPS | 47 | QSYTNALST- | 58 |
| MOR05010 | | GGDSLGG------KYVY | 38 | GDSKRPS | 47 | QSYTNALST- | 58 |
| MOR05011 | | GGDSLGG------KYVY | 38 | GDSKRPS | 47 | QSYTNALST- | 58 |
| MOR05012 | | GGDSLGG------KYVY | 38 | GDSKRPS | 47 | QSYTNALST- | 58 |
| MOR05013 | | GGDSLGG------KYVY | 38 | GDSKRPS | 47 | QSYTNALST- | 58 |
| MOR05014 | | GGDSLGG------KYVY | 38 | GDSKRPS | 47 | QSYTNALST- | 58 |
| MOR05015 | | GGDSLGG------KYVY | 38 | GDSKRPS | 47 | QSYTNALST- | 58 |
| MOR05016 | | GGDSLGG------KYVY | 38 | GDSKRPS | 47 | QSYDLQSLNI | 59 |
| MOR05017 | | GGDSLGG------KYVY | 38 | GDSKRPS | 47 | QSYDLKSLNV | 60 |
| MOR05018 | | GGDSLGG------KYVY | 38 | GDSKRPS | 47 | QSYDLGSLNL | 61 |
| MOR05154 | | GGDSLGG------KYVY | 38 | GDSKRPS | 47 | QSYDLQSLNI | 59 |
| MOR05155 | | GGDSLGG------KYVY | 38 | GDSKRPS | 47 | QSYDLKSLNV | 60 |

Annex 1 CDR Sequences Of Antibodies Of The Invention (continued)

| | | | | | | |
|---|---|---|---|---|---|---|
| MOR05156 | GGDSLGG------KYVY | 38 | GDSKRPS | 47 | QSYDLGSLNL | 61 |
| MOR05157 | GGDSLGG------KYVY | 38 | GDSKRPS | 47 | QSYDLQSLNI | 59 |
| MOR05158 | GGDSLGG------KYVY | 38 | GDSKRPS | 47 | QSYDLKSLNV | 60 |
| MOR05159 | GGDSLGG------KYVY | 38 | GDSKRPS | 47 | QSYDLGSLNL | 61 |
| MOR05160 | GGDSLGG------KYVY | 38 | GDSKRPS | 47 | QSYDLQSLNI | 59 |
| MOR05161 | GGDSLGG------KYVY | 38 | GDSKRPS | 47 | QSYDLKSLNV | 60 |
| MOR05162 | GGDSLGG------KYVY | 38 | GDSKRPS | 47 | QSYDLGSLNL | 61 |
| MOR05163 | GGDSLGG------KYVY | 38 | GDSKRPS | 47 | QSYDLQSLNI | 59 |
| MOR05164 | GGDSLGG------KYVY | 38 | GDSKRPS | 47 | QSYDLKSLNV | 60 |
| MOR05165 | GGDSLGG------KYVY | 38 | GDSKRPS | 47 | QSYDLGSLNL | 61 |
| MOR05166 | GGDSLGG------KYVY | 38 | GDSKRPS | 47 | QSYDLQSLNI | 59 |
| MOR05167 | GGDSLGG------KYVY | 38 | GDSKRPS | 47 | QSYDLKSLNV | 60 |
| MOR06168 | GGDSLGG------KYVY | 38 | GDSKRPS | 47 | QSYDLGSLNL | 61 |
| MOR05169 | GGDSLGG------KYVY | 38 | GDSKRPS | 47 | QSYDLQSLNI | 59 |
| MOR05170 | GGDSLGG------KYVY | 38 | GDSKRPS | 47 | QSYDLKSLNV | 60 |
| MOR05171 | GGDSLGG------KYVY | 38 | GDSKRPS | 47 | QSYDLGSLNL | 61 |
| MOR04497 | SGDNLGS------KYVH | 39 | ADNNRPS | 48 | QSYDHMLQ-- | 62 |
| MOR05019 | SGDNLGS------KYVH | 39 | ADNNRPS | 48 | QSYDHMLQ-- | 62 |
| MOR05020 | SGDNLGS------KYVH | 39 | ADNNRPS | 48 | SSYDSNSIR- | 63 |
| MOR05021 | SGDNLGS------KYVH | 39 | ADNNRPS | 48 | SSYDLDGVR- | 64 |
| MOR05022 | SGDNLGS------KYVH | 39 | ADNNRPS | 48 | SSYTTSGIR- | 65 |
| MOR05172 | SGDNLGS------KYVH | 39 | ADNNRPS | 48 | SSYDSNSIR- | 63 |
| MOR05173 | SGDNLGS------KYVH | 39 | ADNNRPS | 48 | SSYDLDGVR- | 64 |
| MOR05174 | SGDNLGS------KYVH | 39 | ADNNRPS | 48 | SSYTTSGIR- | 65 |
| MOR04609 | SGDNLGS------YYAN | 40 | ED-KRPS | 49 | QSFDSYHSDY | 66 |

Annex 2 HuCAL GOLD® anti-TSLP antibody amino acid sequences

MOR04493 VH, SEQ ID NO: 67:
QVQLVQSGAEVKKPGSSVKVSCKASGGTFSSYAISWVRQAPGQGLEWMGG
IIPDFGWANYAQKFQGRVTITADESTSTAYMELSSLRSEDTAVYYCARSG
MFYSILFDYWGQGTLVTVSS

MOR04493 VL, SEQ ID NO: 68:
DIQMTQSPSSLSASVGDRVTITCRASQDIYNYLNWYQQKPGKAPKLLIYG
ASSLQSGVPSRFSGSGSGTDFTLTISSLQPEDFAVYYCQQQNDYPLTFGQ
GTKVEIKRT

MOR04494 VH, SEQ ID NO: 69:
QVQLVESGGGLVQPGGSLRLSCAASGFTFSSYYMSWVRQAPGKGLEWVSN
ISYDSSDTYYADSVKGRFTISRDNSKNTLYLQMNSLRAEDTAVYYCARQQ
YFDHIDIWGQGTLVTVSS

MOR04494 VL, SEQ ID NO: 70:
DIELTQPPSVSVAPGQTARISCGGDSLGGKYVYWYQQKPGQAPVLVIYGD
SKRPSGIPERFSGSNSGNTATLTISGTQAEDEADYYCQSYTNALSTVFGG
GTKLTVLGQ

MOR04496 VH, SEQ ID NO: 71:
QVQLVESGGGLVQPGGSLRLSCAASGFTFSSYAISWVRQAPGKGLEWVSS
ISYSGSSTYYADSVKGRFTISRDNSKNTLYLQMNSLRAEDTAVYYCARME
YWYHLLYMDYWGQGTLVTVSS

MOR04496 VL, SEQ ID NO: 72:
DIVLTQSPATLSLSPGERATLSCRASQSIGDNYLAWYQQKPGQAPRLLIY
DANNRATGVPARFSGSGSGTDFTLTISSLEPEDFATYYCQQYDDHPLTFG
QGTKVEIKRT

MOR04497 VH, SEQ ID NO: 73:
QVQLVESGGGLVQPGGSLRLSCAASGFTFSNHALSWVRQAPGKGLEWVSG
IQYDGSNTGYADSVKGRFTISRDNSKNTLYLQMNSLRAEDTAVYYCARYY
GYSYMDYWGQGTLVTVSS

MOR04497 VL, SEQ ID NO: 74:
DIELTQPPSVSVAPGQTARISCSGDNLGSKYVHWYQQKPGQAPVLVIYAD
NNRPSGIPERFSGSNSGNTATLTISGTQAEDEADYYCQSYDHMLQVFGGG
TKLTVLGQ

MOR04609 VH, SEQ ID NO: 75:
QVQLQQSGPGLVKPSQTLSLTCAISGDSVSSNSAAWGWIRQSPGRGLEWL
GRIYYRSKWLNDYAVSKSRITINPDTSKNQFSLQLNSVTPEDTAVYYCA
RDGGWYIDVWGQGTLVTVSS

MOR04609 VL, SEQ ID NO: 76:
DIELTQPPSVSVAPGQTARISCSGDNLGSYYANWYQQKPGQAPVLVIYED
KRPSGIPERFSGSNSGNTATLTISGTQAEDEADYYCQSFDSYHSDYVFGG
GTKLTVLGQ

MOR04832 VH, SEQ ID NO: 77:
QVQLVQSGAEVKKPGSSVKVSCKASGGTFSSYAISWVRQAPGQGLEWMGN
IYPIFGYANYAQKFQGRVTITADESTSTAYMELSSLRSEDTAVYYCARYG
QYGQHFSHGGMDVWGQGTLVTVSS

MOR04832 VL, SEQ ID NO: 78:
DIQMTQSPSSLSASVGDRVTITCRASQDISISLTWYQQKPGKAPKLLIYG
AFSLQSGVPSRFSGSGSGTDFTLTISSLQPEDFATYYCQQYYGTSATFGQ
GTKVEIKRT

MOR05008 VH, SEQ ID NO: 79:
QVQLVQSGAEVKKPGSSVKVSCKASGGTFSSYAISWVRQAPGQGLEWMGG
IIPEFGFTNYAQKFQGRVTITADESTSTAYMELSSLRSEDTAVYYCARSG
MFYSILFDYWGQGTLVTVSS

MOR05008 VL, SEQ ID NO: 68:
DIQMTQSPSSLSASVGDRVTITCRASQDIYNYLNWYQQKPGKAPKLLIYG
ASSLQSGVPSRFSGSGSGTDFTLTISSLQPEDFAVYYCQQQNDYPLTFGQ
GTKVEIKRT

MOR05009 VH, SEQ ID NO: 80:
QVQLVQSGAEVKKPGSSVKVSCKASGGTFSSYAISWVRQAPGQGLEWMGH
ISPEFGFTNYAQKFQGRVTITADESTSTAYMELSSLRSEDTAVYYCARSG
MFYSILFDYWGQGTLVTVSS

MOR05009 VL, SEQ ID NO: 68:
DIQMTQSPSSLSASVGDRVTITCRASQDIYNYLNWYQQKPGKAPKLLIYG
ASSLQSGVPSRFSGSGSGTDFTLTISSLQPEDFAVYYGQQQNDYPLTFGQ
GTKVEIKRT

MOR05010 VH, SEQ ID NO: 81:
QVQLVESGGGLVQPGGSLRLSCAASGFTFSSYYMSWVRQAPGKGLEWVSG
IFFDGETYYAGSVKGRFTISRDNSKNTLYLQMNSLRAEDTAVYYCARQQY
FDHIDIWGQGTLVTVSS

MOR05010 VL, SEQ ID NO: 70:
DIELTQPPSVSVAPGQTARISCGGDSLGGKYVYWYQQKPGQAPVLVIYGD
SKRPSGIPERFSGSNSGNTATLTISGTQAEDEADYYCQSYTNALSTVFGG
GTKLTVLGQ

MOR05011 VH, SEQ ID NO: 82:
QVQLVESGGGLVQPGGSLRLSCAASGFTFSSYYMSWVRQAPGKGLEWVSG
IFYDGSTYYPDSVKGRFTISRDNSKNTLYLQMNSLRAEDTAVYYCARQQY
FDHIDIWGQGTLVTVSS

MOR05011 VL, SEQ ID NO: 70:
DIELTQPPSVSVAPGQTARISCGGDSLGGKYVYWYQQKPGQAPVLVIYGD
SKRPSGIPERFSGSNSGNTATLTISGTQAEDEADYYCQSYTNALSTVFGG
GTKLTVLGQ

MOR05012 VH, SEQ ID NO: 83:
QVQLVESGGGLVQPGGSLRLSCAASGFTFSSYYMSWVRQAPGKGLEWVSG
IFFTGETYYPDSVKGRFTISRDNSKNTLYLQMNSLRAEDTAVYYCARQQY
FDHIDIWGQGTLVTSS

MOR05012 VL, SEQ ID NO: 70:
DIELTQPPSVSVAPGQTARJSCGGDSLGGKYVYWYQQKPGQAPVLVIYGD
SKRPSGIPERFSGSNSGNTATLTISGTQAEDEADYYCQSYTNALSTVFGG
GTKLTVLGQ

MOR05013 VH, SEQ ID NO: 84:
QVQLVESGGGLVQPGGSLRLSCAASGFTFSSYYMSWVRQAPGKGLEWVSG
IFFDGETYYADSVKGRFTISRDNSKNTLYLQMNSLRAEDTAVYYCARQQY
FDHIDIWGQGTLVTSS

MOR05013 VL, SEQ ID NO: 70:
DIELTQPPSVSVAPGQTARISCGGDSLGGKYVYWYQQKPGQAPVLVIYGD
SKRPSGIPERFSGSNSGNTATLTISGTQAEDEADYYCQSYTNALSTVFGG
GTKLTVLGQ

MOR05014 VH, SEQ ID NO: 85:
QVQLVESGGGLVQPGGSLRLSCAASGFTFSSYYMSWVRQAPGKGLEWVSG
IFFDGTTYYADSVKGRFTISRDNSKNTLYLQMNSLRAEDTAVYYCARQQY
FDHIDIWGQGTLVTSS

MOR05014 VL, SEQ ID NO: 70:
DIELTQPPSVSVAPGQTARISCGGDSLGGKYVYWYQQKPGQAPVLVIYGD
SKRPSGIPERFSGSNSGNTATLTISGTQAEDEADYYCQSYTNALSTVFGG
GTKLTVLGQ

MOR05015 VH, SEQ ID NO: 86:
QVQLVESGGGLVQPGGSLRLSCAASGFTFSSYYMSWVRQAPGKGLEWVSG
TFFDGSTYYADSVKGRFTISRDNSKNTLYLQMNSLRAEDTAVYYCARQQY
FDHIDIWGQGTLVTSS

MOR05015 VL, SEQ ID NO: 70:
DIELTQPPSVSVAPGQTARISCGGDSLGGKYVYWYQQKPGQAPVLVIYGD
SKRPSGIPERFSGSNSGNTATLTISGTQAEDEADYYCQSYTNALSTVFGG
GTKITVLGQ

MOR05016 VH, SEQ ID NO: 69:
QVQLVESGGGLVQPGGSLRLSCAASGFTFSSYYMSWVRQAPGKGLEWVSN
ISYDSSDTYYADSVKGRFTISRDNSKNTLYLQMNSLRAEDTAVYYCARQQ
YFDHIDIWGQGTLVTSS

MOR05016 VL, SEQ ID NO: 87:
DIELTQPPSVSVAPGQTARISCGGDSLGGKYVYWYQQKPGQAPVLVIYGD
SKRPSGIPERFSGSNSGNTATLTISGTQAEDEADYYCQSYDLQSLNIVFG
GGTKLTVLGQ

MOR05017 VH, SEQ ID NO: 69:
QVQLVESGGGLVQPGGSLRLSCAASGFTFSSYYMSWVRQAPGKGLEWVSN
ISYDSSDTYYADSVKGRFTISRDNSKNTLYLQMNSLRAEDTAVYYCARQQ
YFDHIDIWGQGTLVTSS

MOR05017 VL, SEQ ID NO: 88:
DIELTQPPSVSVAPGQTARISCGGDSLGGKYVYWYQQKPGQAPVLVIYGD
SKRPSGIPERFSGSNSGNTATLTISGTQAEDEADYYCQSYDLKSLNVVFG
GGTKLTVLGQ

MOR05018 VH, SEQ ID NO: 69:
QVQLVESGGGLVQPGGSLRLSCAASGFTFSSYYMSWVRQAPGKGLEWVSN
ISYDSSDTYYADSVKGRFTISRDNSKNTLYLQMNSLRAEDTAVYYCARQQ
YFDHIDIWGQGTLVTSS

MOR05018 VL, SEQ ID NO: 89:
DIELTQPPSVSVAPGQTARISCGGDSLGGKYVYWYQQKPGQAPVLVIYGD
SKRPSGIPERFSGSNSGNTATLTISGTQAEDEADYYCQSYDLGSLNLVFG
GGTKLTVLGQ

MOR05019 VH, SEQ ID NO: 90:
QVQLVESGGGLVQPGGSLRLSCAASGFTFSNHALSWVRQAPGKGLEWVSV
ISFDGVKFYADSVKGRFTISRDNSKNTLYLQMNSLRAEDTAVYYCARYYG
YSYMDYWGQGTLVTSS

MOR05019 VL, SEQ ID NO: 74:
DIELTQPPSVSVAPGQTARLSCSGDNLGSKYVHWYQQKPGQAPVLVLYAD
NNRPSGIPERFSGSNSGNTATLTISGTQAEDEADYYGQSYDHMLQVFGGG
TKLTVLGQ

MOR05020 VH, SEQ ID NO: 73:
QVQLVESGGGLVQPGGSLRLSCAASGFTFSNHALSWVRQAPGKGLEWVSG
IQYDGSNTGYADSVKGRFTISRDNSKNTLYLQMNSLRAEDTAVYYCARYY
GYSYMDYWGQGTLVTSS

MOR05020 VL, SEQ ID NO: 91:
DIELTQPPSVSVAPGQTARISCSGDNLGSKYVHWYQQKPGQAPVLVIYAD
NNRPSGIPERFSGSNSGNTATLTISGTQAEDEADYYCSSYDSNSIRVFGG
GTKLTVLGQ

MOR05021 VH, SEQ ID NO: 73:
QVQLVESGGGLVQPGGSLRLSCAASGFTFSNHALSWVRQAPGKGLEWVSG
IQYDGSNTGYADSVKGRFTISRDNSKNTLYLQMNSLRAEDTAVYYCARYY
GYSYMDYWGQGTLVTSS

MOR05021 VL, SEQ ID NO: 92:
DIELTQPPSVSVAPGQTARISCSGDNLGSKYVHWYQQKPGQAPVLVIYAD
NNRPSGIPERFSGSNSGNTATLTISGTQAEDEADYYCSSYDLDGVRVFGG
GTKLTVLGQ

MOR05022 VH, SEQ ID NO: 73:
QVQLVESGGGLVQPGGSLRLSCAASGFTFSNHALSWVRQAPGKGLEWVSG
IQYDGSNTGYADSVKGRFTISRDNSKNTLYLQMNSLRAEDTAVYYCARYY
GYSYMDYWGQGTLVTSS

MOR05022 VL, SEQ ID NO: 93:
DIELTQPPSVSVAPGQTARISCSGDNLGSKYVHWYQQKPGQAPVLVIYAD
NNRPSGIPERFSGSNSGNTATLTISGTQAEDEADYYCSSYTTSGIRVFGG
GTKLTVLGQ

MOR05023 VH, SEQ ID NO: 77:
QVQLVQSGAEVKKPGSSVKVSCKASGGTFSSYAISWVRQAPGQGLEWMGN
IYPIFGYANYAQKFQGRVTITADESTSTAYMELSSLRSEDTAVYYCARYG
QYGQHFSHGGMDVWGQGTLVTSS

MOR05023 VL, SEQ ID NO: 94:
DIQMTQSPSSLSASVGDRVTITCRASQDISISLTWYQQKPGKAPKLLIYG
AFSLQSGVPSRFSGSGSGTDFTLTISSLQPEDFATYYCQQFYFHSPTFGQ
GTKVEIKRT

MOR05024 VH, SEQ ID NO: 77:
QVQLVQSGAEVKKPGSSVKVSCKASGGTFSSYAISWVRQAPGQGLEWMGN
IYPIFGYANYAQKFQGRVTITADESTSTAYMELSSLRSEDTAVYYCARYG
QYGQFIFSHGGMDVWGQGTLVTSS

MOR05024 VL, SEQ ID NO: 95:
DIQMTQSPSSLSASVGDRVTITCRASQDISISLTWYQQKPGKAPKLLIYG
AFSLQSGVPSRFSGSGSGTDFTLTISSLQPEDFATYYCQQFWFEPVTFGQ
GTKVEIKRT

MOR05025 VH, SEQ ID NO: 77:
QVQLVQSGAEVKKPGSSVKVSCKASGGTFSSYAISWVRQAPGQGLEWMGN
IYPIFGYANYAQKFQGRVTITADESTSTAYMELSSLRSEDTAVYYCARYG
QYGQHFSHGGMDVWGQGTLVTSS

MOR05025 VL, SEQ ID NO: 96:
DIQMTQSPSSLSASVGDRVTITCRASQDISISLTWYQQKPGKAPKLLIYG
AFSLQSGVPSRFSGSGSGTDFTLTISSLQPEDFATYYCQQFWFHPVTFGQ
GTKVEIKRT

MOR05026 VH, SEQ ID NO: 77:
QVQLVQSGAEVKKPGSSVKVSCKASGGTFSSYAISWVRQAPGQGLEWMGN
IYPIFGYANYAQKFQGRVTITADESTSTAYMELSSLRSEDTAVYYCARYG
QYGQHFSHGGMDVWGQGTLVTSS

MOR05026 VL, SEQ ID NO: 97:
DIQMTQSPSSLSASVGDRVTITCRASQDISISLTWYQQKPGKAPKLLIYG
AFSLQSGVPSRFSGSGSGTDFTLTISSLQPEDFATYYCQQFWSEPVTFGQ
GTKVEIKRT

MOR05027 VH, SEQ ID NO: 77:
QVQLVQSGAEVKKPGSSVKVSCKASGGTFSSYAISWVRQAPGQGLEWMGN
IYPIFGYANYAQKFQGRVTITADESTSTAYMELSSLRSEDTAVYYCARYG
QYGQHFSHGGMDVWGQGTLVTSS

MOR05027 VL, SEQ ID NO: 98:

-continued
DIQMTQSPSSLSASVGDRVTITCRASQDISISLTWYQQKPGKAPKLLIYG
AFSLQSGVPSRFSGSGSGTDFTLTISSLQPEDFATYYCQQFWTEPVTFGQ
GTKVEIKRT MOR05154 VH, SEQ ID NO: 81:
QVQLVESGGGLVQPGGSLRLSCAASGFTFSSYYMSWVRQAPGKGLEWVSG
IFFDGETYYAGSVKGRFTISRDNSKNTLYLQMNSLRAEDTAVYYCARQQY
FDHIDIWGQGTLVTVSS MOR05154 VL, SEQ ID NO: 87:
DIELTQPPSVSVAPGQTARISCGGDSLGGKYVYWYQQKPGQAPVLVIYGD
SKRPSGIPERFSGSNSGNTATLTISGTQAEDEADYYCQSYDLQSLNIVFG
GGTKLTVLGQ MOR05155 VH, SEQ ID NO: 81:
QVQLVESGGGLVQPGGSLRLSCAASGFTFSSYYMSWVRQAPGKGLEWVSG
IFFDGETYYAGSVKGRFTISRDNSKNTLYLQMNSLRAEDTAVYYCARQQY
FDHIDIWGQGTLVTVSS MOR05155 VL, SEQ ID NO: 88:
DIELTQPPSVSVAPGQTARISCGGDSLGGKYVYWYQQKPGQAPVLVIYGD
SKRPSGIPERFSGSNSGNTATLTISGTQAEDEADYYCQSYDLKSLNVVFG
GGTKLTVLGQ MOR05156 VH, SEQ ID NO: 81:
QVQLVESGGGLVQPGGSLRLSCAASGFTFSSYYMSWVRQAPGKGLEWVSG
IFFDGETYYAGSVKGRFTISRDNSKNTLYLQMNSLRAEDTAVYYCARQQY
FDHIDIWGQGTLVTVSS MOR05156 VL, SEQ ID NO: 89:
DIELTQPPSVSVAPGQTARISCGGDSLGGKYVYWYQQKPGQAPVLVIYGD
SKRPSGIPERFSGSNSGNTATLTISGTQAEDEADYYCQSYDLGSLNLVFG
GGTKLTVLGQ MOR05157 VH, SEQ ID NO: 82:
QVQLVESGGGLVQPGGSLRLSCAASGFTFSSYYMSWVRQAPGKGLEWVSG
IFYDGSTYYPDSVKGRFTISRDNSKNTLYLQMNSLRAEDTAVYYCARQQY
FDHIDIWGQGTLVTVSS MOR05157 VL, SEQ ID NO: 87:
DIELTQPPSVSVAPGQTARISCGGDSLGGKYVYWYQQKPGQAPVLVIYGD
SKRPSGIPERFSGSNSGNTATLTISGTQAEDEADYYCQSYDLQSLNIVFG
GGTKLTVLGQ MOR05158 VH, SEQ ID NO: 82:
QVQLVESGGGLVQPGGSLRLSCAASGFTFSSYYMSWVRQAPGKGLEWVSG
IFYDGSTYYPDSVKGRFTISRDNSKNThYLQMNSLRAEDTAVYYCARQQY
FDHIDIWGQGTLVTVSS MOR05158 VL, SEQ ID NO: 88:
DIELTQPPSVSVAPGQTARISCGGDSLGGKYVYWYQQKPGQAPVLVIYGD
SKRPSGIPERFSGSNSGNTATLTISGTQAEDEADYYCQSYDLKSLNVVFG
GGTKLTVLGQ MOR05159 VH, SEQ ID NO: 82:
QVQLVESGGGLVQPGGSLRLSCAASGFTFSSYYMSWVRQAPGKGLEWVSG
IFYDGSTYYPDSVKGRFTISRDNSKNTLYLQMNSLRAEDTAVYYCARQQY
FDHIDIWGQGTLVTVSS MOR05159 VL, SEQ ID NO: 89:
DIELTQPPSVSVAPGQTARISCGGDSLGGKYVYWYQQKPGQAPVLVIYGD
SKRPSGIPERFSGSNSGNTATLTISGTQAEDEADYYCQSYDLGSLNLVFG
GGTKLTVLGQ MOR05160 VH, SEQ ID NO: 83:
QVQLVESGGGLVQPGGSLRLSCAASGFTFSSYYMSWVRQAPGKGLEWVSG
IFFTGETYYPDSVKGRFTISRDNSKNTLYLQMNSLRAEDTAVYYCARQQY
FDHIDIWGQGTLVTVSS MOR05160 VL, SEQ ID NO: 87:
DIELTQPPSVSVAPGQTARISCGGDSLGGKYVYWYQQKPGQAPVLVIYGD
SKRPSGIPERFSGSNSGNTATLTISGTQAEDEADYYCQSYDLQSLNIVFG
GGTKLTVLGQ MOR05161 VH, SEQ ID NO: 83:
QVQLVESGGGLVQPGGSLRLSCAASGFTFSSYYMSWVRQAPGKGLEWVSG
IFFTGETYYPDSVKGRFTISRDNSKNTLYLQMNSLRAEDTAVYYCARQQY
FDHIDIWGQGTLVTVSS MOR05161 VL, SEQ ID NO: 88:
DIELTQPPSVSVAPGQTARISCGGDSLGGKYVYWYQQKPGQAPVLVIYGD
SKRPSGIPERFSGSNSGNTATLTISGTQAEDEADYYCQSYDLKSLNVVFG
GGTKLTVLGQ MOR05162 VH, SEQ ID NO: 83:
QVQLVESGGGLVQPGGSLRLSGAASGFTFSSYYMSWVRQAPGKGLEWVSG
IFFTGETYYPDSVKGRFTISRDNSKNTLYLQMNSLRAEDTAVYYCARQQY
FDHIDIWGQGTLVTVSS MOR05162 VL, SEQ ID NO: 89:
DIELTQPPSVSVAPGQTARISCGGDSLGGKYVYWYQQKPGQAPVLVIYGD
SKRPSGIPERFSGSNSGNTATLTISGTQAEDEADYYCQSYDLGSLNLVFG
GGTKLTVLGQ MOR05163 VH, SEQ ID NO: 84:
QVQLVESGGGLVQPGGSLRLSGAASGFTFSSYYMSWVRQAPGKGLEWVSG
IFFDGETYYADSVKGRFTISRDNSKNTLYLQMNSLRAEDTAVYYCARQQY
FDHIDIWGQGTLVTVSS MOR05163 VL, SEQ ID NO: 87:
DIELTQPPSVSVAPGQTARISCGGDSLGGKYVYWYQQKPGQAPVLVIYGD
SKRPSGIPERFSGSNSGNTATLTISGTQAEDEADYYCQSYDLQSLNIVFG
GGTKLTVLGQ MOR05164 VH, SEQ ID NO: 84:
QVQLVESGGGLVQPGGSLRLSCAASGFTFSSYYMSWVRQAPGKGLEWVSG
IFFDGETYYADSVKGRFTISRDNSKNTLYLQMNSLRAEDTAVYYCARQQY
FDHIDIWGQGTLVTVSS MOR05164 VL, SEQ ID NO: 88:
DIELTQPPSVSVAPGQTARISCGGDSLGGKYVYWYQQKPGQAPVLVIYGD
SKRPSGIPERFSGSNSGNTATLTISGTQAEDEADYYCQSYDLKSLNVVFG
GGTKLTVLGQ MOR05165 VH, SEQ ID NO: 84:
QVQLVESGGGLVQPGGSLRLSCAASGFTFSSYYMSWVRQAPGKGLEWVSG
WFDGETYYADSVKGRFTISRDNSKNTLYLQMI4SLRAEDTAVYYCARQQY
FDHIDIWGQGTLVTVSS MOR05165 VL, SEQ ID NO: 89:
DIELTQPPSVSVAPGQTARISCGGDSLGGKYVYWYQQKPGQAPVLVIYGD
SKRPSGIPERFSGSNSGNTATLTISGTQAEDEADYYCQSYDLGSLNLVFG
GGTKLTVLGQ MOR05166 VH, SEQ ID NO: 85:
QVQLVESGGGLVQPGGSLRLSCAASGFTFSSYYMSWVRQAPGKGLEWVSG
IFFDGTTYYADSVKGRFTISRDNSKNTLYLQMNSLRAEDTAVYYCARQQY
FDHIDIWGQGTLVTVSS MOR05166 VL, SEQ ID NO: 87:
DIELTQPPSVSVAPGQTARISCGGDSLGGKYVYWYQQKPGQAPVLVIYGD
SKRPSGIPERFSGSNSGNTATLTISGTQAEDEADYYCQSYDLQSLNIVFG
GGTKLTVLGQ MOR05167 VH, SEQ ID NO: 85:
QVQLVESGGGLVQPGGSLRLSCAASGFTFSSYYMSWVRQAPGKGLEWVSG
IFFDGITYYADSVKGRFTISRDNSKNTLYLQMNSLRAEDTAVYYCARQQY
FDHIDIWGQGTLVTVSS MOR05167 VL, SEQ ID NO: 88:
DIELTQPPSVSVAPGQTARISCGGDSLGGKYVYWYQQKPGQAPVLVIYGD
SKRPSGIPERFSGSNSGNTATLTISGTQAEDEADYYCQSYDLKSLNVVFG
GGTKLTVLGQ MOR05168 VH, SEQ ID NO: 85:
QVQLVESGGGLVQPGGSLRLSCAASGFTFSSYYMSWVRQAPGKGLEWVSG
IFFDGTTYYADSVKGRFTISRDNSKNTLYLQMNSLRAEDTAVYYCARQQY
FDHIDIWGQGTLVTVSS MOR05168 VL, SEQ ID NO: 89:
DIELTQPPSVSVAPGQTARISCGGDSLGGKYVYWYQQKPGQAPVLVIYGD
SKRPSGIPERFSGSNSGNTATLTISGTQAEDEADYYCQSYDLGSLNLVFG
GGTKLTVLGQ MOR05169 VH, SEQ ID NO: 86:
QVQLVESGGGLVQPGGSLRLSCAASGFTFSSYYMSWVRQAPGKGLEWVSG
TFFDGSTYYADSVKGRFTISRDNSKNTLYLQMNSLRAEDTAVYYCARQQY
FDHIDIWGQGTLVTVSS MOR05169 VL, SEQ ID NO: 87:
DIELTQPPSVSVAPGQTARISCGGDSLGGKYVYWYQQKPGQAPVLVIYGD
SKRPSGIPERFSGSNSGNTATLTISGTQAEDEADYYCQSYDLQSLNIVFG -continued
GGTKLTVLGQ MOR05170 VH, SEQ ID NO: 86:
QVQLVESGGGLVQPGGSLRLSCAASGFTFSSYYMSWVRQAPGKGLEWVSG
TFFDGSTYYADSVKGRFTISRDNSKNTLYLQMNSLRAEDTAVYYCARQQY
EDHIDIWGQGTLVTVSS MOR05170 VL, SEQ ID NO: 88:
DIELTQPPSVSVAPGQTARISCGGDSLGGKYVYWYQQKPGQAPVLVIYGD
SKRPSGIPERESGSNSGNTATLTISGTQAEDEADYYCQSYDLKSLNVVFG
GGTKLTVLGQ MOR05171 VH, SEQ ID NO: 86:
QVQLVESGGGLVQPGGSLRLSCAASGFTFSSYYMSWVRQAPGKGLEWVSG
TFFDGSTYYADSVKGRFTISRDNSKNTLYLQMNSLRAEDTAVYYCARQQY
FDHIDIWGQGTLVTVSS MOR05171 VL, SEQ ID NO: 89:
DIELTQPPSVSVAPGQTARISCGGDSLGGKYVYWYQQKPGQAPVLVIYGD
SKRPSGIPERFSGSNSGNTATLTISGTQAEDEADYYCQSYDLGSLNLVFG
GGTKLTVLGQ MOR05172 VH, SEQ ID NO: 90:
QVQLVESGGGLVQPGGSLRLSCAASGFTFSNHALSWVRQAPGKGLEWVSV
ISFDGVKYADSVKGRFTISRDNSKNTLYLQMNSLRAEDTAVYYCARYYGY
SYMDYWQGTLVTVSS MOR05172 VL, SEQ ID NO: 91:
DIELTQPPSVSVAPGQTARISCSGDNLGSKYVHWYQQKPGQAPVLVIYAD
NNRPSGIPERFSGSNSGNTATLTISGTQAEDEADYYCSSYDSNSIRVFGG
GTKLTVLGQ MOR05173 VH, SEQ ID NO: 90:
QVQLVESGGGLVQPGGSLRLSCAASGFTFSNHALSWVRQAPGKGLEWVSV
ISFDGVKFYADSVKGRFTISRDNSKNThYLQMNSLRAEDTAVYYCARYYG
YSYMDYWGQGTLVTVSS MOR05173 VL, SEQ ID NO: 92:
DIELTQPPSVSVAPGQTARISCSGDNLGSKYVHWYQQKPGQAPVLVIYAD
NNRPSGIPERFSGSNSGNTATLTISGTQAEDEADYYCSSYDLDGVRVFGG
GTKLTVLGQ MOR05174 VH, SEQ ID NO: 90:
QVQLVESGGGLVQPGGSLRLSCAASGFTFSNHALSWVRQAPGKGLEWVSV
ISFDGVKFYADSVKGRFTISRDNSKNTLYLQMNSLRAEDTAVYYCARYYG
YSYMDYWGQGTLVTVSS MOR05174 VL, SEQ ID NO: 93:
DIELTQPPSVSVAPGQTARISCSGDNLGSKYVHWYQQKPGQAPVLVIYAD
NNRPSGIPERFSGSNSGNTATLTISGTQAEDEADYYCSSYTTSGIRVFGG
GTKLTVLGQ MOR 5164, 5167, 5170 LIGHT CHAIN LAMBDA
The LC Lamda amino acid sequence is shown in
SEQ ID NO: 99: and is encoded by the nucleotide
sequence of SEQ ID NO: 100:
(SEQ ID NO: 99:)
MAWALLLLTLLTQGTGSWADIELTQPPSVSVAPGQTARISCGGDSLGGKY
VYWYQQKPGQAPVLVIYGDSKRPSGIPERFSGSNSGNTATLTISGTQAED
EADYYCQSYDLKSLNVVFGGGTKLTVLGQPKAAPSVTLFPPSSEELQANK
ATLVCLISDFYPGAVTVAWKADSSPVKAGVETTTPSKQSNNKYAASSYLS
LTPEQWKSHRSYSCQVTHEGSTVEKTVAPTECS (SEQ ID NO: 100:)
ATGGCCTGGGCTCTGCTGCTCCTCACCCTCCTCACTCAGGGCACAGGATC
CTGGGCTGATATCGAACTGACCCAGCCGCCTTCAGTGAGCGTTGCACCAG
GTCAGACCGCGCGTATCTCGTGTGGCGGCGATTCTCTTGGTGGTAAGTAT
GTTTATTGGTACCAGCAGAAACCCGGGCAGGCGCCAGTTCTTGTGATTTA
TGGTGATTCTAAGCGTCCCTCAGGCATCCCGGAACGCTTTAGCGGATCCA
ACAGCGGCAACACCGCGACCCTGACCATTAGCGGCACTCAGGCGGAAGAC
GAAGCGGATTATTATTGCCAGTCTTATGATCTTAAGTCTCTTAATGTTGT
GTTTGGCGGCGGCACGAAGTTAACCGTCCTAGGTCAGCCCAAGGCTGCCC
CCTCGGTCACTCTGTTCCCGCCCTCCTCTGAGGAGCTTCAAGCCAACAAG
GCCACACTGGTGTGTCTCATAAGTGACTTCTACCCGGGAGCCGTGACAGT
GGCCTGGAAGGCAGATAGCAGCCCCGTCAAGGCGGGAGTGGAGACCACCA
CACCCTCCAAACAAAGCAACAACAAGTACGCGGCCAGCAGCTATCTGAGC
CTGACGCCTGAGCAGTGGAAGTCCCACAGAAGCTACAGCTGCCAGGTCAC
GCATGAAGGGAGCACCGTGGAAGAGAACAGTGGCCCCTACAGAATGTTCA MOR 5164, 5167, 5170 LIGHT CHAIN LAMBDA (OPTIMIZED)
The LC Lamda amino acid sequence is shown in -continued
SEQ ID NO: 101: and is encoded by the nucleotide
sequence of SEQ ID NO: 102:
(SEQ ID NO: 101:)
MSVLTQVLALLLLWLTGTRCDIELTQPPSVSVAPGQTARISCGGDSLGGK
YVYWYQQKPGQAPVLVIYGDSKRPSGIPERFSGSNSGNTATLTISGTQAE
DEADYYCQSYDLKSLNVVFGGGTKLTVLGQPKAAPSVTLFPPSSEELQAN
KATLVCLISDFYPGAVTVAWKADSSPVKAGVETTTPSKQSNNKYAASSYL
SLTPEQWKSHRSYSCQVTHEGSTVEKTVAPTECS (SEQ ID NO: 102)
ATGAGTGTGCTCACTCAGGTCCTGGCGTTGCTGCTGCTGTGGCTTACAGG
TACGCGTTGCGACATCGAGCTGACCCAGCCCCCCAGCGTGTCTGTGGCCC
CTGGCCAGACCGCCCGGATCAGCTGTGGCGGCGACAGCCTGGGCGGCAAG
TACGTGTACTGGTATCAGCAGAAGCCCGGCCAGGCCCCCGTGCTGGTGAT
CTACGGCGACAGCAAGCGGCCCAGCGGCATCCCGGAGCCGTTCAGCGGCA
GCAACAGCGGCAACACCGCCACCCTGACCATCAGCGGCACCCAGGCCGAG
GACGAGGCCGACTACTACTGCCAGAGCTACGACCTGAAGAGCCTGAACGT
GGTGTTTGGCGGCGGAACAAAGCTTACCGTCCTAGGTCAGCCCAAGGCTG
CCCCCTCGGTCACTCTGTTCCCGCCCTCCTCTGAGGAGCTTCAAGCCAAC
AAGGCCACACTGGTGTGTCTCATAAGTGACTTCTACCCGGGAGCCGTGAC
AGTGGCCTGGAAGGCAGATAGCAGCCCCGTCAAGGCGGGAGTGGAGACAA
CCACACCCTCCAAACAAAGCAACAACAAGTACGCGGCCAGCAGCTATCTG
AGCCTGACGCCTGAGCAGTGGAAGTCCCACAGAAGCTACAGCTGCCAGGT
CACGCATGAAGGGAGCACCGTGGAAAAGACAGTGGCCCCTACAGAATGTT
CATAG MOR5164 HEAVY CHAIN IgG1:
The HC Lamda amino acid sequence is shown in
SEQ ID NO: 103 and is encoded by the nucleotide
sequence of SEQ ID NO: 104
(SEQ ID NO: 103)
MKHLWFFLLLVAAPRWVLSQVQLVESGGGLVQPGGSLRLSCAASGFTFSS
YYMSWVRQAPGKGLEWVSGIFFDGETYYADSVKGRFTISRDNSKNTLYLQ
MNSLRAEDTAVYYCARQQYFDHIDIWGQGTLVTVSSASTKGPSVFPLAPS
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEW
ESNGQPENNYKTFTPPVLDSDGSFFLYSKLTVDKSRWQQGNVFSCSVMH
EALHNHYTQKSLSLSPGK (SEQ ID NO: 104)
ATGAAACACCTGTGGTTCTTCCTCCTGCTGGTGGCAGCTCCCAGATGGGT
CCTGTCCCAGGTGCAATTGGTGGAAAGCGGCGGCGGCCTGGTGCAACCGG
GCGGCAGCCTGCGTCTGAGCTGCGCGGCCTCCGGATTTACCTTTTCTTCT
TATTATATGTCTTGGGTGCGCCAGGCCCCTGGGAAGGGTCTCGAGTGGGT
GAGCGGTATTTTTTTTGATGGTGAGACTTATTATGCTGATTCTGTTAAGG
GTCGTTTTACCATTTCACGTGATAATTCGAAAAACACCCTGTATCTGCAA
ATGAACAGCCTGCGTGCGGAAGATACGGCCGTGTATTATTGCGCGCGTCA
GCAGTATTTTGATCATATTGATATTTGGGGCCAAGGCACCCTGGTGACGG
TTAGCTCAGCCTCCACCAAGGGTCCATCGGTCTTCCCCCTGGCACCCTCC
TCCAAGAGCACCTCTGGGGGCACAGCGGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC
CTCAGCAGCGTGGTGACCGTGCCCTCCAGCAGCTTGGGCACCCAGACCTA
CATCTGCAACGTGAATCACAAGCCCAGCAACACCAAGGTGGACAAGAGAG
TTGAGCCCAAATCTTGTGACAAAACTCACACATGCCCACCGTGCCCAGCA
CCTGAACTCCTGGGGGGACCGTCAGTCTTCCTCTTCCCCCCAAAACCCAA
GGACACCCTCATGATCTCCCGGACCCCTGAGGTCACATGCGTGGTGGTGG
ACGTGAGCCACGAAGACCCTGAGGTCAAGTTCAACTGGTACGTGGACGGC
GTGGAGGTGCATAATGCCAAGACAAAGCCGCGGGAGGAGCAGTACAACAG
CACGTACCGGGTGGTCAGCGTCCTCACCGTCCTGCACCAGGACTGGCTGA
ATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGT
GTACACCCTGCCCCCATCCCGGGAGGAGATGACCAAGAACCAGGTCAGCC
TGACCTGCCTGGTCAAAGGCTTCTATCCCAGCGACATCGCCGTGGAGTGG
GAGAGCAATGGGCAGCCGGAGAACAACTACAAGACCACGCCTCCCGTGCT
GGACTCCGACGGCTCCTTCTTCCTCTACAGCAAGCTCACCGTGGACAAGA
GCAGGTGGCAGCAGGGGAACGTCTTCTCATGCTCCGTGATGCATGAGGCT
CTGCACAACCACTAGACGCAGAAGAGCCTCTCCCTGTCTCCGGGTAAATG
A MOR5164 HEAVY CHAIN IgG1 (OPTIMIZED)
The HC Lamda amino acid sequence is shown in
SEQ ID NO: 105 and is encoded by the nucleotide
sequence of SEQ ID NO: 106
(SEQ ID NO: 105)
MAWVWTLPFLMAAAQSVQAVQLVESGGGLVQPGGSLRLSCAASGFTFSS
YYMSWVRQAPGKGLEWVSGIFFDGETYYADSVKGRFTISRDNSKNTLYLQ
MNSLRAEDTAVYYCARQQYFDHIDIWGQGTLVTVSSASTKGPSVFPLAPS -continued
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEa
LHNHYTQKSLSLSPGK (SEQ ID NO: 106)
ATGGCTTGGGTGTGGACCTTGCCATTCCTGATGGCAGCTGCCCAAAGTGT
CCAGGCCCAGGTGCAGCTGGTGGAATCTGGCGGCGGACTGGTGCAGCCTG
GCGGCAGCCTGAGACTGAGCTGCGCCGCCAGCGGCTTCACCTTCAGCAGC
TACTACATGAGCTGGGTGCGGCAGGCCCCTGGCAAGGGCCTGGAATGGGT
GTCCGGCATCTTCTTCGACGGCGAGACCTACTACGCCGACAGCGTGAAGG
GCCGGTTCACCATCAGCCGGGACAACAGCAAGAACACCCTGTACCTGCAG
ATGAACAGCCTGCGGGCCGAGGACACCGCCGTGTACTACTGCGCCAGGCA
GCAGTACTTCGACCACATCGACATCTGGGGCCAGGGCACCCTGGTCACCG
TCTCCTCAGCCTCCACCAAGGGCCCATCGGTCTTCCCCCTGGCACCCTCC
TCCAAGAGCACCTCTGGGGGCACAGCGGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC
CTCAGCAGCGTCGTGACCGTGCCCTCCAGCAGCTTGGGCACCCAGACCTA
CATCTGCAACGTGAATCACAAGCCCAGCAACACCAAGGTGGACAAGAGAG
TTGAGCCCAAATCTTGTGACAAAACTCACACATGCCCACCGTGCCCAGCA
CCTGAACTCCTGGGGGGACCGTCAGTCTTCCTCTTCCCCCCAAAACCCAA
GGACACCCTCATGATCTCCCGGACCCCTGAGGTCACATGCGTGGTGGTGG
ACGTGAGCCACGAAGACCCTGAGGTCAAGTTCAACTGGTACGTGGACGGC
GTGGAGGTGCATAATGCCAAGACAAAGCCGCGGGAGGAGCAGTACAACAG
CACGTACCGTGTGGTCAGCGTCCTCACCGTCCTGCACCAGGACTGGCTGA
ATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGT
GTACACCCTGCCCCCATCCCGGGAGGAGATGACCAAGAACCAGGTCAGCC
TGACCTGCCTGGTCAAAGGCTTCTATCCCAGCGACATCGCCGTGGAGTGG
GAGAGCAATGGGCAGCCGGAGAACAACTACAAGACCACGCCTCCCGTGCT
GGACTCCGACGGCTCCTTCTTCCTCTATAGCAAGCTCACCGTGGACAAGA
GCAGGTGGCAGCAGGGGAACGTCTTCTCATGCTCCGTGATGCATGAGGCT
CTGCACAACCACTACACGCAGAAGAGCCTCTCCCTGTCCCCGGGTAAATG
A MOR5167 HEAVY CHAIN IgG1:
The HC Lamda amino acid sequence is shown in
SEQ ID NO: 107 and is encoded by the nucleotide
sequence of SEQ ID NO: 108

(SEQ ID NO: 107)
MKHLWFFLLLVAAPRWVLSQVQLVESGGGLVQPGGSLRLSCAASGFTFSS
YYMSWVRQAPGKGLEWVSGIFFDGTTYYADSVKGRFTISRDNSKNTLYLQ
MNSLRAEDTAVYYCARQQYFDHIDIWGQGTLVTVSSASTKGPSVFPLAPS
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK (SEQ ID NO: 108)
ATGAAACACCTGTGGTTCTTCCTCCTGCTGGTGGCAGCTCCCAGATGGGT
CCTGTCCCAGGTGCAATTGGTGGAAAGCGGCGGCGGCCTGGTGCAACCGG
GCGGCAGCCTGCGTCTGAGCTGCGCGGCCTCCGGATTTACCTTTTCTTCT
TATTATATGTCTTGGGTGCGCCAAGCCCCTGGGAAGGGTCTCGAGTGGGT
GAGCGGTATTTTTTTTGATGGTACTACTTATTATGCTGATTCTGTTAAGG
GTCGTTTTACCATTTCACGTGATAATTCGAAAAACACCCTGTATCTGCAA
ATGAACAGCCTGCGTGCGGAAGATACGGCCGTGTATTATTGCGCGCGTCA
GCAGTATTTTGATCATATTGATATTTGGGGCCAAGGCACCCTGGTGACGG
TTAGCTCAGCCTCCACCAAGGGTCCATCGGTCTTCCCCCTGGCACCCTCC
TCCAAGAGCACCTCTGGGGGCACAGCGGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC
CTCAGCAGCGTGGTGACCGTGCCCTCCAGCAGCTTGGGCACCCAGACCTA
CATCTGCAACGTGAATCACAAGCCCAGCAACACCAAGGTGGACAAGAGAG
TTGAGCCCAAATCTTGTGACAAAACTCACACATGCCCACCGTGCCCAGCA
CCTGAACTCCTGGGGGGACCGTCAGTCTTCCTCTTCCCCCCAAAACCCAA
GGAGACCCTCATGATCTCCCGGACCCCTGAGGTCACATGCGTGGTGGTGG
ACGTGAGCCACGAAGACCCTGAGGTCAAGTTCAACTGGTACGTGGACGGC
GTGGAGGTGCATAATGCCAAGACAAAGCCGCGGGAGGAGCAGTACAACAG
CACGTACCGTGTGGTCAGCGTCCTCACCGTCCTGCACCAGGACTGGCTGA
ATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGT
GTACACCCTGCCCCCATCCCGGGAGGAGATGACCAAGAACCAGGTCAGCC
TGACCTGCCTGGTCAAAGGCTTCTATCCCAGCGACATCGCCGTGGAGTGG
GAGAGCAATGGGCAGCCGGAGAACAACTACAAGACCACGCCTCCCGTGCT
GGACTCCGACGGCTCCTTCTTCCTCTATAGCAAGCTCACCGTGGACAAGA
GCAGGTGGCAGCAGGGGAACGTCTTCTCATGCTCCGTGATGCATGAGGCT
CTGCACAACCACTACACGCAGAAGAGCCTCTCCCTGTCTCCGGGTAAATG
A

MOR5167 HEAVY CHAIN IgG1 (OPTIMIZED):
The HC Lamda amino acid sequence is shown in
SEQ ID NO: 109 and is encoded by the nucleotide
sequence of SEQ ID NO: 110

(SEQ ID NO: 109)
MAWVWTLPFLMAAAQSVQAVQLVESGGGLVQPGGSLRLSCAASGFTFSS
YYMSWVRQAPGKGLEWVSGIFFDGTTYYADSVKGRFTISRDNSKNTLYLQ
MNSLRAEDTAVYYCARQQYFDHIDIWGQGTLVTVSSASTKGPSVFPLAPS
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK (SEQ ID NO: 110)
ATGGCTTGGGTGTGGACCTTGCCATTCCTGATGGCAGCTGCCCAAAGTGT
CCAGGCCCAGGTGCAGCTGGTGGAATCTGGCGGCGGACTGGTGCAGCCTG
GCGGCAGCCTGAGACTGAGCTGCGCCGCCAGCGGCTTCACCTTCAGCAGC
TACTACATGAGCTGGGTGCGGCAGGCCCCTGGCAAGGGCCTGGAATGGGT
GTCCGGCATCTTCTTCGACGGCACCACCTACTACGCCGACAGCGTGAAGG
GCCGGTTCACCATCAGCCGGGACAACAGCAAGAACACCCTGTACCTGCAG
ATGAACAGCCTGCGGGCCGAGGACACCGCCGTGTACTACTGCGCCAGGCA
GCAGTACTTCGACCACATCGACATCTGGGGCCAGGGCACCCTGGTCACCG
TCTCCTCAGCCTCCACCAAGGGCCCATCGGTCTTCCCCCTGGCACCCTCC
TCCAAGAGCACCTCTGGGGGCACAGCGGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC
CTCAGCAGCGTCGTGACCGTGCCCTCCAGCAGCTTGGGCACCCAGACCTA
CATCTGCAACGTGAATCACAAGCCCAGCAACACCAAGGTGGACAAGAGAG
TTGAGCCCAAATCTTGTGACAAAACTCACACATGCCCACCGTGCCCAGCA
CCTGAACTCCTGGGGGGACCGTCAGTCTTCCTCTTCCCCCCAAAACCCAA
GGACACCCTCATGATCTCCCGGACCCCTGAGGTCACATGCGTGGTGGTGG
ACGTGAGCCACGAAGACCCTGAGGTCAAGTTCAACTGGTACGTGGACGGC
GTGGAGGTGCATAATGCCAAGACAAAGCCGCGGGAGGAGCAGTACAACAG
CACGTACCGTGTGGTCAGCGTCCTCACCGTCCTGCACCAGGACTGGCTGA
ATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGT
GTACACCCTGCCCCCATCCCGGGAGGAGATGACCAAGAACCAGGTCAGCC
TGACCTGCCTGGTCAAAGGCTTCTATCCCAGCGACATCGCCGTGGAGTGG
GAGAGCAATGGGCAGCCGGAGAACAACTACAAGACCACGCCTCCCGTGCT
GGACTCCGACGGCTCCTTCTTCCTCTATAGCAAGCTCACCGTGGACAAGA
GCAGGTGGCAGCAGGGGAACGTCTTCTCATGCTCCGTGATGCATGAGGCT
CTGCACAACCACTACACGCAGAAGAGCCTCTCCCTGTCCCCGGGTAAATG
A

MOR5170 HEAVY CHAIN IgG1:
The HC Lamda amino acid sequence is shown in
SEQ ID NO: 111 and is encoded by the nucleotide
sequence of SEQ ID NO: 112

(SEQ ID NO: 111)
MKHLWFFLLLVAAPRWVLSQVQLVESGGGLVQPGGSLRLSCAASGFTFSS
YYMSWVRQAPGKGLEWVSGFFDGSTYYADSVKGRFTISRDNSKNTLYLQ
MNSLRAEDTAVYYCARQQYFDHIDIWGQGTLVTVSSASTKGPSVFPLAPS
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK (SEQ ID NO: 112)
ATGAAACACCTGTGGTTCTTCCTCCTGCTGGTGGCAGCTCCCAGATGGGT
CCTGTCCCAGGTGCAATTGGTGGAAAGCGGCGGCGGCCTGGTGCAACCGG
GCGGCAGCCTGCGTCTGAGCTGCGCGGCCTCCGGATTTACCTTTCTTCT
TATTATATGTCTTGGGTGCGCCAAGCCCCTGGGAAGGGTCTCGAGTGGGT
GAGCGGTACTTTTTTTGATGGTTCTACTTATTATGCTGATTCTGTTAAGG
GTCGTTTACCATtTTCACGTGATAATTCGAAAAACACCCTGTATCTGCAA
ATGAACAGCCTGCGTGCGGAAGATACGGCCGTGTATTATTGCGCGCGTCA
GCAGTATTTTGATCATATTGATATTTGGGGCCAAGGCACCCTGGTGACGG
TTAGCTCAGCCTCCACCAAGGGTCCATCGGTCTTCCCCCTGGCACCCTCC
TCCAAGAGCACCTCTGGGGGCACAGCGGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC

```
CTCAGCAGCGTGGTGACCGTGCCCTCCAGCAGCTTGGGCACCCAGACCTA
CATCTGCAACGTGAATCACAAGCCCAGCAACACCAAGGTGGACAAGAGAG
TTGAGCCCAAATCTTGTGACAAAACTCACACATGCCCGACCCTGCCCAGCA
CCTGAACTCCTGGGGGGACCGTCAGTCTTCCTCTTCCCCCCAAAACCCAA
GGACACCCTCATGATCTCCCGGACCCCTGAGGTCACATGCGTGGTGGTGG
ACGTGAGCCACGAAGACCCTGAGGTCAAGTTCAACTGGTACGTGGACGGC
GTGGAGGTGCATAATGCCAAGACAAAGCCGCGGGAGGAGCAGTACAACAG
CACGTACCGGGTGGTCAGCGTCCTCACCGTCCTGCACCAGGACTGGCTGA
ATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGT
GTACACCCTGCCCCCATCCCGGGAGGAGATGACCAAGAACCAGGTCAGCC
TGACCTGCCTGGTCAAAGGCTTCTATCCCAGCGACATCGCCGTGGAGTGG
GAGAGCAATGGGCAGCCGGAGAACAACTACAAGACCACGCCTCCCGTGCT
GGACTCCGACGGCTCCTTCTTCCTCTACAGCAAGCTCACCGTGGACAAGA
GCAGGTGGCAGCAGGGGAACGTCTTCTCATGCTCCGTGATGCATGAGGCT
CTGCACAACCACTACACGCAGAAGAGCCTCTCCCTGTCTCCGGGTAAATG
A

MOR5179 HEAVY CHAIN IgG1 (OPTIMIZED):
The HG Lamda amino acid sequence is shown in SEQ
ID NO: 113 and is encoded by the
nucleotide sequence of SEQ ID NO: 114
                                    (SEQ ID NO: 113)
MAWVWTLPFLMAAAQSVQAVQLVESGGGLVQPGGSLRLSCAASGFTFSS
YYMSWVRQAPGKGLEWVSGTFFDGSTYYADSVKGRFTISRDNSKNTLYLQ
MNSLRAEDTAVYYCARQQYFDHIDIWGQGTLVTVSSASTKGPSVFPLAPS
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK (SEQ ID NO: 114)
ATGGCTTGGGTGTGGACCTTGCCATTCCTGATGGCAGCTGCCCAAAGTGT
GCCAGGCCAGGTGCAGCTGGTGGAATCTGGCGGCGGACTGGTGCAGCCT
GGGCGGCAGCCTGAGACTGAGCTGCGCCGCCAGCGGCTTCACCTTCAGCA
GCTACTACATGAGCTGGGTGCGGCAGGCCCCTGGCAAGGGCCTGGAATGG
ATGTCCGGCACCTTCTTCGACGGCAGCACCTACTACGCCGACAGCGTGAA
CGGCCGGTTCACCATCAGCCGGGACAACAGCAAGAACACCCTGTACCTGC
CGATGAACAGCCTGCGGGCCGAGGACACCGCCGTGTACTACTGCGCCAGG
CAGCAGTACTTCGACCACATCGACATCTGGGGCCAGGGCACCCTGGTCAC
GGTCTCCTCAGCCTCCACCAAGGGCCCATCGGTCTTCCCCCTGGGACCCT
CCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGAC
CAGCGGCGTGCACACCTTCCCGGCTGTCCTACAGTCCTCAGGACTCTACT
CCCTCAGCAGCGTCGTGACCGTGCCCTCCAGCAGCTTGGGCACCCAGACC
CACATCTGCAACGTGAATCACAAGCCCAGCAACACCAAGGTGGACAAGAG
AGTTGAGCCCAAATCTTGTGACAAAACTCACACATGCCCACCGTGCCCAG
GACCTGAACTCCTGGGGGGACCGTCAGTCTTCCTCTTCCCCCCAAAACCC
GAGGACACCCTCATGATCTCCCGGACCCCTGAGGTCACATGCGTGGTGGT
AGACGTGAGCCACGAAGACCCTGAGGTCAAGTTCAACTGGTAGGTGGACG
GCGTGGAGGTGCATAATGCCAAGACAAAGCCGCGGGAGGAGCAGTACAAC
CGCACGTACCGTGTGGTCAGCGTCCTCACCGTCCTGCACCAGGACTGGCT
GAATGGCAAGGAGTACAAGTGCAAGGTCTCCAACAAAGCCCTCCCAGCCC
CCATCGAGAAAACCATCTCCAAAGCCAAAGGGCAGCCCCGAGAACCACAG
GTGTACACCCTGCCCCCATCCCGGGAGGAGATGACCAAGAACCAGGTCAG
CCTGACCTGCCTGGTCAAAGGCTTCTATCCCAGCGACATCGCCGTGGAGT
GGGAGAGCAATGGGCAGCCGGAGAACAACTACAAGACCACGCCTCCCGTG
CTGGACTCCGACGGCTCCTTCTTCCTCTATAGCAAGCTCAGCGTGGACAA
TAGCAGGTGGCAGCAGGGGAACGTCTTCTCATGCTCCGTGATGCATGAGG
TCTGCACAACCACTACACGCAGAAGAGCCTCTCCCTGTCCCCGGGTAAAG
A
```

---

The invention claimed is:

1. An isolated antibody or antigen-binding fragment thereof that specifically binds to human TSLP, wherein said antibody or said antigen-binding fragment thereof comprises: a heavy chain variable region comprising an H-CDR1 region comprising the amino acid sequence of SEQ ID NO: 3, an H-CDR2 region comprising the amino acid sequence of SEQ ID NO: 20, an H-CDR3 region comprising the amino acid sequence of SEQ ID NO: 28, and a light chain variable region comprising an L-CDR1 region comprising the amino acid sequence of SEQ ID NO: 38, an L-CDR2 region comprising the amino acid sequence of SEQ ID NO: 47, and an L-CDR3 region comprising the amino acid sequence of SEQ ID NO: 60.

2. The isolated antibody of claim 1, which is an IgG1, IgG2 or IgG4 antibody.

3. The isolated antibody of claim 1, which is a human antibody.

4. A composition comprising the isolated antibody or antigen-binding fragment thereof of claim 1.

* * * * *

SEQUENCE LISTING

<160> NUMBER OF SEQ ID NOS: 115

<210> SEQ ID NO 1
<211> LENGTH: 10
<212> TYPE: PRT
<213> ORGANISM: Artificial sequence
<220> FEATURE:
<223> OTHER INFORMATION: Synthetic sequence: H-CDR 1

<400> SEQUENCE: 1

Gly Gly Thr Phe Ser Ser Tyr Ala Ile Ser
1               5                   10

<210> SEQ ID NO 2
<211> LENGTH: 10
<212> TYPE: PRT
<213> ORGANISM: Artificial sequence
<220> FEATURE:
<223> OTHER INFORMATION: Synthetic sequence: H-CDR 1

<400> SEQUENCE: 2

Gly Phe Thr Phe Ser Ser Tyr Ala Met Ser
1               5                   10

<210> SEQ ID NO 3
<211> LENGTH: 10
<212> TYPE: PRT
<213> ORGANISM: Artificial sequence
<220> FEATURE:
<223> OTHER INFORMATION: Synthetic sequence: H-CDR 1

<400> SEQUENCE: 3

Gly Phe Thr Phe Ser Ser Tyr Tyr Met Ser
1               5                   10

```
<210> SEQ ID NO 4
<211> LENGTH: 10
<212> TYPE: PRT
<213> ORGANISM: Artificial sequence
<220> FEATURE:
<223> OTHER INFORMATION: Synthetic sequence: H-CDR 1

<400> SEQUENCE: 4

Gly Phe Thr Phe Ser Ser Tyr Ala Ile Ser
1               5                   10

<210> SEQ ID NO 5
<211> LENGTH: 10
<212> TYPE: PRT
<213> ORGANISM: Artificial sequence
<220> FEATURE:
<223> OTHER INFORMATION: Synthetic sequence: H-CDR 1

<400> SEQUENCE: 5

Gly Phe Thr Phe Ser Asn His Ala Leu Ser
1               5                   10

<210> SEQ ID NO 6
<211> LENGTH: 12
<212> TYPE: PRT
<213> ORGANISM: Artificial sequence
<220> FEATURE:
<223> OTHER INFORMATION: Synthetic sequence: H-CDR 1

<400> SEQUENCE: 6

Gly Asp Ser Val Ser Ser Asn Ser Ala Ala Trp Asn
1               5                   10

<210> SEQ ID NO 7
<211> LENGTH: 12
<212> TYPE: PRT
<213> ORGANISM: Artificial sequence
<220> FEATURE:
<223> OTHER INFORMATION: Synthetic sequence: H-CDR 1

<400> SEQUENCE: 7

Gly Asp Ser Val Ser Ser Asn Ser Ala Ala Trp Gly
1               5                   10

<210> SEQ ID NO 8
<211> LENGTH: 17
<212> TYPE: PRT
<213> ORGANISM: Artificial sequence
<220> FEATURE:
<223> OTHER INFORMATION: Synthetic sequence: H-CDR 2

<400> SEQUENCE: 8

Gly Ile Ile Pro Ile Phe Gly Thr Ala Asn Tyr Ala Gln Lys Phe Gln
1               5                   10                  15

Gly

<210> SEQ ID NO 9
<211> LENGTH: 17
<212> TYPE: PRT
<213> ORGANISM: Artificial sequence
<220> FEATURE:
<223> OTHER INFORMATION: Synthetic sequence: H-CDR 2

<400> SEQUENCE: 9

Gly Ile Ile Pro Asp Phe Gly Trp Ala Asn Tyr Ala Gln Lys Phe Gln
1               5                   10                  15

Gly
```

-continued

```
<210> SEQ ID NO 10
<211> LENGTH: 17
<212> TYPE: PRT
<213> ORGANISM: Artificial sequence
<220> FEATURE:
<223> OTHER INFORMATION: Synthetic sequence: H-CDR 2

<400> SEQUENCE: 10

Gly Ile Ile Pro Glu Phe Gly Phe Thr Asn Tyr Ala Gln Lys Phe Gln
1               5                   10                  15

Gly

<210> SEQ ID NO 11
<211> LENGTH: 17
<212> TYPE: PRT
<213> ORGANISM: Artificial sequence
<220> FEATURE:
<223> OTHER INFORMATION: Synthetic sequence: H-CDR 2

<400> SEQUENCE: 11

His Ile Ser Pro Glu Phe Gly Phe Thr Asn Tyr Ala Gln Lys Phe Gln
1               5                   10                  15

Gly

<210> SEQ ID NO 12
<211> LENGTH: 17
<212> TYPE: PRT
<213> ORGANISM: Artificial sequence
<220> FEATURE:
<223> OTHER INFORMATION: Synthetic sequence: H-CDR 2

<400> SEQUENCE: 12

Asn Ile Tyr Pro Ile Phe Gly Tyr Ala Asn Tyr Ala Gln Lys Phe Gln
1               5                   10                  15

Gly

<210> SEQ ID NO 13
<211> LENGTH: 17
<212> TYPE: PRT
<213> ORGANISM: Artificial sequence
<220> FEATURE:
<223> OTHER INFORMATION: Synthetic sequence: H-CDR 2

<400> SEQUENCE: 13

Ala Ile Ser Gly Ser Gly Gly Ser Thr Tyr Tyr Ala Asp Ser Val Lys
1               5                   10                  15

Gly

<210> SEQ ID NO 14
<211> LENGTH: 17
<212> TYPE: PRT
<213> ORGANISM: Artificial sequence
<220> FEATURE:
<223> OTHER INFORMATION: Synthetic sequence: H-CDR 2

<400> SEQUENCE: 14

Asn Ile Ser Tyr Asp Ser Ser Asp Thr Tyr Tyr Ala Asp Ser Val Lys
1               5                   10                  15

Gly

<210> SEQ ID NO 15
<211> LENGTH: 16
<212> TYPE: PRT
```

```
<213> ORGANISM: Artificial sequence
<220> FEATURE:
<223> OTHER INFORMATION: Synthetic sequence: H-CDR 2

<400> SEQUENCE: 15

Gly Ile Phe Phe Asp Gly Glu Thr Tyr Tyr Ala Gly Ser Val Lys Gly
1               5                   10                  15

<210> SEQ ID NO 16
<211> LENGTH: 16
<212> TYPE: PRT
<213> ORGANISM: Artificial sequence
<220> FEATURE:
<223> OTHER INFORMATION: Synthetic sequence: H-CDR 2

<400> SEQUENCE: 16

Gly Ile Phe Tyr Asp Gly Ser Thr Tyr Tyr Pro Asp Ser Val Lys Gly
1               5                   10                  15

<210> SEQ ID NO 17
<211> LENGTH: 16
<212> TYPE: PRT
<213> ORGANISM: Artificial sequence
<220> FEATURE:
<223> OTHER INFORMATION: Synthetic sequence: H-CDR 2

<400> SEQUENCE: 17

Gly Ile Phe Phe Thr Gly Glu Thr Tyr Tyr Pro Asp Ser Val Lys Gly
1               5                   10                  15

<210> SEQ ID NO 18
<211> LENGTH: 16
<212> TYPE: PRT
<213> ORGANISM: Artificial sequence
<220> FEATURE:
<223> OTHER INFORMATION: Synthetic sequence: H-CDR 2

<400> SEQUENCE: 18

Gly Ile Phe Phe Asp Gly Glu Thr Tyr Tyr Ala Asp Ser Val Lys Gly
1               5                   10                  15

<210> SEQ ID NO 19
<211> LENGTH: 16
<212> TYPE: PRT
<213> ORGANISM: Artificial sequence
<220> FEATURE:
<223> OTHER INFORMATION: Synthetic sequence: H-CDR 2

<400> SEQUENCE: 19

Gly Ile Phe Phe Asp Gly Thr Thr Tyr Tyr Ala Asp Ser Val Lys Gly
1               5                   10                  15

<210> SEQ ID NO 20
<211> LENGTH: 16
<212> TYPE: PRT
<213> ORGANISM: Artificial sequence
<220> FEATURE:
<223> OTHER INFORMATION: Synthetic sequence: H-CDR 2

<400> SEQUENCE: 20

Gly Thr Phe Phe Asp Gly Ser Thr Tyr Tyr Ala Asp Ser Val Lys Gly
1               5                   10                  15

<210> SEQ ID NO 21
<211> LENGTH: 17
<212> TYPE: PRT
<213> ORGANISM: Artificial sequence
<220> FEATURE:
```

```
<223> OTHER INFORMATION: Synthetic sequence: H-CDR 2

<400> SEQUENCE: 21

Ser Ile Ser Tyr Ser Gly Ser Ser Thr Tyr Tyr Ala Asp Ser Val Lys
1               5                   10                  15

Gly

<210> SEQ ID NO 22
<211> LENGTH: 17
<212> TYPE: PRT
<213> ORGANISM: Artificial sequence
<220> FEATURE:
<223> OTHER INFORMATION: Synthetic sequence: H-CDR 2

<400> SEQUENCE: 22

Gly Ile Gln Tyr Asp Gly Ser Asn Thr Gly Tyr Ala Asp Ser Val Lys
1               5                   10                  15

Gly

<210> SEQ ID NO 23
<211> LENGTH: 16
<212> TYPE: PRT
<213> ORGANISM: Artificial sequence
<220> FEATURE:
<223> OTHER INFORMATION: Synthetic sequence: H-CDR 2

<400> SEQUENCE: 23

Val Ile Ser Phe Asp Gly Val Lys Phe Tyr Ala Asp Ser Val Lys Gly
1               5                   10                  15

<210> SEQ ID NO 24
<211> LENGTH: 18
<212> TYPE: PRT
<213> ORGANISM: Artificial sequence
<220> FEATURE:
<223> OTHER INFORMATION: Synthetic sequence: H-CDR 2

<400> SEQUENCE: 24

Arg Thr Tyr Tyr Arg Ser Lys Trp Tyr Asn Asp Tyr Ala Val Ser Val
1               5                   10                  15

Lys Ser

<210> SEQ ID NO 25
<211> LENGTH: 18
<212> TYPE: PRT
<213> ORGANISM: Artificial sequence
<220> FEATURE:
<223> OTHER INFORMATION: Synthetic sequence: H-CDR 2

<400> SEQUENCE: 25

Arg Ile Tyr Tyr Arg Ser Lys Trp Leu Asn Asp Tyr Ala Val Ser Val
1               5                   10                  15

Lys Ser

<210> SEQ ID NO 26
<211> LENGTH: 11
<212> TYPE: PRT
<213> ORGANISM: Artificial sequence
<220> FEATURE:
<223> OTHER INFORMATION: Synthetic sequence: H-CDR 3

<400> SEQUENCE: 26

Ser Gly Met Phe Tyr Ser Ile Leu Phe Asp Tyr
1               5                   10
```

```
<210> SEQ ID NO 27
<211> LENGTH: 15
<212> TYPE: PRT
<213> ORGANISM: Artificial sequence
<220> FEATURE:
<223> OTHER INFORMATION: Synthetic sequence: H-CDR 3

<400> SEQUENCE: 27

Tyr Gly Gln Tyr Gly Gln His Phe Ser His Gly Gly Met Asp Val
1               5                   10                  15

<210> SEQ ID NO 28
<211> LENGTH: 9
<212> TYPE: PRT
<213> ORGANISM: Artificial sequence
<220> FEATURE:
<223> OTHER INFORMATION: Synthetic sequence: H-CDR 3

<400> SEQUENCE: 28

Gln Gln Tyr Phe Asp His Ile Asp Ile
1               5

<210> SEQ ID NO 29
<211> LENGTH: 12
<212> TYPE: PRT
<213> ORGANISM: Artificial sequence
<220> FEATURE:
<223> OTHER INFORMATION: Synthetic sequence: H-CDR 3

<400> SEQUENCE: 29

Met Glu Tyr Trp Tyr His Leu Leu Tyr Met Asp Tyr
1               5                   10

<210> SEQ ID NO 30
<211> LENGTH: 9
<212> TYPE: PRT
<213> ORGANISM: Artificial sequence
<220> FEATURE:
<223> OTHER INFORMATION: Synthetic sequence: H-CDR 3

<400> SEQUENCE: 30

Tyr Tyr Gly Tyr Ser Tyr Met Asp Tyr
1               5

<210> SEQ ID NO 31
<211> LENGTH: 8
<212> TYPE: PRT
<213> ORGANISM: Artificial sequence
<220> FEATURE:
<223> OTHER INFORMATION: Synthetic sequence: H-CDR 3

<400> SEQUENCE: 31

Asp Gly Gly Trp Tyr Ile Asp Val
1               5

<210> SEQ ID NO 32
<211> LENGTH: 11
<212> TYPE: PRT
<213> ORGANISM: Artificial sequence
<220> FEATURE:
<223> OTHER INFORMATION: Synthetic sequence: VL Kappa CDR 1

<400> SEQUENCE: 32

Arg Ala Ser Gln Gly Ile Ser Ser Tyr Leu Ala
1               5                   10

<210> SEQ ID NO 33
```

```
<211> LENGTH: 11
<212> TYPE: PRT
<213> ORGANISM: Artificial sequence
<220> FEATURE:
<223> OTHER INFORMATION: Synthetic sequence: VL Kappa CDR 1

<400> SEQUENCE: 33

Arg Ala Ser Gln Asp Ile Tyr Asn Tyr Leu Asn
1               5                   10

<210> SEQ ID NO 34
<211> LENGTH: 11
<212> TYPE: PRT
<213> ORGANISM: Artificial sequence
<220> FEATURE:
<223> OTHER INFORMATION: Synthetic sequence: VL Kappa CDR 1

<400> SEQUENCE: 34

Arg Ala Ser Gln Asp Ile Ser Ile Ser Leu Thr
1               5                   10

<210> SEQ ID NO 35
<211> LENGTH: 12
<212> TYPE: PRT
<213> ORGANISM: Artificial sequence
<220> FEATURE:
<223> OTHER INFORMATION: Synthetic sequence: VL Kappa CDR 1

<400> SEQUENCE: 35

Arg Ala Ser Gln Ser Val Ser Ser Ser Tyr Leu Ala
1               5                   10

<210> SEQ ID NO 36
<211> LENGTH: 12
<212> TYPE: PRT
<213> ORGANISM: Artificial sequence
<220> FEATURE:
<223> OTHER INFORMATION: Synthetic sequence: VL Kappa CDR 1

<400> SEQUENCE: 36

Arg Ala Ser Gln Ser Ile Gly Asp Asn Tyr Leu Ala
1               5                   10

<210> SEQ ID NO 37
<211> LENGTH: 11
<212> TYPE: PRT
<213> ORGANISM: Artificial sequence
<220> FEATURE:
<223> OTHER INFORMATION: Synthetic sequence: VL Lamda CDR 1

<400> SEQUENCE: 37

Ser Gly Asp Ala Leu Gly Asp Lys Tyr Ala Ser
1               5                   10

<210> SEQ ID NO 38
<211> LENGTH: 11
<212> TYPE: PRT
<213> ORGANISM: Artificial sequence
<220> FEATURE:
<223> OTHER INFORMATION: Synthetic sequence: VL Lamda CDR 1

<400> SEQUENCE: 38

Gly Gly Asp Ser Leu Gly Gly Lys Tyr Val Tyr
1               5                   10

<210> SEQ ID NO 39
<211> LENGTH: 11
<212> TYPE: PRT
```

```
<213> ORGANISM: Artificial sequence
<220> FEATURE:
<223> OTHER INFORMATION: Synthetic sequence: VL Lamda CDR 1

<400> SEQUENCE: 39

Ser Gly Asp Asn Leu Gly Ser Lys Tyr Val His
1               5                   10

<210> SEQ ID NO 40
<211> LENGTH: 11
<212> TYPE: PRT
<213> ORGANISM: Artificial sequence
<220> FEATURE:
<223> OTHER INFORMATION: Synthetic sequence: VL Lamda CDR 1

<400> SEQUENCE: 40

Ser Gly Asp Asn Leu Gly Ser Tyr Tyr Ala Asn
1               5                   10

<210> SEQ ID NO 41
<211> LENGTH: 7
<212> TYPE: PRT
<213> ORGANISM: Artificial sequence
<220> FEATURE:
<223> OTHER INFORMATION: Synthetic sequence: VL Kappa CDR 2

<400> SEQUENCE: 41

Ala Ala Ser Ser Leu Gln Ser
1               5

<210> SEQ ID NO 42
<211> LENGTH: 7
<212> TYPE: PRT
<213> ORGANISM: Artificial sequence
<220> FEATURE:
<223> OTHER INFORMATION: Synthetic sequence: VL Kappa CDR 2

<400> SEQUENCE: 42

Gly Ala Ser Ser Leu Gln Ser
1               5

<210> SEQ ID NO 43
<211> LENGTH: 7
<212> TYPE: PRT
<213> ORGANISM: Artificial sequence
<220> FEATURE:
<223> OTHER INFORMATION: Synthetic sequence: VL Kappa CDR 2

<400> SEQUENCE: 43

Gly Ala Phe Ser Leu Gln Ser
1               5

<210> SEQ ID NO 44
<211> LENGTH: 7
<212> TYPE: PRT
<213> ORGANISM: Artificial sequence
<220> FEATURE:
<223> OTHER INFORMATION: Synthetic sequence: VL Kappa CDR 2

<400> SEQUENCE: 44

Gly Ala Ser Ser Arg Ala Thr
1               5

<210> SEQ ID NO 45
<211> LENGTH: 7
<212> TYPE: PRT
<213> ORGANISM: Artificial sequence
<220> FEATURE:
```

<223> OTHER INFORMATION: Synthetic sequence: VL Kappa CDR 2

<400> SEQUENCE: 45

Asp Ala Asn Asn Arg Ala Thr
1               5

<210> SEQ ID NO 46
<211> LENGTH: 7
<212> TYPE: PRT
<213> ORGANISM: Artificial sequence
<220> FEATURE:
<223> OTHER INFORMATION: Synthetic sequence: VL Lamda CDR 2

<400> SEQUENCE: 46

Asp Asp Ser Asp Arg Pro Ser
1               5

<210> SEQ ID NO 47
<211> LENGTH: 7
<212> TYPE: PRT
<213> ORGANISM: Artificial sequence
<220> FEATURE:
<223> OTHER INFORMATION: Synthetic sequence: VL Lamda CDR 2

<400> SEQUENCE: 47

Gly Asp Ser Lys Arg Pro Ser
1               5

<210> SEQ ID NO 48
<211> LENGTH: 7
<212> TYPE: PRT
<213> ORGANISM: Artificial sequence
<220> FEATURE:
<223> OTHER INFORMATION: Synthetic sequence: VL Lamda CDR 2

<400> SEQUENCE: 48

Ala Asp Asn Asn Arg Pro Ser
1               5

<210> SEQ ID NO 49
<211> LENGTH: 6
<212> TYPE: PRT
<213> ORGANISM: Artificial sequence
<220> FEATURE:
<223> OTHER INFORMATION: Synthetic sequence: VL Lamda CDR 2

<400> SEQUENCE: 49

Glu Asp Lys Arg Pro Ser
1               5

<210> SEQ ID NO 50
<211> LENGTH: 8
<212> TYPE: PRT
<213> ORGANISM: Artificial sequence
<220> FEATURE:
<223> OTHER INFORMATION: Synthetic sequence: VL Kappa CDR 3

<400> SEQUENCE: 50

Gln Gln Gln Asn Asp Tyr Pro Leu
1               5

<210> SEQ ID NO 51
<211> LENGTH: 8
<212> TYPE: PRT
<213> ORGANISM: Artificial sequence
<220> FEATURE:
<223> OTHER INFORMATION: Synthetic sequence: VL Kappa CDR 3

```
<400> SEQUENCE: 51

Gln Gln Tyr Tyr Gly Thr Ser Ala
1               5

<210> SEQ ID NO 52
<211> LENGTH: 8
<212> TYPE: PRT
<213> ORGANISM: Artificial sequence
<220> FEATURE:
<223> OTHER INFORMATION: Synthetic sequence: VL Kappa CDR 3

<400> SEQUENCE: 52

Gln Gln Phe Tyr Phe His Ser Pro
1               5

<210> SEQ ID NO 53
<211> LENGTH: 8
<212> TYPE: PRT
<213> ORGANISM: Artificial sequence
<220> FEATURE:
<223> OTHER INFORMATION: Synthetic sequence: VL Kappa CDR 3

<400> SEQUENCE: 53

Gln Gln Phe Trp Phe Glu Pro Val
1               5

<210> SEQ ID NO 54
<211> LENGTH: 8
<212> TYPE: PRT
<213> ORGANISM: Artificial sequence
<220> FEATURE:
<223> OTHER INFORMATION: Synthetic sequence: VL Kappa CDR 3

<400> SEQUENCE: 54

Gln Gln Phe Trp Phe His Pro Val
1               5

<210> SEQ ID NO 55
<211> LENGTH: 8
<212> TYPE: PRT
<213> ORGANISM: Artificial sequence
<220> FEATURE:
<223> OTHER INFORMATION: Synthetic sequence: VL Kappa CDR 3

<400> SEQUENCE: 55

Gln Gln Phe Trp Ser Glu Pro Val
1               5

<210> SEQ ID NO 56
<211> LENGTH: 8
<212> TYPE: PRT
<213> ORGANISM: Artificial sequence
<220> FEATURE:
<223> OTHER INFORMATION: Synthetic sequence: VL Kappa CDR 3

<400> SEQUENCE: 56

Gln Gln Phe Trp Thr Glu Pro Val
1               5

<210> SEQ ID NO 57
<211> LENGTH: 8
<212> TYPE: PRT
<213> ORGANISM: Artificial sequence
<220> FEATURE:
<223> OTHER INFORMATION: Synthetic sequence: VL Kappa CDR 3

<400> SEQUENCE: 57
```

```
Gln Gln Tyr Asp Asp His Pro Leu
1               5

<210> SEQ ID NO 58
<211> LENGTH: 9
<212> TYPE: PRT
<213> ORGANISM: Artificial sequence
<220> FEATURE:
<223> OTHER INFORMATION: Synthetic sequence: VL Lamda CDR 3

<400> SEQUENCE: 58

Gln Ser Tyr Thr Asn Ala Leu Ser Thr
1               5

<210> SEQ ID NO 59
<211> LENGTH: 10
<212> TYPE: PRT
<213> ORGANISM: Artificial sequence
<220> FEATURE:
<223> OTHER INFORMATION: Synthetic sequence: VL Lamda CDR 3

<400> SEQUENCE: 59

Gln Ser Tyr Asp Leu Gln Ser Leu Asn Ile
1               5                   10

<210> SEQ ID NO 60
<211> LENGTH: 10
<212> TYPE: PRT
<213> ORGANISM: Artificial sequence
<220> FEATURE:
<223> OTHER INFORMATION: Synthetic sequence: VL Lamda CDR 3

<400> SEQUENCE: 60

Gln Ser Tyr Asp Leu Lys Ser Leu Asn Val
1               5                   10

<210> SEQ ID NO 61
<211> LENGTH: 10
<212> TYPE: PRT
<213> ORGANISM: Artificial sequence
<220> FEATURE:
<223> OTHER INFORMATION: Synthetic sequence: VL Lamda CDR 3

<400> SEQUENCE: 61

Gln Ser Tyr Asp Leu Gly Ser Leu Asn Leu
1               5                   10

<210> SEQ ID NO 62
<211> LENGTH: 8
<212> TYPE: PRT
<213> ORGANISM: Artificial sequence
<220> FEATURE:
<223> OTHER INFORMATION: Synthetic sequence: VL Lamda CDR 3

<400> SEQUENCE: 62

Gln Ser Tyr Asp His Met Leu Gln
1               5

<210> SEQ ID NO 63
<211> LENGTH: 9
<212> TYPE: PRT
<213> ORGANISM: Artificial sequence
<220> FEATURE:
<223> OTHER INFORMATION: Synthetic sequence: VL Lamda CDR 3

<400> SEQUENCE: 63

Ser Ser Tyr Asp Ser Asn Ser Ile Arg
1               5
```

```
<210> SEQ ID NO 64
<211> LENGTH: 9
<212> TYPE: PRT
<213> ORGANISM: Artificial sequence
<220> FEATURE:
<223> OTHER INFORMATION: Synthetic sequence: VL Lamda CDR 3

<400> SEQUENCE: 64

Ser Ser Tyr Asp Leu Asp Gly Val Arg
1               5

<210> SEQ ID NO 65
<211> LENGTH: 9
<212> TYPE: PRT
<213> ORGANISM: Artificial sequence
<220> FEATURE:
<223> OTHER INFORMATION: Synthetic sequence: VL Lamda CDR 3

<400> SEQUENCE: 65

Ser Ser Tyr Thr Thr Ser Gly Ile Arg
1               5

<210> SEQ ID NO 66
<211> LENGTH: 10
<212> TYPE: PRT
<213> ORGANISM: Artificial sequence
<220> FEATURE:
<223> OTHER INFORMATION: Synthetic sequence: VL Lamda CDR 3

<400> SEQUENCE: 66

Gln Ser Phe Asp Ser Tyr His Ser Asp Tyr
1               5                   10

<210> SEQ ID NO 67
<211> LENGTH: 120
<212> TYPE: PRT
<213> ORGANISM: Artificial sequence
<220> FEATURE:
<223> OTHER INFORMATION: Synthetic sequence: HuCAL GOLD anti-TSLP
      antibody MOR04493 VH

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Asp Phe Gly Trp Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Met Phe Tyr Ser Ile Leu Phe Asp Tyr Trp Gly Gln
            100                 105                 110

Gly Thr Leu Val Thr Val Ser Ser
        115                 120

<210> SEQ ID NO 68
<211> LENGTH: 109
<212> TYPE: PRT
<213> ORGANISM: Artificial sequence
```

```
<220> FEATURE:
<223> OTHER INFORMATION: Synthetic sequence: HuCAL GOLD anti-TSLP
      antibodies MOR04493 VL, MOR05008 VL, and MOR05009 VL

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Tyr Asn Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Gln Asn Asp Tyr Pro Leu
                85                  90                  95

Thr Phe Gly Gln Gly Thr Lys Val Glu Ile Lys Arg Thr
            100                 105

<210> SEQ ID NO 69
<211> LENGTH: 118
<212> TYPE: PRT
<213> ORGANISM: Artificial sequence
<220> FEATURE:
<223> OTHER INFORMATION: Synthetic sequence: HuCAL GOLD anti-TSLP
      antibodies MOR04494 VH, MOR05016 VH, MOR05017 VH, and MOR05018 VH

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Asn Ile Ser Tyr Asp Ser Ser Asp Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Gln Tyr Phe Asp His Ile Asp Ile Trp Gly Gln Gly Thr
            100                 105                 110

Leu Val Thr Val Ser Ser
        115

<210> SEQ ID NO 70
<211> LENGTH: 109
<212> TYPE: PRT
<213> ORGANISM: Artificial sequence
<220> FEATURE:
<223> OTHER INFORMATION: Synthetic sequence: HuCAL GOLD anti-TSLP
      antibodies MOR04494 VL, MOR05010 VL, MOR05011 VL, MOR05012 VL,
      MOR05013 VL, MOR05014 VL, and MOR05015 VL

<400> SEQUENCE: 70

Asp Ile Glu Leu Thr Gln Pro Pro Ser Val Ser Val Ala Pro Gly Gln
1               5                   10                  15

Thr Ala Arg Ile Ser Cys Gly Gly Asp Ser Leu Gly Gly Lys Tyr Val
            20                  25                  30
```

-continued

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
 50                      55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Thr Asn Ala Leu Ser Thr
                85                  90                  95

Val Phe Gly Gly Gly Thr Lys Leu Thr Val Leu Gly Gln
            100                 105

<210> SEQ ID NO 71
<211> LENGTH: 121
<212> TYPE: PRT
<213> ORGANISM: Artificial sequence
<220> FEATURE:
<223> OTHER INFORMATION: Synthetic sequence: HuCAL GOLD anti-TSLP
      antibody MOR04496 VH

<400> SEQUENCE: 71

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ser Ile Ser Tyr Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Glu Tyr Trp Tyr His Leu Leu Tyr Met Asp Tyr Trp Gly
            100                 105                 110

Gln Gly Thr Leu Val Thr Val Ser Ser
        115                 120

<210> SEQ ID NO 72
<211> LENGTH: 110
<212> TYPE: PRT
<213> ORGANISM: Artificial sequence
<220> FEATURE:
<223> OTHER INFORMATION: Synthetic sequence: HuCAL GOLD anti-TSLP
      antibody MOR04496 VL

<400> SEQUENCE: 72

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Asn
            20                  25                  30

Tyr Leu Ala Trp Tyr Gln Gln Lys Pro Gly Gln Ala Pro Arg Leu Leu
        35                  40                  45

Ile Tyr Asp Ala Asn Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Asp Asp His Pro
                85                  90                  95

Leu Thr Phe Gly Gln Gly Thr Lys Val Glu Ile Lys Arg Thr

<210> SEQ ID NO 73
<211> LENGTH: 118
<212> TYPE: PRT
<213> ORGANISM: Artificial sequence
<220> FEATURE:
<223> OTHER INFORMATION: Synthetic sequence: HuCAL GOLD anti-TSLP
    antibodies MOR04497 VH, MOR05020 VH, MOR05021 VH, and MOR05022 VH,

<400> SEQUENCE: 73

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Ala Leu Ser Trp Val Arg Gln Ala Pro Gly Lys Gly Leu Glu Trp Val
        35                  40                  45

Ser Gly Ile Gln Tyr Asp Gly Ser Asn Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Tyr Ser Tyr Met Asp Tyr Trp Gly Gln Gly Thr
            100                 105                 110

Leu Val Thr Val Ser Ser
        115

<210> SEQ ID NO 74
<211> LENGTH: 108
<212> TYPE: PRT
<213> ORGANISM: Artificial sequence
<220> FEATURE:
<223> OTHER INFORMATION: Synthetic sequence: HuCAL GOLD anti-TSLP
    antibodies MOR04497 VL and MOR05019 VL

<400> SEQUENCE: 74

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

His Trp Tyr Gln Gln Lys Pro Gly Gln Ala Pro Val Leu Val Ile Tyr
        35                  40                  45

Ala Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp His Met Leu Gln Val
                85                  90                  95

Phe Gly Gly Gly Thr Lys Leu Thr Val Leu Gly Gln
            100                 105

<210> SEQ ID NO 75
<211> LENGTH: 120
<212> TYPE: PRT
<213> ORGANISM: Artificial sequence
<220> FEATURE:
<223> OTHER INFORMATION: Synthetic sequence: HuCAL GOLD anti-TSLP
    antibody MOR04609 VH

<400> SEQUENCE: 75

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Leu Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gly Trp Tyr Ile Asp Val Trp Gly Gln
            100                 105                 110

Gly Thr Leu Val Thr Val Ser Ser
            115                 120

<210> SEQ ID NO 76
<211> LENGTH: 109
<212> TYPE: PRT
<213> ORGANISM: Artificial sequence
<220> FEATURE:
<223> OTHER INFORMATION: Synthetic sequence: HuCAL GOLD anti-TSLP
      antibody MOR04609 VL

<400> SEQUENCE: 76

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Tyr Tyr Ala
            20                  25                  30

Asn Trp Tyr Gln Gln Lys Pro Gly Gln Ala Pro Val Leu Val Ile Tyr
        35                  40                  45

Glu Asp Lys Arg Pro Ser Gly Ile Pro Glu Arg Phe Ser Gly Ser Asn
    50                  55                  60

Ser Gly Asn Thr Ala Thr Leu Thr Ile Ser Gly Thr Gln Ala Glu Asp
65                  70                  75                  80

Glu Ala Asp Tyr Tyr Cys Gln Ser Phe Asp Ser Tyr His Ser Asp Tyr
                85                  90                  95

Val Phe Gly Gly Gly Thr Lys Leu Thr Val Leu Gly Gln
            100                 105

<210> SEQ ID NO 77
<211> LENGTH: 124
<212> TYPE: PRT
<213> ORGANISM: Artificial sequence
<220> FEATURE:
<223> OTHER INFORMATION: Synthetic sequence: HuCAL GOLD anti-TSLP
      antibodies MOR04832 VH, MOR05023 VH, MOR05024 VH, MOR05025 VH,
      MOR05026 VH, and MOR05027 VH

<400> SEQUENCE: 77

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Asn Ile Tyr Pro Ile Phe Gly Tyr Ala Asn Tyr Ala Gln Lys Phe
    50                  55                  60
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Gln Tyr Gly Gln His Phe Ser His Gly Gly Met Asp
            100                 105                 110

Val Trp Gly Gln Gly Thr Leu Val Thr Val Ser Ser
        115                 120

<210> SEQ ID NO 78
<211> LENGTH: 109
<212> TYPE: PRT
<213> ORGANISM: Artificial sequence
<220> FEATURE:
<223> OTHER INFORMATION: Synthetic sequence: HuCAL GOLD anti-TSLP
      antibody MOR04832 VL

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ile Ser
            20                  25                  30

Leu Thr Trp Tyr Gln Gln Lys Pro Gly Lys Ala Pro Lys Leu Leu Ile
        35                  40                  45

Tyr Gly Ala Phe Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Thr Ser Ala
                85                  90                  95

Thr Phe Gly Gln Gly Thr Lys Val Glu Ile Lys Arg Thr
            100                 105

<210> SEQ ID NO 79
<211> LENGTH: 120
<212> TYPE: PRT
<213> ORGANISM: Artificial sequence
<220> FEATURE:
<223> OTHER INFORMATION: Synthetic sequence: HuCAL GOLD anti-TSLP
      antibody MOR05008 VH

<400> SEQUENCE: 79

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Glu Phe Gly Phe Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Met Phe Tyr Ser Ile Leu Phe Asp Tyr Trp Gly Gln
            100                 105                 110

Gly Thr Leu Val Thr Val Ser Ser
        115                 120

-continued

```
<210> SEQ ID NO 80
<211> LENGTH: 120
<212> TYPE: PRT
<213> ORGANISM: Artificial sequence
<220> FEATURE:
<223> OTHER INFORMATION: Synthetic sequence: HuCAL GOLD anti-TSLP
      antibody MOR05009 VH

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly His Ile Ser Pro Glu Phe Gly Phe Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Met Phe Tyr Ser Ile Leu Phe Asp Tyr Trp Gly Gln
            100                 105                 110

Gly Thr Leu Val Thr Val Ser Ser
        115                 120

<210> SEQ ID NO 81
<211> LENGTH: 117
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05010 VH, MOR05154 VH, MOR05155 VH, and MOR05156 VH

<400> SEQUENCE: 81

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Phe Phe Asp Gly Glu Thr Tyr Tyr Ala Gly Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Gln Tyr Phe Asp His Ile Asp Ile Trp Gly Gln Gly Thr Leu
            100                 105                 110

Val Thr Val Ser Ser
        115

<210> SEQ ID NO 82
<211> LENGTH: 117
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05011 VH, MOR05157 VH, MOR05158 VH, and MOR05159 VH

<400> SEQUENCE: 82
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
            35                  40                  45

Ser Gly Ile Phe Tyr Asp Gly Ser Thr Tyr Tyr Pro Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Gln Tyr Phe Asp His Ile Asp Ile Trp Gly Gln Gly Thr Leu
            100                 105                 110

Val Thr Val Ser Ser
            115

<210> SEQ ID NO 83
<211> LENGTH: 117
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05012 VH, MOR05160 VH, MOR05161 VH, and MOR05162 VH

<400> SEQUENCE: 83

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
            35                  40                  45

Ser Gly Ile Phe Phe Thr Gly Glu Thr Tyr Tyr Pro Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Gln Tyr Phe Asp His Ile Asp Ile Trp Gly Gln Gly Thr Leu
            100                 105                 110

Val Thr Val Ser Ser
            115

<210> SEQ ID NO 84
<211> LENGTH: 117
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05013 VH, MOR05163 VH, MOR05164 VH, and MOR05165 VH

<400> SEQUENCE: 84

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
            35                  40                  45

Ser Gly Ile Phe Phe Asp Gly Glu Thr Tyr Tyr Ala Asp Ser Val Lys

```
                    50                  55                  60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gln Gln Tyr Phe Asp His Ile Asp Ile Trp Gly Gln Gly Thr Leu
            100                 105                 110

Val Thr Val Ser Ser
        115

<210> SEQ ID NO 85
<211> LENGTH: 117
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05014 VH, MOR05166 VH, MOR05167 VH, and MOR05168 VH

<400> SEQUENCE: 85

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Tyr Met Ser Trp Val Arg Gln Ala Pro Gly Lys Gly Leu Glu Trp Val
             35                  40                  45

Ser Gly Ile Phe Phe Asp Gly Thr Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gln Gln Tyr Phe Asp His Ile Asp Ile Trp Gly Gln Gly Thr Leu
            100                 105                 110

Val Thr Val Ser Ser
        115

<210> SEQ ID NO 86
<211> LENGTH: 117
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05015 VH, MOR05169 VH, MOR05170 VH, and MOR05171 VH

<400> SEQUENCE: 86

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Tyr Met Ser Trp Val Arg Gln Ala Pro Gly Lys Gly Leu Glu Trp Val
             35                  40                  45

Ser Gly Thr Phe Phe Asp Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gln Gln Tyr Phe Asp His Ile Asp Ile Trp Gly Gln Gly Thr Leu
            100                 105                 110
```

<210> SEQ ID NO 87
<211> LENGTH: 110
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05016 VL, MOR05154 VL, MOR05157 VL, MOR05160 VL,
      MOR05163 VL, MOR05166 VL, and MOR05169 VL

<400> SEQUENCE: 87

Asp Ile Glu Leu Thr Gln Pro Pro Ser Val Ser Val Ala Pro Gly Gln
1               5                   10                  15

Thr Ala Arg Ile Ser Cys Gly Gly Asp Ser Leu Gly Gly Lys Tyr Val
            20                  25                  30

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Leu Gln Ser Leu Asn
                85                  90                  95

Ile Val Phe Gly Gly Gly Thr Lys Leu Thr Val Leu Gly Gln
            100                 105                 110

<210> SEQ ID NO 88
<211> LENGTH: 110
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05017 VL, MOR05155 VL, MOR05158 VL, MOR05161 VL,
      MOR05164 VL, MOR05167 VL, and MOR05170 VL

<400> SEQUENCE: 88

Asp Ile Glu Leu Thr Gln Pro Pro Ser Val Ser Val Ala Pro Gly Gln
1               5                   10                  15

Thr Ala Arg Ile Ser Cys Gly Gly Asp Ser Leu Gly Gly Lys Tyr Val
            20                  25                  30

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Leu Lys Ser Leu Asn
                85                  90                  95

Val Val Phe Gly Gly Gly Thr Lys Leu Thr Val Leu Gly Gln
            100                 105                 110

<210> SEQ ID NO 89
<211> LENGTH: 110
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05018 VL, MOR05156 VL, MOR05159 VL, MOR05162 VL,
      MOR05165 VL, MOR05168 VL, and MOR05171 VL -continued

<400> SEQUENCE: 89

Asp Ile Glu Leu Thr Gln Pro Pro Ser Val Ser Val Ala Pro Gly Gln
1               5                   10                  15

Thr Ala Arg Ile Ser Cys Gly Gly Asp Ser Leu Gly Gly Lys Tyr Val
            20                  25                  30

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Leu Gly Ser Leu Asn
                85                  90                  95

Leu Val Phe Gly Gly Gly Thr Lys Leu Thr Val Leu Gly Gln
            100                 105                 110

<210> SEQ ID NO 90
<211> LENGTH: 117
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05019 VH, MOR05172 VH, MOR05173 VH, and MOR05174 VH

<400> SEQUENCE: 90

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Ala Leu Ser Trp Val Arg Gln Ala Pro Gly Lys Gly Leu Glu Trp Val
        35                  40                  45

Ser Val Ile Ser Phe Asp Gly Val Lys Phe Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Tyr Gly Tyr Ser Tyr Met Asp Tyr Trp Gly Gln Gly Thr Leu
            100                 105                 110

Val Thr Val Ser Ser
        115

<210> SEQ ID NO 91
<211> LENGTH: 109
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05020 VL and MOR05172 VL

<400> SEQUENCE: 91

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

His Trp Tyr Gln Gln Lys Pro Gly Gln Ala Pro Val Leu Val Ile Tyr
        35                  40                  45

Ala Asp Asn Asn Arg Pro Ser Gly Ile Pro Glu Arg Phe Ser Gly Ser
50                  55                  60

```
Asn Ser Gly Asn Thr Ala Thr Leu Thr Ile Ser Gly Thr Gln Ala Glu
 65                  70                  75                  80

Asp Glu Ala Asp Tyr Tyr Cys Ser Ser Tyr Asp Ser Asn Ser Ile Arg
                 85                  90                  95

Val Phe Gly Gly Gly Thr Lys Leu Thr Val Leu Gly Gln
            100                 105

<210> SEQ ID NO 92
<211> LENGTH: 109
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05021 VL and MOR05173 VL

<400> SEQUENCE: 92

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Gly Ser Lys Tyr Val
             20                  25                  30

His Trp Tyr Gln Gln Lys Pro Gly Gln Ala Pro Val Leu Val Ile Tyr
             35                  40                  45

Ala Asp Asn Asn Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Ser Tyr Leu Asp Gly Val Arg
                 85                  90                  95

Val Phe Gly Gly Gly Thr Lys Leu Thr Val Leu Gly Gln
            100                 105

<210> SEQ ID NO 93
<211> LENGTH: 109
<212> TYPE: PRT
<213> ORGANISM: Artificial sequence
<220> FEATURE:
<223> OTHER INFORMATION: Synthetic sequence: HuCAL GOLD anti-TSLP
      antibodies MOR05022 VL and MOR05174 VL

<400> SEQUENCE: 93

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Gly Ser Lys Tyr Val
             20                  25                  30

His Trp Tyr Gln Gln Lys Pro Gly Gln Ala Pro Val Leu Val Ile Tyr
             35                  40                  45

Ala Asp Asn Asn Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Ser Tyr Thr Thr Ser Gly Ile Arg
                 85                  90                  95

Val Phe Gly Gly Gly Thr Lys Leu Thr Val Leu Gly Gln
            100                 105

<210> SEQ ID NO 94
<211> LENGTH: 109
<212> TYPE: PRT
<213> ORGANISM: Artificial sequence
<220> FEATURE:
```

-continued

<223> OTHER INFORMATION: Synthetic sequence: HuCAL GOLD anti-TSLP
      antibody MOR05023 VL

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ile Ser
            20                  25                  30

Leu Thr Trp Tyr Gln Gln Lys Pro Gly Lys Ala Pro Lys Leu Leu Ile
        35                  40                  45

Tyr Gly Ala Phe Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Phe His Ser Pro
                85                  90                  95

Thr Phe Gly Gln Gly Thr Lys Val Glu Ile Lys Arg Thr
            100                 105

<210> SEQ ID NO 95
<211> LENGTH: 109
<212> TYPE: PRT
<213> ORGANISM: Artificial sequence
<220> FEATURE:
<223> OTHER INFORMATION: Synthetic sequence: HuCAL GOLD anti-TSLP
      antibody MOR05024 VL

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ile Ser
            20                  25                  30

Leu Thr Trp Tyr Gln Gln Lys Pro Gly Lys Ala Pro Lys Leu Leu Ile
        35                  40                  45

Tyr Gly Ala Phe Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Trp Phe Glu Pro Val
                85                  90                  95

Thr Phe Gly Gln Gly Thr Lys Val Glu Ile Lys Arg Thr
            100                 105

<210> SEQ ID NO 96
<211> LENGTH: 109
<212> TYPE: PRT
<213> ORGANISM: Artificial sequence
<220> FEATURE:
<223> OTHER INFORMATION: Synthetic sequence: HuCAL GOLD anti-TSLP
      antibody MOR05025 VL

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ile Ser
            20                  25                  30

Leu Thr Trp Tyr Gln Gln Lys Pro Gly Lys Ala Pro Lys Leu Leu Ile
        35                  40                  45

Tyr Gly Ala Phe Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Trp Phe His Pro Val
                 85                  90                  95

Thr Phe Gly Gln Gly Thr Lys Val Glu Ile Lys Arg Thr
            100                 105

<210> SEQ ID NO 97
<211> LENGTH: 109
<212> TYPE: PRT
<213> ORGANISM: Artificial sequence
<220> FEATURE:
<223> OTHER INFORMATION: Synthetic sequence: HuCAL GOLD anti-TSLP
      antibody MOR05026 VL

<400> SEQUENCE: 97

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Ile Ser
                 20                  25                  30

Leu Thr Trp Tyr Gln Gln Lys Pro Gly Lys Ala Pro Lys Leu Leu Ile
             35                  40                  45

Tyr Gly Ala Phe Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Trp Ser Glu Pro Val
                 85                  90                  95

Thr Phe Gly Gln Gly Thr Lys Val Glu Ile Lys Arg Thr
            100                 105

<210> SEQ ID NO 98
<211> LENGTH: 109
<212> TYPE: PRT
<213> ORGANISM: Artificial sequence
<220> FEATURE:
<223> OTHER INFORMATION: Synthetic sequence: HuCAL GOLD anti-TSLP
      antibody MOR05027 VL

<400> SEQUENCE: 98

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Ile Ser
                 20                  25                  30

Leu Thr Trp Tyr Gln Gln Lys Pro Gly Lys Ala Pro Lys Leu Leu Ile
             35                  40                  45

Tyr Gly Ala Phe Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Trp Thr Glu Pro Val
                 85                  90                  95

Thr Phe Gly Gln Gly Thr Lys Val Glu Ile Lys Arg Thr
            100                 105

<210> SEQ ID NO 99
<211> LENGTH: 233
<212> TYPE: PRT
<213> ORGANISM: Artificial sequence
<220> FEATURE:
```

<223> OTHER INFORMATION: Synthetic sequence: MOR 5164, 5167, 5170 Light
Chain Lambda

<400> SEQUENCE: 99

Met Ala Trp Ala Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
            20                  25                  30

Pro Gly Gln Thr Ala Arg Ile Ser Cys Gly Gly Asp Ser Leu Gly Gly
        35                  40                  45

Lys Tyr Val Tyr Trp Tyr Gln Gln Lys Pro Gly Gln Ala Pro Val Leu
    50                  55                  60

Val Ile Tyr Gly Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Gln Ser Tyr Asp Leu Lys
            100                 105                 110

Ser Leu Asn Val Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 100
<211> LENGTH: 699
<212> TYPE: DNA
<213> ORGANISM: Artificial sequence
<220> FEATURE:
<223> OTHER INFORMATION: Synthetic sequence: Sequence encoding SEQ ID
NO: 99

<400> SEQUENCE: 100
atggcctggg ctctgctgct cctcaccctc ctcactcagg gcacaggatc ctgggctgat      60
atcgaactga cccagccgcc ttcagtgagc gttgcaccag tcagaccgc gcgtatctcg      120 tgtggcggcg attctcttgg tggtaagtat gtttattggt accagcagaa acccgggcag     180
gcgccagttc ttgtgattta tggtgattct aagcgtccct caggcatccc ggaacgcttt     240
agcggatcca acagcggcaa caccgcgacc ctgaccatta gcggcactca ggcggaagac     300
gaagcggatt attattgcca gtcttatgat cttaagtctc ttaatgttgt gtttggcggc     360
ggcacgaagt taccgtcct aggtcagccc aaggctgccc cctcggtcac tctgttcccg     420
ccctcctctg aggagcttca agccaacaag gccacactgg tgtgtctcat aagtgacttc     480
tacccgggag ccgtgacagt ggcctggaag gcagatagca gccccgtcaa ggcgggagtg     540
gagaccacca cacctccaa acaaagcaac aacaagtacg cggccagcag ctatctgagc     600
ctgacgcctg agcagtggaa gtcccacaga agctacagct gccaggtcac gcatgaaggg        660
agcaccgtgg agaagacagt ggcccctaca gaatgttca                               699

<210> SEQ ID NO 101
<211> LENGTH: 234
<212> TYPE: PRT
<213> ORGANISM: Artificial sequence
<220> FEATURE:
<223> OTHER INFORMATION: Synthetic sequence: MOR 5164, 5167, 5170 Light
      Chain Lambda (Optimized)

<400> SEQUENCE: 101

Met Ser Val Leu Thr Gln Val Leu Ala Leu Leu Leu Trp Leu Thr
1               5                   10                  15

Gly Thr Arg Cys Asp Ile Glu Leu Thr Gln Pro Pro Ser Val Ser Val
            20                  25                  30

Ala Pro Gly Gln Thr Ala Arg Ile Ser Cys Gly Gly Asp Ser Leu Gly
        35                  40                  45

Gly Lys Tyr Val Tyr Trp Tyr Gln Gln Lys Pro Gly Gln Ala Pro Val
    50                  55                  60

Leu Val Ile Tyr Gly Asp Ser Lys Arg Pro Ser Gly Ile Pro Glu Arg
65                  70                  75                  80

Phe Ser Gly Ser Asn Ser Gly Asn Thr Ala Thr Leu Thr Ile Ser Gly
                85                  90                  95

Thr Gln Ala Glu Asp Glu Ala Asp Tyr Tyr Cys Gln Ser Tyr Asp Leu
            100                 105                 110

Lys Ser Leu Asn Val Val Phe Gly Gly Gly Thr Lys Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 102
<211> LENGTH: 705
<212> TYPE: DNA
<213> ORGANISM: Artificial sequence
<220> FEATURE:
<223> OTHER INFORMATION: Synthetic sequence: Sequence encoding SEQ ID
      NO: 101

<400> SEQUENCE: 102
atgagtgtgc tcactcaggt cctggcgttg ctgctgctgt ggcttacagg tacgcgttgc        60
gacatcgagc tgacccagcc ccccagcgtg tctgtggccc ctggccagac cgcccggatc       120
agctgtggcg gcgacagcct gggcggcaag tacgtgtact ggtatcagca gaagcccggc       180
caggcccccg tgctggtgat ctacggcgac agcaagcggc ccagcggcat ccccgagcgg       240

-continued

```
ttcagcggca gcaacagcgg caacaccgcc accctgacca tcagcggcac ccaggccgag    300
gacgaggccg actactactg ccagagctac gacctgaaga gcctgaacgt ggtgtttggc    360
ggcggaacaa agcttaccgt cctaggtcag cccaaggctg ccccctcggt cactctgttc    420
ccgccctcct ctgaggagct tcaagccaac aaggccacac tggtgtgtct cataagtgac    480
ttctacccgg gagccgtgac agtggcctgg aaggcagata gcagcccgt caaggcggga    540 gtggagacaa ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggaaaagac agtggcccct acagaatgtt catag                    705
```

<210> SEQ ID NO 103
<211> LENGTH: 466
<212> TYPE: PRT
<213> ORGANISM: Artificial sequence
<220> FEATURE:
<223> OTHER INFORMATION: Synthetic sequence: MOR5164 Heavy Chain IgG1

<400> SEQUENCE: 103

```
Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Tyr Tyr Met Ser Trp Val Arg Gln Ala Pro Gly Lys Gly Leu
        50                  55                  60

Glu Trp Val Ser Gly Ile Phe Phe Asp Gly Glu Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Gln Gln Tyr Phe Asp His Ile Asp Ile Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285
```

```
Asp Pro Glu Val Lys Phe Asn Trp Tyr Val Asp Gly Val Glu Val His
        290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 104
<211> LENGTH: 1401
<212> TYPE: DNA
<213> ORGANISM: Artificial sequence
<220> FEATURE:
<223> OTHER INFORMATION: Synthetic sequence: Sequence encoding SEQ ID
      NO: 103

<400> SEQUENCE: 104
atgaaacacc tgtggttctt cctcctgctg gtggcagctc ccagatgggt cctgtcccag      60
gtgcaattgg tggaaagcgg cggcggcctg gtgcaaccgg gcggcagcct gcgtctgagc     120
tgcgcggcct ccggatttac ctttttcttct tattatatgt cttgggtgcg ccaagccct     180 gggaagggtc tcgagtgggt gagcggtatt tttttttgatg gtgagactta ttatgctgat    240
tctgttaagg gtcgttttac catttcacgt gataattcga aaacacccct gtatctgcaa    300
atgaacagcc tgcgtgcgga agatacggcc gtgtattatt gcgcgcgtca gcagtatttt    360
gatcatattg atatttgggg ccaaggcacc ctggtgacgg ttagctcagc ctccaccaag    420
ggtccatcgg tcttcccccct ggcacccctcc tccaagagca cctctggggg cacagcggcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc gtgcccagca cctgaactcc tgggggggacc gtcagtcttc    780 ctcttccccc caaaacccaa ggacaccctc atgatctccc ggaccccctga ggtcacatgc    840 gtggtggtgg acgtgagcca cgaagaccct gaggtcaagt tcaactggta cgtggacggc    900
gtggaggtgc ataatgccaa gacaaagccg cgggaggagc agtacaacag cacgtaccgg    960
gtggtcagcg tcctcaccgt cctgcaccag gactggctga atggcaagga gtacaagtgc   1020
```

-continued

```
aaggtctcca acaaagccct cccagccccc atcgagaaaa ccatctccaa agccaaaggg    1080
cagccccgag aaccacaggt gtacaccctg ccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaatg a                                              1401
```

<210> SEQ ID NO 105
<211> LENGTH: 466
<212> TYPE: PRT
<213> ORGANISM: Artificial sequence
<220> FEATURE:
<223> OTHER INFORMATION: Synthetic sequence: MOR5164 Heavy Chain IgG1
      (Optimized)

<400> SEQUENCE: 105

```
Met Ala Trp Val Trp Thr Leu Pro Phe Leu Met Ala Ala Ala Gln Ser
 1               5                  10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Tyr Met Ser Trp Val Arg Gln Ala Pro Gly Lys Gly Leu
    50                  55                  60

Glu Trp Val Ser Gly Ile Phe Phe Asp Gly Glu Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
           100                 105                 110

Tyr Cys Ala Arg Gln Gln Tyr Phe Asp His Ile Asp Ile Trp Gly Gln
       115                 120                 125

Gly Thr Leu Val Thr Val Ser Ser Ala Ser Thr Lys Gly Pro Ser Val
   130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285
```

-continued

```
Asp Pro Glu Val Lys Phe Asn Trp Tyr Val Asp Gly Val Glu Val His
        290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 106
<211> LENGTH: 1401
<212> TYPE: DNA
<213> ORGANISM: Artificial sequence
<220> FEATURE:
<223> OTHER INFORMATION: Synthetic sequence: Sequence encoding SEQ ID
      NO: 105

<400> SEQUENCE: 106
atggcttggg tgtggacctt gccattcctg atggcagctg cccaaagtgt ccaggcccag     60
gtgcagctgg tggaatctgg cggcggactg gtgcagcctg gcggcagcct gagactgagc    120
tgcgccgcca gcggcttcac cttcagcagc tactacatga gctgggtgcg gcaggcccct    180
ggcaagggcc tggaatgggt gtccggcatc ttcttcgacg gcgagaccta ctacgccgac    240
agcgtgaagg gccggttcac catcagccgg gacaacagca gaaacaccct gtacctgcag    300
atgaacagcc tgcgggccga ggacaccgcc gtgtactact gcgccaggca gcagtacttc    360
gaccacatcg acatctgggg ccagggcacc ctggtcaccg tctcctcagc ctccaccaag    420
ggcccatcgg tcttccccct ggcaccctcc tccaagagca cctctggggg cacagcggcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tcgtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
```

```
aaggtctcca acaaagccct cccagccccc atcgagaaaa ccatctccaa agccaaaggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctatag caagctcacc gtggacaaga gcaggtggca gcaggggaac    1320
gtcttctcat gctccgtgat gcatgaggct ctgcacaacc actacacgca gaagagcctc    1380
tccctgtccc cgggtaaatg a                                              1401
```

<210> SEQ ID NO 107
<211> LENGTH: 466
<212> TYPE: PRT
<213> ORGANISM: Artificial sequence
<220> FEATURE:
<223> OTHER INFORMATION: Synthetic sequence: MOR5167 Heavy Chain IgG1

<400> SEQUENCE: 107

```
Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Tyr Met Ser Trp Val Arg Gln Ala Pro Gly Lys Gly Leu
    50                  55                  60

Glu Trp Val Ser Gly Ile Phe Phe Asp Gly Thr Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Gln Gln Tyr Phe Asp His Ile Asp Ile Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
```

```
                290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
                340                 345                 350
Lys Thr Ile Ser Lys Ala Lys Gly Gln Pro Arg Glu Pro Gln Val Tyr
                355                 360                 365
Thr Leu Pro Pro Ser Arg Glu Glu Met Thr Lys Asn Gln Val Ser Leu
            370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
                420                 425                 430
Lys Ser Arg Trp Gln Gln Gly Asn Val Phe Ser Cys Ser Val Met His
            435                 440                 445
Glu Ala Leu His Asn His Tyr Thr Gln Lys Ser Leu Ser Leu Ser Pro
450                 455                 460
Gly Lys
465

<210> SEQ ID NO 108
<211> LENGTH: 1401
<212> TYPE: DNA
<213> ORGANISM: Artificial sequence
<220> FEATURE:
<223> OTHER INFORMATION: Synthetic sequence: Sequence encoding SEQ ID
      NO: 107

<400> SEQUENCE: 108
atgaaacacc tgtggttctt cctcctgctg gtggcagctc ccagatgggt cctgtcccag      60
gtgcaattgg tggaaagcgg cggcggcctg gtgcaaccgg cggcagcct gcgtctgagc     120 tgcgcggcct ccggatttac cttttcttct tattatatgt cttgggtgcg ccaagcccct    180
gggaagggtc tcgagtgggt gagcggtatt ttttttgatg gtactactta ttatgctgat    240
tctgttaagg gtcgttttac catttcacgt gataattcga aaaacaccct gtatctgcaa    300
atgaacagcc tgcgtgcgga agatacggcc gtgtattatt gcgcgcgtca gcagtatttt    360
gatcatattg atatttgggg ccaaggcacc ctggtgacgg ttagctcagc tccaccaag    420 ggtccatcgg tcttcccccct ggcaccctcc tccaagagca cctctggggg cacagcggcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgg    960
gtggtcagcg tcctcaccgt cctgcaccag gactggctga atggcaagga gtacaagtgc   1020
```

```
aaggtctcca acaaagccct cccagccccc atcgagaaaa ccatctccaa agccaaaggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcagggaac     1320 gtcttctcat gctccgtgat gcatgaggct ctgcacaacc actacacgca gaagagcctc    1380
tccctgtctc cgggtaaatg a                                              1401
```

<210> SEQ ID NO 109
<211> LENGTH: 466
<212> TYPE: PRT
<213> ORGANISM: Artificial sequence
<220> FEATURE:
<223> OTHER INFORMATION: Synthetic sequence: MOR5167 Heavy Chain IgG1
       (Optimized)

<400> SEQUENCE: 109

```
Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Tyr Met Ser Trp Val Arg Gln Ala Pro Gly Lys Gly Leu
    50                  55                  60

Glu Trp Val Ser Gly Ile Phe Phe Asp Gly Thr Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Gln Gln Tyr Phe Asp His Ile Asp Ile Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
```

|   |   |   |   |   |   |   |   |   |   |   |   |
|---|---|---|---|---|---|---|---|---|---|---|---|
|   |   |   | 290 |   |   |   | 295 |   |   |   | 300 |

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
        340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 110
<211> LENGTH: 1401
<212> TYPE: DNA
<213> ORGANISM: Artificial sequence
<220> FEATURE:
<223> OTHER INFORMATION: Synthetic sequence: Sequence encoding SEQ ID
      NO: 109

<400> SEQUENCE: 110

```
atggcttggg tgtggacctt gccattcctg atggcagctg cccaaagtgt ccaggcccag      60
gtgcagctgg tggaatctgg cggcggactg gtgcagcctg gcggcagcct gagactgagc     120
tgcgccgcca gcggcttcac cttcagcagc tactacatga gctgggtgcg gcaggcccct     180
ggcaagggcc tggaatgggt gtccggcatc ttcttcgacg caccaccta ctacgccgac      240
agcgtgaagg gccggttcac catcagccgg gacaacagca agaacaccct gtacctgcag     300
atgaacagcc tgcgggccga ggacaccgcc gtgtactact gcgccaggca gcagtacttc     360
gaccacatcg acatctgggg ccagggcacc ctggtcaccg tctcctcagc tccaccaag      420
ggcccatcgg tcttccccct ggcaccctcc tccaagagca cctctggggg cacagcggcc     480
ctgggctgcc tggtcaagga ctacttcccc gaaccggtga cggtgtcgtg gaactcaggc     540
gccctgacca gcggcgtgca caccttcccg gctgtcctac agtcctcagg actctactcc     600
ctcagcagcg tcgtgaccgt gccctccagc agcttgggca cccagaccta catctgcaac     660
gtgaatcaca agcccagcaa caccaaggtg gacaagagag ttgagcccaa atcttgtgac     720
aaaactcaca catgcccacc gtgcccagca cctgaactcc tggggggacc gtcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
```

-continued

```
aaggtctcca acaaagccct cccagccccc atcgagaaaa ccatctccaa agccaaaggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc tcccgtgctg gactccgac     1260 ggctccttct tcctctatag caagctcacc gtggacaaga gcaggtggca gcaggggaac    1320
gtcttctcat gctccgtgat gcatgaggct ctgcacaacc actacacgca gaagagcctc    1380
tccctgtccc cgggtaaatg a                                              1401
```

<210> SEQ ID NO 111
<211> LENGTH: 466
<212> TYPE: PRT
<213> ORGANISM: Artificial sequence
<220> FEATURE:
<223> OTHER INFORMATION: Synthetic sequence: MOR5170 Heavy Chain IgG1

<400> SEQUENCE: 111

```
Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Tyr Met Ser Trp Val Arg Gln Ala Pro Gly Lys Gly Leu
    50                  55                  60

Glu Trp Val Ser Gly Thr Phe Phe Asp Gly Ser Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Gln Gln Tyr Phe Asp His Ile Asp Ile Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300
```

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
450                 455                 460

Gly Lys
465

<210> SEQ ID NO 112
<211> LENGTH: 1401
<212> TYPE: DNA
<213> ORGANISM: Artificial sequence
<220> FEATURE:
<223> OTHER INFORMATION: Synthetic sequence: Sequence encoding SEQ ID
      NO: 111

<400> SEQUENCE: 112
atgaaacacc tgtggttctt cctcctgctg gtggcagctc ccagatgggt cctgtcccag      60
gtgcaattgg tggaaagcgg cggcggcctg gtgcaaccgg cggcagcct gcgtctgagc      120 tgcgcggcct ccggatttac ctttttcttct tattatatgt cttgggtgcg ccaagcccct     180
gggaagggtc tcgagtgggt gagcggtact tttttttgatg gttctactta ttatgctgat    240
tctgttaagg gtcgttttac catttcacgt gataattcga aaaacaccct gtatctgcaa     300
atgaacagcc tgcgtgcgga agatacggcc gtgtattatt gcgcgcgtca gcagtatttt    360
gatcatattg atatttgggg ccaaggcacc ctggtgacgg ttagctcagc tccaccaag    420 ggtccatcgg tcttcccct ggcaccctcc tccaagagca cctctggggg cacagcggcc     480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac   660
gtgaatcaca agcccagcaa caccaaggtg gacaagagag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc   900
gtggaggtgc ataatgccaa gacaaagccg cgggaggagc agtacaacag cacgtaccgg    960
gtggtcagcg tcctcaccgt cctgcaccag gactggctga atggcaagga gtacaagtgc  1020
aaggtctcca acaaagccct cccagccccc atcgagaaaa ccatctccaa agccaaaggg   1080

-continued

```
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaatg a                                              1401
```

<210> SEQ ID NO 113
<211> LENGTH: 466
<212> TYPE: PRT
<213> ORGANISM: Artificial sequence
<220> FEATURE:
<223> OTHER INFORMATION: Synthetic sequence: MOR5170 Heavy Chain IgG1
      (Optimized)

<400> SEQUENCE: 113

```
Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Tyr Met Ser Trp Val Arg Gln Ala Pro Gly Lys Gly Leu
    50                  55                  60

Glu Trp Val Ser Gly Thr Phe Phe Asp Gly Ser Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Gln Gln Tyr Phe Asp His Ile Asp Ile Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300
```

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
            450                 455                 460

Gly Lys
465

<210> SEQ ID NO 114
<211> LENGTH: 1401
<212> TYPE: DNA
<213> ORGANISM: Artificial sequence
<220> FEATURE:
<223> OTHER INFORMATION: Synthetic sequence: Sequence encoding SEQ ID
      NO: 113

<400> SEQUENCE: 114
atggcttggg tgtggacctt gccattcctg atggcagctg cccaaagtgt ccaggcccag    60
gtgcagctgg tggaatctgg cggcggactg gtgcagcctg gcggcagcct gagactgagc   120
tgcgccgcca gcggcttcac cttcagcagc tactacatga gctgggtgcg gcaggcccct   180
ggcaagggcc tggaatgggt gtccggcacc ttcttcgacg gcagcaccta ctacgccgac   240
agcgtgaagg gccggttcac catcagccgg gacaacagca gaacaccct gtacctgcag    300 atgaacagcc tgcgggccga ggacaccgcc gtgtactact gcgccaggca gcagtacttc   360
gaccacatcg acatctgggg ccagggcacc ctggtcaccg tctcctcagc ctccaccaag   420
ggcccatcgg tcttccccct ggcaccctcc tccaagagca cctctggggg cacagcggcc   480
ctgggctgcc tggtcaagga ctacttcccc gaaccggtga cggtgtcgtg gaactcaggc   540
gccctgacca gcggcgtgca caccttcccg gctgtcctac agtcctcagg actctactcc   600
ctcagcagcg tcgtgaccgt gccctccagc agcttgggca cccagaccta catctgcaac   660
gtgaatcaca agcccagcaa caccaaggtg gacaagagag ttgagcccaa atcttgtgac   720
aaaactcaca catgcccacc gtgcccagca cctgaactcc tggggggacc gtcagtcttc   780
ctcttccccc caaaacccaa ggacaccctc atgatctccc ggaccctga ggtcacatgc    840 gtggtggtgg acgtgagcca cgaagaccct gaggtcaagt tcaactggta cgtggacggc   900
gtggaggtgc ataatgccaa gacaaagccg cgggaggagc agtacaacag cacgtaccgt   960
gtggtcagcg tcctcaccgt cctgcaccag gactggctga atggcaagga gtacaagtgc   1020
aaggtctcca acaaagccct cccagccccc atcgagaaaa ccatctccaa agccaagggg   1080

```
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctatag caagctcacc gtggacaaga gcaggtggca gcagggaac    1320 gtcttctcat gctccgtgat gcatgaggct ctgcacaacc actacacgca gaagagcctc    1380
tccctgtccc cgggtaaatg a                                              1401

<210> SEQ ID NO 115
<211> LENGTH: 7
<212> TYPE: PRT
<213> ORGANISM: Homo sapiens

<400> SEQUENCE: 115

Lys Lys Arg Arg Lys Arg Lys
1               5
```